US010935541B2

(12) United States Patent
Hickman et al.

(10) Patent No.: US 10,935,541 B2
(45) Date of Patent: Mar. 2, 2021

(54) DEVICES AND METHODS COMPRISING NEUROMUSCULAR JUNCTIONS

(71) Applicant: University of Central Florida Research Foundation, Inc., Orlando, FL (US)

(72) Inventors: James Hickman, Orlando, FL (US); Alexander Smith, Seattle, WA (US); Christopher Long, Orlando, FL (US); Kristen Pirozzi, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 680 days.

(21) Appl. No.: 14/821,675

(22) Filed: Aug. 7, 2015

(65) Prior Publication Data

US 2016/0041150 A1 Feb. 11, 2016

Related U.S. Application Data

(60) Provisional application No. 62/034,217, filed on Aug. 7, 2014.

(51) Int. Cl.
*G01N 33/50* (2006.01)
*G01N 33/487* (2006.01)

(52) U.S. Cl.
CPC ... *G01N 33/5061* (2013.01); *G01N 33/48728* (2013.01); *G01N 33/5058* (2013.01)

(58) Field of Classification Search
CPC ......... G01N 33/5061; G01N 33/48728; G01N 33/5058; G01N 27/041
See application file for complete search history.

(56) References Cited

U.S. PATENT DOCUMENTS

| 5,442,510 | A | 8/1995 | Schwartz et al. |
| 5,682,899 | A | 11/1997 | Nashef et al. |
| 5,948,621 | A | 9/1999 | Turner et al. |
| 6,866,383 | B2 | 3/2005 | Naik et al. |
| 6,916,541 | B2 | 7/2005 | Pantano et al. |
| 6,935,165 | B2 | 8/2005 | Bashir et al. |
| 7,384,786 | B2 | 6/2008 | Freyman et al. |
| 7,541,146 | B2 | 6/2009 | Lewis |
| 7,579,189 | B2 | 8/2009 | Freyman et al. |
| 7,691,629 | B2 | 4/2010 | Johe et al. |
| 7,860,563 | B2 | 12/2010 | Foreman et al. |
| 7,923,015 | B2 | 4/2011 | V-Martinez et al. |
| 7,927,671 | B2 | 4/2011 | Kato |
| 8,071,319 | B2 | 12/2011 | Metzger et al. |
| 8,178,602 | B2 | 5/2012 | Mao et al. |
| 8,318,488 | B1 | 11/2012 | Bohlen |
| 8,318,489 | B2 | 11/2012 | Davidson et al. |
| 8,318,951 | B2 | 11/2012 | Olson et al. |
| 8,828,721 | B1 | 9/2014 | Hickman et al. |
| 2003/0054355 | A1 | 3/2003 | Warthoe |
| 2003/0065452 | A1 | 4/2003 | Hickman |
| 2003/0144823 | A1 | 7/2003 | Fox et al. |
| 2003/0211542 | A1 | 11/2003 | Lee et al. |
| 2005/0074834 | A1 | 4/2005 | Chaplen et al. |
| 2006/0105457 | A1 | 5/2006 | Rameshwar |
| 2006/0259992 | A1 | 11/2006 | Koren et al. |
| 2007/0015138 | A1 | 1/2007 | Barlow et al. |
| 2007/0037225 | A1 | 2/2007 | Metzger et al. |
| 2007/0089515 | A1 | 4/2007 | Shih et al. |
| 2007/0117217 | A1 | 5/2007 | Lal et al. |
| 2007/0122896 | A1 | 5/2007 | Shuler et al. |
| 2007/0129447 | A1 | 6/2007 | Sra |
| 2007/0212723 | A1 | 9/2007 | Dudley et al. |
| 2007/0218534 | A1 | 9/2007 | Klenerman et al. |
| 2008/0124789 | A1 | 5/2008 | Hickman |
| 2008/0138797 | A1* | 6/2008 | Hunt ................. B82Y 5/00 435/6.16 |
| 2008/0166795 | A1 | 7/2008 | Shuler et al. |
| 2008/0227137 | A1 | 9/2008 | Zhang et al. |
| 2009/0029463 | A1 | 1/2009 | Collins |
| 2009/0078023 | A1 | 3/2009 | Mutharasan et al. |
| 2009/0227469 | A1 | 9/2009 | Conklin et al. |
| 2009/0239940 | A1 | 9/2009 | Del Monte et al. |
| 2009/0305319 | A1 | 12/2009 | Baudenbacher |
| 2010/0028902 | A1 | 2/2010 | Brown et al. |
| 2012/0135452 | A1 | 5/2012 | Shuler et al. |

(Continued)

FOREIGN PATENT DOCUMENTS

| CA | 2788905 | 8/2011 |
| CA | 2798777 | 10/2011 |

(Continued)

OTHER PUBLICATIONS

Smith et al., A functional system for high-content screening of neuromuscular junctions in vitro, Technology (Singap World Sci). 2013 ; 1(1): 37-48. doi:10.1142/S2339547813500015.*

Wilson et al., Measurement of Contractile Stress Generated by Cultured Rat Muscle on Silicon Cantilevers for Toxin Detection and Muscle Performance Enhancement, PLoS One, Jun. 2010, vol. 5, Issue 6.*

Park et al., Neuromuscular Junction in a Microfluidic Device, 35th Annual International Conference of the IEEE EMBS Osaka, Japan, Jul. 3-7, 2013.*

Morin et al., Constraining the connectivity of neuronal networks cultured on microelectrode arrays with microfluidic techniques: A step towards neuron-based functional chips, Biosensors and Bioelectronics 21 (2006) 1093-1100.*

(Continued)

*Primary Examiner* — Blaine Lankford
(74) *Attorney, Agent, or Firm* — Meunier Carlin & Curfman LLC

(57) ABSTRACT

Disclosed herein are devices comprising one or more cantilevers comprising one or more neuromuscular junctions formed by a co-culture of myotubes and motoneurons. Disclosed herein are methods of using the disclosed devices comprising one or more cantilevers. This abstract is intended as a scanning tool for purposes of searching in the particular art and is not intended to be limiting of the present invention.

21 Claims, 17 Drawing Sheets

(56) References Cited

U.S. PATENT DOCUMENTS

| | | |
|---|---|---|
| 2012/0142556 A1 | 6/2012 | Parker et al. |
| 2014/0274796 A1 | 9/2014 | Hickman |
| 2015/0219622 A1 | 8/2015 | Hickman |

FOREIGN PATENT DOCUMENTS

| | | | |
|---|---|---|---|
| EP | 2434896 | 4/2012 | |
| EP | 2435585 | 4/2012 | |
| EP | 2531910 | 12/2012 | |
| EP | 2585171 | 5/2013 | |
| WO | 2005/033264 | 4/2005 | |
| WO | 2005/108598 | 11/2005 | |
| WO | 2009/036573 | 3/2009 | |
| WO | 2010/127280 | 11/2010 | |
| WO | WO 2010/127280 | * 11/2010 | ............ C12Q 1/00 |
| WO | 2010/138679 | 12/2010 | |
| WO | 2010/138782 | 12/2010 | |
| WO | 2011/097574 | 8/2011 | |
| WO | 2011/133985 | 10/2011 | |
| WO | 2012/158923 | 11/2012 | |
| WO | 2001/029206 | 1/2013 | |
| WO | 2013/013206 | 1/2013 | |
| WO | 2014/028940 | 2/2014 | |
| WO | WO 2014/028940 | * 2/2014 | ............ C12M 1/34 |
| WO | 2014/120952 | 8/2014 | |

OTHER PUBLICATIONS

Cogollo et al., A new integrated system combining AFM and MEA for measuring the mechanical properties of living cardiac myocytes, Biomed Microdevices, 2011, 13:613-621.*

U.S. Appl. No. 12/661,323, filed Mar. 15, 2010, James Hickman.

U.S. Appl. No. 12/938,701, filed Nov. 3, 2010, Peter Molnar.

U.S. Appl. No. 14/422,082, filed Feb. 17, 2015, James J. Hickman.

U.S. Appl. No. 14/764,683, filed Jul. 30, 2015, James Hickman.

U.S. Appl. No. 14/214,822, filed Mar. 15, 2014, James J. Hickman.

Shuker ML. (2012) Functional In Vitro System for Drug Discovery.

Hierlemann, A., "CMOS-Based Bio/Chemosensor and Bioelectronic Microsystems", Procedia Chemistry, Elsevier, Amsterdam, NL, vol. 1, No. 1, Sep. 2009, pp. 5-8.

Jose Francisco Saenz Cogollo et al., "A Novel AFM-MEA Platform for Studying the Real Time Mechano-Electrical Behavior of Cardiac Myocytes", MRS Proceedings, vol. 1261, 2010, pp. 17-22.

Supplementary European Search Report issued in European Application No. EP 14745661, dated Aug. 10, 2016.

Abbanat D, et al. (2003) Novel antibacterial agents for the treatment of serious Gram-positive infections. Expert Opin Investig Drugs. 12: 379-399.

Abdi H. (2003) Multivariate Analysis. Encyclopedia of Social Sciences Research Methods. M. Lewis-Beck, A. Bryman and T. Futing. Thousand Oaks (CA), Sage.

Adell A, et al. (2002) Origin and functional role of the extracellular serotonin in the midbrain raphe nuclei. Brain Res Brain Res Rev. 39: 154-180.

Agarwal A, et al. (2013) Microfluidic heart on a chip for higher throughput pharmacological studies. Lab Chip. 13: 3599-3608.

Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study of long-term drug effects on synaptic activity. Drug Development Research. 68: 84-93.

Ainscow EK and Brand MD. (1999) Internal regulation of ATP turnover, glycolysis and oxidative phosphorylation in rat hepatocytes. Eur J Biochem. 266:737-749.

Akaaboune M, et al. (2000) Developmental regulation of amyloid precursor A123. protein at the neuromuscular junction in mouse skeletal muscle. Mol Cell Neurosci. 15: 355-367.

Akanda N, et al. (2008) Effect of malonate, a metabolic pathway inhibitor, on A124. action potential peak shape and the relationship to cellular pathways. 38th Annual Meeting of the Society for Neuroscience. vol. 3 8.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R and Othmer H. (2003) The topology of the regulatory interactions predicts the expression pattern of the segment polarity genes in Drosophila melanogaster. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) An atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

Alterio J, et al. (1990) Acidic and basic fibroblast growth factor mRNAs are expressed by skeletal muscle satellite cells.Biochem Biophys Res Commun. 166:1205-1212.

Altmann L. (2000) Multielectrode recordings of synaptic plasticity in brain slices: A new method for the assessment of neurotoxic effects. European Journal of Neuroscience. 12: 29-29.

Amarenco P, et al. (2006) High-dose atorvastatin after stroke or transient ischemic attack. N Engl J Med. 355: 549-559.

Amit M. (2007) Feeder-layer free culture system for human embryonic stem cells. Methods Mol Biol. 407: 11-20.

Anderson DJ, et al. (1997) Cell lineage determination and the control of neuronal identity in the neural crest. Cold Spring Harb Symp Quant Biol. 62: 493-504.

Anderson JE, et al. (1991) Distinctive patterns of basic fibroblast growth factor (bFGF) distribution in degenerating and regenerating areas of dystrophic (mdx) striated muscles. Dev Biol. 147: 96-109.

Andersson Hand van den Berg A. (2004) Microfabrication and microfluidics for tissue engineering: state of the art and future opportunities. Lab Chip. 4: 98-103.

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Aracil A, et al. (2004) Proceedings of Neuropeptides 2004, the XIV European Neuropeptides Club meeting. Neuropeptides. 38: 369-371.

Archer JD, et al. (2006) Persistent and improved functional gain in mdx dystrophic mice after treatment with L-arginine and deflazacort. F ASEB J. 20:738-740.

Agarwal, A., Goss, J.A., Cho, A., McCain, M.L. & Parker, K.K. Microfluidic heart on a chip for higher throughput pharmacological studies. Lab Chip 13, 3599-3608 (2013).

Armstrong DL and Rossie S. (1999) Ion channel regulation. Introduction. Adv Second Messenger Phosphoprotein Res. 33: ix-xx.

Arnold HH and Winter B. (1998) Muscle differentiation: more complexity to the network of myogenic regulators. Curr Opin Genet Dev. 8: 539-544.

Arnone MI and Davidson EH. (1997) The hardwiring of development: organization and function of genomic regulatory systems. Development. 124:1851-1864.

Arsic N, et al. (2004) Vascular endothelial growth factor stimulates skeletal muscle regeneration in vivo. Mol Ther. 10: 844-854.

(56) References Cited

OTHER PUBLICATIONS

Askanas V, et al. (1987) De novo neuromuscular junction formation on human muscle fibres cultured in monolayer and innervated by foetal rat spinal cord: ultrastructural and ultrastructural-cytochemical studies. J Neurocytol. 16: 523-537.
Asotra K and Macklin WB. (1993) Protein kinase C activity modulates myelin gene expression in enriched oligodendrocytes. J Neurosci Res. 34: 571-588.
Azzouz M, et al. (2004) VEGF delivery with retrogradely transported lentivector prolongs survival in a mouse ALS model. Nature. 429: 413-417.
Badie N, et al. (2009) A method to replicate the microstructure of heart tissue in vitro using DTMRI-based cell micropatterning. Ann Biomed Eng. 37: 2510-2521.
Badie et al. (2009b) Novel micropatterned cardiac cell cultures with realistic ventricular microstructure. Biophysical Journal 96: 3873-3885.
Bahr M, et al. (1991) In vitro myelination of regenerating adult rat retinal ganglion cell axons by Schwann cells. Glia. 4: 529-533.
Baker DC, et al. (2002) The origin and neuronal function of in vivo nonsynaptic glutamate. J Neurosci. 22: 9134-9141.
Bandi E, et al. (2008) Neural agrin controls maturation of the excitation-contraction coupling mechanism in human myotubes developing in vitro. Am J Physiol Cell Physiol. 294: C66-C73.
Bansal R and Pfeiffer SE. (1992) Novel stage in the oligodendrocyte lineage defined by reactivity of progenitors with R-mAb pnor to QI antigalactocerebroside. J Neurosci Res. 32: 309-316.
Baraban SC, et al. (1997) Osmolarity modulates K+ channel function on rat AI56. hippocampal interneurons but not CAI pyramidal neurons. J Physiol. 498: 679-689.
Barbulovic-Nad I, et al. (2008) Digital microfluidics for cell-based assays. Lab Chip. 8: 519-526.
Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.
Barone FC, et al. (1998) Ischemic preconditioning and brain tolerance: temporal histological and functional outcomes, protein synthesis requirement, and interleukin-I receptor antagonist and early gene expression. Stroke. 29: 1937-1950.
Behar TN. (2001) Analysis of fractal dimension of 02A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid AI. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by musclederived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372.
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle A191. development and neuromuscular diseases Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal A195. differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.

(56) References Cited

OTHER PUBLICATIONS

Brewer GJ. (1997) Isolation and culture of adult rat hippocampal neurons. J Neurosci Methods. 71: 143-155.

Brewer GJ. (1999) Regeneration and proliferation of embryonic and adult rat hippocampal neurons in culture. Exp Neurol. 159: 237-247.

Brito-Martins M, et al. (2008) beta(I)- and beta(2)-adrenoceptor responses in cardiomyocytes derived from human embryonic stem cells: comparison with failing and non-failing adult human heart. Br J Pharmacol. 153: 751-759.

Brockes JP, et al. (1979) Studies on cultured rat Schwann cells. I. Establishment of purified populations from cultures of peripheral nerve. Brain Res. 165: 105-118.

Brokhman I, et al. (2008) Peripheral sensory neurons differentiate from neural precursors derived from human embryonic stem cells. Differentiation. 76: 145-155.

Brumovsky P, et al. (2007) Expression of the vesicular glutamate transporters-I and -2 in adult mouse dorsal root ganglia and spinal cord and their regulation by nerve injury. Neuroscience. 147: 469-490.

Bult CJ, et al. (1996) Complete genome sequence of the methanogenic archaeon, Methanococcus jannaschii. Science. 273: 1058-1073.

Bunge MB, et al. (1962) Electron microscopic demonstration of connections between glia and myelin sheaths in the developing mammalian central nervous system. J Cell Biol. 12: 448-453.

Bunge RP. (1968) Glial cells and the central myelin sheath. Physiol Rev. 48: 197-251.

Bunge RP. (1993) Expanding roles for the Schwann cell: ensheathment, myelination, trophism and regeneration. Curr Opin Neurobiol. 3: 805-809.

Burdick JA and Vunjak-Novakovic G. (2008) Engineered microenvironments for controlled stem cell differentiation. Tissue Eng Part A. 15: 205-219.

Burgess C, et al. (2008) An endogenous glutamatergic drive onto somatic motoneurons contributes to the stereotypical pattern of muscle tone across the sleep-wake cycle. J Neurosci. 28: 4649-4660.

Butt HJ. (1996) Sensitive Method to Measure Changes in the Surface Stress of Solids. Journal of Colloid and Interface Science. 180: 251-260.

Buzanska L, et al. (2002) Human cord blood-derived cells attain neuronal and glial features in vitro. J Cell Sci. 115: 2131-2138.

Cai J, et al. (2007) Directed differentiation of human embryonic stem cells into functional hepatic cells. Hepatologv. 45: 1229-1239.

Caiozzo VJ, at al. (1992) Response of slow and fast muscle to hypothyroidism: maximal shortening velocity and myosin isoforms. Am J Physiol. 263: C86-C94.

Cakir T, et al. (2007) Reconstruction and flux analysis of coupling between metabolic pathways of astrocytes and neurons: application to cerebral hypoxia. Theor Biol Med Model. 4: 48.

Campbell TJ and Williams KM. (2001) Therapeutic drug monitoring: antiarrhythmic drugs. Br J Clin Pharmacol. 52 Suppl 1: 21S-34S.

Camu Wand Henderson CE. (1992) Purification of embryonic rat motoneurons by panning on a monoclonal antibody to the low-affinity NGF receptor. J Neurosci Methods. 44: 59-70.

Camu W and Henderson CE. (1994) Rapid purification of embryonic rat motoneurons: an in vitro model for studying MND/ALS pathogenesis. J Neurol Sci. 124 Suppl: 73-74.

Cannon JG. (1998) Intrinsic and extrinsic factors in muscle aging. Ann NY Acad Sci. 854: 72-77.

Caratsch CG, et al. (1994) Interferon-alpha, beta and tumor necrosis factor-alpha enhance the frequency of miniature end-plate potentials at rat neuromuscular junction. Neurosci Lett. 166: 97-100.

Carlsson L. (2006) In vitro and in vivo models for testing arrhythmogenesis in drugs. J Intern Med. 259: 70-80.

Carpenedo RL, et al. (2007) Rotary suspension culture enhances the efficiency, yield, and homogeneity of embryoid body differentiation. Stem Cells. 25: 2224-2234.

Carr PA, et al. (1989) Parvalbumin is highly colocalized with calbindin D28k and rarely with calcitonin gene-related peptide in dorsal root ganglia neurons of rat. Brain Res. 497: 163-170.

Carrasco DI and English AW. Neurotrophin 4/5 is required for the normal development of the slow muscle fiber phenotype in the rat soleus. J Exp Biol. 206: 2191-2200.

Caspi O, et al. (2009) In vitro electrophysiological drug testing using human embryonic stem cell derived cardiomyocytes. Stem Cells Dev. 18: 161-172.

Catoire H, et al. (2008) Sirtuin inhibition protects from the polyalanine muscular dystrophy protein PABPNI. Hum Mol Genet. 17: 2108-2117.

Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.

Chambers SM, et al. (2009) Highly efficient neural conversion of human ES and iPS cells by dual inhibition of SMAD signaling. Nat Biotechnol. 27: 275-280.

Chandran S, et al. (1998) Regional potential for oligodendrocyte generation in the rodent embryonic spinal cord following exposure to EGF and FGF-2. Glia. 24: 382-389.

Chang JC, et al. (2001) Modulation of neural network activity by patterning. Biosens Bioelectron. 16: 527-533.

Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.

Chaudhary KW, et al. (2006) Embryonic stem cells in predictive cardiotoxicity: laser capture microscopy enables assay development. Toxicol Sci. 90: 149-158.

Chaves M, et al. (2005) Robustness and fragility of Boolean models for genetic regulatory networks. J Theor Biol. 235: 431-449.

Chaves M, et al. (2006) Methods of robustness analysis for Boolean models of gene control networks. Syst Biol (Stevenage). 153: 154-167.

Chen CS, et al. (1997) Geometric control of cell life and death. Science. 276: 1425-1428.

Chen EW, et al. (1995) Target regulation of a motor neuron-specific epitope. J Neurosci. 15: 1555-1566.

Chen J and von Bartheld CS. (2004) Role of exogenous and endogenous trophic factors m the regulation of extraocular muscle strength during development.Invest Ophthalmol Vis Sci. 45: 3538-3545.

Chen QS, et al. (2000) Impairment of hippocampal long-term potentiation by Alzheimer amyloid beta-peptides. J Neurosci Res. 60: 65-72.

Chen X, et al. (2005) Dedifferentiation of adult human myoblasts induced by ciliary neurotrophic factor in vitro. Moll Biol Cell. 16: 3140-3151.

Chen XF, et al. (2008) Dynamic simulation of the effect of calcium-release activated calcium channel on cytoplasmic Ca2+ oscillation. Biophys Chem. 136: 87-95.

Chen XP, (2003) Exogenous rhCNTF inhibits myoblast differentiation of skeletal muscle of adult human in vitro. Sheng Li Xue Bao. 55: 464-468.

Chiu A Y, et al. (1993) A motor neuron-specific epitope and the low-affinity nerve growth factor receptor display reciprocal patterns of expression during development, axotomy, and regeneration. J Comp Neurol. 328: 351-363.

Choi-Lundberg DL and Bohn MC. (1995) Ontogeny and distribution of glial cell line-derived neurotrophic factor (GDNF) mRNA in rat. Brain Res Dev Brain Res. 85: 80-88.

Choudhury A, et al. (2007) A piezoresistive microcantilever array for surface stress measurement: curvature model and fabrication. J Micromech Microeng. 17: 2065-2076.

Chow I and Poo MM. (1985) Release of acetylcholine from embryonic neurons upon contact with muscle cell. J Neurosci. 5: 1076-1082.

Christ B and Brand-Seberi B. (2002) Limb muscle development. Int J Dev Biol. 46: 905-914.

(56) References Cited

OTHER PUBLICATIONS

Cizkova D, et al. (2007) Functional recovery in rats with ischemic paraplegia after spinal grafting of human spinal stem cells. Neuroscience. 147: 546-560.
Clegg CH, et al. (1987) Growth factor control of skeletal muscle differentiation: commitment to terminal differentiation occurs in G1 phase and is repressed by fibroblast growth factor. J Cell Biol. 105: 949-956.
Clements JD, et al. (1992) The time course of glutamate in the synaptic cleft. Science. 258: 1498-1501.
Coggan JS, et al. (2005) Evidence for ectopic neurotransmission at a neuronal synapse. Science. 309: 446-451.
Cohen RI and Almazan G. (1993) Norepinephrine-stimulated PI hydrolysis in oligodendrocytes is mediated by alpha IA-adrenoceptors. Neuroreport. 4: 1115-1118.
Cohen-Cory S. (2002) The developing synapse: construction and modulation of synaptic structures and circuits. Science. 298: 770-776.
Collins CA and Morgan JE. (2003) Duchenne's muscular dystrophy: animal models used to investigate pathogenesis and develop therapeutic strategies. Int J Exp Pathol. 84: 165-172.
Colomar A and Robitaille R. (2004) Glial modulation of synaptic transmission at the neuromuscular junction. Glia. 4 7: 284-289.
Cooper A, et al. (1976) The growth of mouse neuroblastoma cells in controlled orientations on thin films of silicon monoxide. Exp Cell Res. 103: 435-439.
Corey JM, et al. (1991) Compliance of hippocampal neurons to patterned substrate networks. J Neurosci Res. 30: 300-307.
Corey JM, et al. (1996) Micrometer resolution silane-based patterning of hippocampal neurons: critical variables in photoresist and laser ablation processes for substrate fabrication. IEEE Trans Biomed Eng. 43: 944-955.
Corey JM, et al. (1997) Differentiated B 104 neuroblastoma cells are a highresolution assay for micropatterned substrates. J Neurosci Methods. 75: 91-97.
Cortassa S, et al. (2003) An integrated model of cardiac mitochondrial energy metabolism and calcium dynamics. Biophys J. 84: 2734-2755.
Cossu G, et al. (1996) How is myogenesis initiated in the embryo? Trends Genet. 12: 218-223.
Courdier-Fruh I, et al. (2002) Glucocorticoid-mediated regulation of utrophin levels in human muscle fibers. Neuromuscul Disord. 12(Suppl 1): S95-S104.
Cross-Doersen D and Isfort RJ. (2003) A novel cell-based system for evaluating skeletal muscle cell hypertrophy-inducing agents. In Vitro Cell Dev Biol Animal. 39: 407-412.
Cukierman E, et al. (2002) Cell interactions with three-dimensional matrices. Curr Opin Cell Biol. 14: 633-639.
Cunningham JJ and Roussel MF. (2001) Cyclin-dependent kinase inhibitors in the development of the central nervous system. Cell Growth Differ. 12: 387-396.
Cuppini R, et al. (2001) Alpha-tocopherol controls cell proliferation in the adult rat dentate 12:vrus. Neurosci Lett. 303: 198-200.
Currie PD and Ingham PW. (1996) Induction of a specific muscle cell type by a hedgehog-like protein in zebrafish. Nature. 382: 452-455.
Curtis R, et al. (1988) Development of macroglial cells in rat cerebellum. I. Use of antibodies to follow early m VIVO development and migration of oligodendrocytes. J Neurocytol. 17: 43-54.
Cysyk J and Tung L. (2008) Electric field perturbations of spiral waves attached to millimeter-size obstacles. Biophys J. 94: 1533-1541.
Dakhel Y and Jamali F. (2006) Erythromycin potentiates PR interval prolonging effect of verapamil in the rat: a pharmacodynamic drug interaction. Toxicol Appl Pharmacol. 214: 24-29.
Daniels MP, et al. (2000) Rodent nerve-muscle cell culture system for studies of neuromuscular junction development: refinements and applications. Microsc Res Tech. 49: 26-37.
Daniels MP. (1990) Localization of actin, beta-spectrin, 43×10(3) Mr and 58×10(3) Mr proteins to receptor-enriched domains of newly formed acetylcholine receptor aggregates in isolated myotube membranes. J Cell Sci. 97(Pt 4): 615-626.
Daniels MP. (1997) Intercellular communication that mediates formation of the neuromuscular iunction. Mol Neurobiol. 14: 143-170.
Das M, et al. (2003) Electrophysiological and morphological characterization of rat embryonic motoneurons in a defined system. Biotechnol Prog. 19: 1756-1761.
Das M, et al. (2004) Long-term culture of embryonic rat cardiomyocytes on an organosilane surface in a serum-free medium. Biomaterials. 25: 5643-5647.
Das M, et al. (2005) Adult rat spinal cord culture on an organosilane surface in a novel serum-free medium. In Vitro Cell Dev Biol Anim. 41: 343-348.
Das M, et al. (2006) A defined system to allow skeletal muscle differentiation and subsequent integration with silicon microstructures. Biomaterials. 27: 4374-4380.
Das M, et al. (2007a) Auto-catalytic ceria nanoparticles offer neuroprotection to adult rat spinal cord neurons. Biomaterials. 28: 1918-1925.
Das M, et al. (2007b) Differentiation of skeletal muscle and integration of myotubes with silicon microstructures using serum-free medium and a synthetic silane substrate. Nat Protoc. 2: 1795-1801.
Das M, et al. (2007c) Embryonic motoneuron-skeletal muscle co-culture in a defined system. Neuroscience. 146: 481-488.
Das M, et al. (2008) Temporal neurotransmitter conditioning restores the functional activity of adult spinal cord neurons in long-term culture. Exp Neurol. 209: 171-180.
Das M, et al. (2009a) Developing a novel serum-free cell culture model of skeletal muscle differentiation by systematically studying the role of different growth factors in myotube formation. In Vitro Cell Dev Biol Anim. 45: 378-387.
Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.
Das M, et al. (2010) A defined long-term in vitro tissue engineered model of neuromuscular junctions. Biomaterials. 31: 4880-4888.
Datar R, et al. (2009) Cantilever Sensors: Nanomechanical Tools for Diagnostics. MRS Bulletin. 34: 449-454.
David JA and Pitman RM. (1982) The effects of axotomy upon the extrasynaptic acetylcholine sensitivity of an identified motoneurone m the cockroach *Periplaneta americana*. J Exp Biol. 98: 329-341.
Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.
De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.
De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.
De Lange P, et al. (2006) Sequential changes in the signal transduction responses of skeletal muscle following food deprivation. FASEB J. 20: 2579-2581.
De Wilde J, et al. (2008) Short-term high fat-feeding results in morphological and metabolic adaptations m the skeletal muscle of C57BL/6J mice. Physiol Genomics. 32: 360-369.
Dell'Era P, et al. (2003) Fibroblast growth factor receptor-I is essential for in vitro cardiomyocyte development. Circ Res. 93: 414-420.
Denning C and Anderson D. (2008) Cardiomyocytes from human embryonic A291. stem cells as predictors of cardiotoxicity. Drug Discovery Today: Therapeutic Strategies. 5: 223-232.
Dennis RG and Kosnik IPE. (2000) Excitability and isometric contractile A292. properties of mammalian skeletal muscle constructs engineered in vitro. In Vitro Cell Dev Biol Anim. 36: 327-335.

(56) References Cited

OTHER PUBLICATIONS

Dennis RG, et al. (2001) Excitability and contractility of skeletal muscle A293. engineered from primary cultures and cell lines. Am J Physiol Cell Physiol. 280: C288-C295.

Denyer MCT, et al. (1998) Preliminary study on the suitability of a A294. pharmacological bio-assay based on cardiac myocytes cultured over microfabricated microelectrode arrays. Med Biol Eng Comput. 36: 638-644.

Descarries L, et al. (1997) Diffuse transmission by acetylcholine in the CNS. Prog Neurobiol. 53: 603-625.

Dhavan Rand Tsai L. (2001) A decade of CDK5. Nat Rev Mol Cell Biol. 2: 749-759.

Dhir, V. (2003) Application of polyelectrolyte multilayers for photolithographic patterning of diverse mammalian cell types in serum free medium. Masters Thesis in the Department of Mechanical, Materials and Aerospace Engineering in the College of Engineering and Computer Science. University of Central Florida. Orlando, Florida, Fall Term 2008.

Dhir V, et al. (2009) Patterning of diverse mammalian cell types in serum free medium with photoablation. Biotechnol Prog. 25: 594-603.

Di Giovanni S, et al. (2005) Cell cycle inhibition provides neuroprotection and reduces glial proliferation and scar formation after traumatic brain injury. Proc Natl Acad Sci U SA. 102: 8333-8338.

Dimitrova DS and Gilbert DM. (2000) Temporally coordinated assembly and disassembly of replication factories in the absence of DNA synthesis. Nat Cell Biol. 2: 686-694.

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacolo12:v. 24: 254-264.

Duport S. et al. (1999) A metallic multisite recording system designed for continuous long-term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes m vitro. Differentiation. 65: 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microeletrode arrays. In: Taketani M BM, editor. Advances m netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/ Akt pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression ofhomeobox gene Islet-I. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by selfassembly processes. Bioorg Med Chem. 7: 75-81.

Figenschou A, et al. (1996) Cholinergic modulation of the action potential in rat hippocampal neurons. EurJ Neurosci. 8: 211-219.

Fink CC, et al. (1999) Determination of time-dependent inositol-1,4,5-trisphosphate concentrations during calcium release in a smooth muscle cell. Biophys J. 77: 617-628.

Fischbach GD and Cohen SA. (1973) The distribution of acetylcholine sensitivity over uninnervated and innervated muscle fibers grown in cell culture. Dev Biol. 31: 147-162.

Fischbach GD. (1972) Synapse formation between dissociated nerve and muscle cells in low density cell cultures. Dev Biol. 28: 407-429.

Fisher OZ, et al. (2010) Bioinspired materials for controlling stem cell fate. Ace Chem Res. 43: 419-428.

Fishman RA. (2002) The cerebrospinal fluid production rate is reduced in dementia of the Alzheimer's type. Neurology. 58: 1866; author reply 1866.

Flucher BE, et al. (1990) Localization of the alpha 1 and alpha 2 subunits of the dihydropyridine receptor and ankyrin in skeletal muscle triads. Neuron. 5:339-351.

Flucher BE, et al. (1991) Biogenesis of transverse tubules in skeletal muscle in vitro. Dev Biol. 145: 77-90.

Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.

Flucher BE, et al. (1994) Molecular organization of transverse tubule sarcoplasmic reticulum junctions during development of excitationcontraction coupling in skeletal muscle. Mol Biol Cell. 5: 1105-1118.

Forry SP, et al. (2006) Facilitating the culture of mammalian nerve cells with polyelectrolyte multilayers. Langmuir. 22: 5770-5775.

(56) References Cited

OTHER PUBLICATIONS

Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.
Fowler VM, et al. (1993) Tropomodulin is associated with the free (pointed) ends of the thin filaments in rat skeletal muscle. J Cell Biol. 120: 411-420.
Fox MA, et al. (2007) Distinct target-derived signals orgamze formation, maturation, and maintenance of motor nerve terminals. Cell. 129: 179-193.
Francis PT. (2008) Glutamatergic approaches to the treatment of cognitive and behavioural symptoms of Alzheimer's disease. Neurodegener Dis. 5: 241-243.
Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.
Franzini-Armstrong C and Protasi F. (1997) Ryanodine receptors of striated muscles: a complex channel capable of multiple interactions. Physiol Rev. 77: 699-729.
Friedman B, et al. (1995) BDNF and NT-4/5 exert neurotrophic influences on injured adult spinal motor neurons. J Neurosci. 15: 1044-1056.
Fu X, et al. (1995) Acidic fibroblast growth factor reduces rat skeletal muscle damage caused by ischemia and reperfusion. Chin Med J (Engl). 108: 209-214.
Fuentes-Medel Y, et al. (2012) Integration of a retrograde signal during synapse formation by glia-secreted TGF-B ligand. Curr Biol. 22: 1831-1838.
Funakoshi H, et al. (1995) Muscle-derived neurotrophin-4 as an activitydependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175:50-57.
Galizia CG and Menzel R. (2000) Probing the olfactory code. Nat Neurosci. 3: 853-854.
Gao BX and Ziskind-Conhaim L. (1995) Development of glycine- and GABAgated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69:4027-4037.
Gaud A, et al. (2004) Prednisone reduces muscle degeneration in dystrophindeficient Caenorhabditis elegans. Neuromuscul Disord. 14: 365-370.
Gaztañaga, L., Marchlinski, F. E., & Betensky, B. P. (2012). Mechanisms of cardiac arrhythmias. Revista Española de Cardiología (English Edition), 65(2), 174-185.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.

Ghiani CA, et al. (1999) Neurotransmitter receptor activation triggers p27(Kipl) and p21(CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass Land Kauffman SA. (1973) The logical analysis of continuous, non-linear biochemical control networks. J Theor Biol. 39: 103-129.
Glass L. ( 197 5) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83:2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374:1745-175.
Guettier-Sigrist S, et al. (1998) Muscle could be the therapeutic target in SMA treatment. J Neurosci Res. 53: 663-669.
Guettier-Sigrist S. et al. (2000) Cell types required to efficiently innervate human muscle cells in vitro. Exp Cell Res. 259: 204-212.

(56) References Cited

OTHER PUBLICATIONS

Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in App+ PSI transgenic mice. Neurobiol Dis. 15: 188-195.
Haas HL and Selbach 0. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly( ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U s A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.

Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey N, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients withatorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. (1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 177 5-1778.
Hoffmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffinan P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-29.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRiaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alpha1A-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.

(56) References Cited

OTHER PUBLICATIONS

Hughes B. (2008) 2007 FDA drug approvals: a year of flux. Nat Rev Drug Discov. 7: 107-109.

Huh D, et al. (2010) Reconstituting organ-level lung functions on a chip. Science. 328: 1662-1668.

Huh D, et al. (2012) Microengineered physiological biomimicry: organs-onchips. Lab Chip. 12: 2156-2164.

Hui EE and Bhatia SN. (2007) Microscale control of cell contact and spacing via three-component surface patterning. Langmuir. 23: 4103-4107.

Hung SC, et al. (2002) In vitro differentiation of size-sieved stem cells into electrically active neural cells. Stem Cells. 20: 522-529.

Husmann I, et al. (1996) Growth factors in skeletal muscle regeneration. Cytokine Growth Factor Rev. 7: 249-258.

Huxley, A. F. (1975). The origin of force in skeletal muscle. Ciba Found Symp. 31: 271-290.

Ichikawa H, et al. (2004) Effect of Bm-3a deficiency on parvalbumin-immunoreactive primary sensory neurons in the dorsal root ganglion. Brain Res Dev Brain Res. 150: 41-45.

Inoue N, et al. (2004) Rapid electrical stimulation of contraction modulates gap junction protein m neonatal rat cultured cardiomyocytes: involvement of mitogen-activated protein kinases and effects of angiotensin II-receptor antagonist. J Am Coll Cardiol. 44: 914-922.

Iravanian S, et al. (2003) Functional reentry in cultured monolayers of neonatal rat cardiac cells. Am J Physiol Heart Circ Physiol. 285: H449-H456.

Ito Y. (1999) Surface micropatterning to regulate cell functions. Biomaterials. 20:2333-2342.

Izrael M, et al. (2007) Human oligodendrocytes derived from embryonic stem cells: Effect of noggin on phenotypic differentiation in vitro and on myelination in vivo. Mol Cell Neurosci. 34: 310-323.

Izumiya Y, et al. (2008) Fast/glycolytic muscle fiber growth reduces fat mass and improves metabolic parameters in obese mice. Cell Metabolism. 7: 159-172.

Jackson JH 4th, et al. (2004) Assessment of drug therapy management and the prevalence of heart failure in a managed care population with hypertension. J Manag Care Pharm. 10: 513-520.

Jaworska-Wilczynska M, et al. (2002) Three lipoprotein receptors and cholesterol in inclusion-body myositis muscle. Neurology. 58: 438-445.

Jensen J, et al. (2009) Human embryonic stem cell technologies and drug discovery. J Cell Physiol. 219: 513-519.

Jessen KR and Mirsky R. (2005) The origin and development of glial cells in peripheral nerves. Nat Rev Neurosci. 6: 671-682.

Jevsek M, et al. (2004) Origin of acetylcholinesterase in the neuromuscular junction formed in the in vitro innervated human muscle. Eur J Neurosci. 20:2865-2871.

Jhamandas JH, et al. (2001) Cellular mechanisms for amyloid beta-protein activation of rat cholinergic basal forebrain neurons. J Neurophysiol. 86: 1312-1320.

Jiang XH, et al. (2009) Isolation and characterization of neural crest stem cells derived from in vitro-differentiated human embryonic stem cells. Stem Cells Dev. 18: 1059-1070.

Jiang Z and Clemens PR. (2006) Cellular caspase-8-like inhibitory protein (cFLIP) prevents inhibition of muscle cell differentiation induced by cancer cells. FASEB J. 20: 2570-2572.

Jiang ZG, et al. (1990) Excitatory and inhibitory transmission from dorsal root afferents to neonate rat motoneurons in vitro. Brain Res. 535: 110-118.

Jin P, et al. (1991) Recombinant platelet-derived growth factor-BB stimulates growth and inhibits differentiation of rat L6 myoblasts. J Biol Chem. 266: 1245-1249.

Johnson TE, et al. (2005) Statins and PP ARalpha agonists induce myotoxicity in differentiated rat skeletal muscle cultures but do not exhibit synergy with cotreatment. Toxicol Appl Pharmacol. 208: 210-221.

Julius D and Basbaum AI. (2001) Molecular mechanisms of nociception. Nature. 413: 203-210.

Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.

Jung DR, et al. (2001) Topographical and physicochemical modification of material surface to enable patterning of living cells. Crit Rev Biotechnol. 21: 111-154.

Jurdana M, et al. (2009) Neural agrin changes the electrical properties of developing human skeletal muscle cells. Cell Mol Neurobiol. 29: 123-131.

Kaeberlein M. (2009) Spermidine surprise for a long life. Nat Cell Biol. 11:1277-1278.

Kaji H, et al. (2003) Pharmacological characterization of micropatterned cardiac myocytes. Biomaterials. 24: 4239-4244.

Kamp TJ. (2009) Human pluripotent stem cell-derived cardiomyocytes for safety pharmacology applications. Journal of Pharmacological and Toxicological Methods. 60: 259.

Kane RS, et al. (1999) Patterning proteins and cells using soft lithography. Biomaterials. 20: 2363-2376.

Kang JH, et al. (2009) In vitro 3D model for human vascularized adipose tissue. Tissue Eng Part A. 15: 2227-2236.

Kato AC and Lindsay RM. (1994) Overlapping and additive effects of neurotrophins and CNTF on cultured human spinal cord neurons. Exp Neurol. 130: 196-20.

Katsuki H, et al. (2000) Distinct signaling pathways involved in multiple effects of basic fibroblast growth factor on cultured rat hippocampal neurons. Brain Res. 885: 240-250.

Katz LC and Shatz CJ. (1996) Synaptic activity and the construction of cortical circuits. 274: 1133-1138.

Kauffman S, et al. (2003) Random Boolean network models and the yeast transcriptional network. Proc Natl Acad Sci US A. 100: 14796-14799.

Kauffman S. (1971) Gene regulation networks: a theory for their global structure and behaviors. Curr Top Dev Biol. 6: 145-182.

Kaufinann P, et al. (2006) Toxicity of statins on rat skeletal muscle mitochondria. Cell Mol Life Sci. 63: 2415-2425.

Keefer EW, et al. (2001a) Acute toxicity screening of novel AChE inhibitors using neuronal networks on microelectrode arrays. Neurotoxicology. 22: 3-1.

Keefer EW, et al. (2001b) Characterization of acute neurotoxic effects of trimethylolpropane phosphate via neuronal network biosensors. Biosens Bioelectron. 16: 513-525.

Kessaris N, et al. (2008) Specification of CNS glia from neural stem cells in the embryonic neuroepithelium. Philos Trans R Soc Lond B Biol Sci. 363: 71-85.

Khademhosseini A, et al. (2006a) Interplay of biomaterials and micro-scale technologies for advancing biomedical applications. J Biomater Sci Polym Ed. 17: 1221-1240.

Khademhosseini A, et al. (2006b) Microscale technologies for tissue engineering and biology. Proc Natl Acad Sci USA. 103: 2480-2487.

Khorchid A, et al. (1999) Characterization of the signal transduction pathways mediating noradrenaline-stimulated MAPK activation and c-fos expression in oligodendrocyte progenitors. JNeurosci Res. 58: 765-778.

Khorchid A, et al. (2002) Developmental regulation of alpha IA-adrenoceptor function in rat brain oligodendrocyte cultures. Neuropharmacology. 42: 685-696.

Kidambi S, et al. (2004) Controlling primary hepatocyte adhesion and spreading on protein-free polyelectrolyte multilayer films. J Am Chem Soc. 126: 16286-16287.

Kidambi S, et al. (2007a) Patterned co-culture of primary hepatocytes and fibroblasts using polyelectrolyte multilayer templates. Macromol Biosci. 7: 344-353.

Kidambi S, et al. (2007b) Cell adhesion on polyelectrolyte multilayer coated polydimethylsiloxane surfaces with varying topographies. Tissue Eng. 13: 2105-2117.

Kidd, J. (2006). Life after statin patent expiries. Nat Rev Drug Discov. 5: 813-814.

Kim C, et al. (2010) Non-cardiomyocytes influence the electrophysiological maturation of human embryonic stem cell-derived cardiomyocytes during differentiation. Stem Cells Dev. 19: 783-795.

Kim D-H, et al. (2005) Modulation of adhesion and growth of cardiac myocytes by surface nanotopography. Proceedings fo the

(56) References Cited

OTHER PUBLICATIONS

2005 IEEE. Engineering in Medicine and Biology 27th Annual Conference. Shanghai, China, Sep. 1-4, 2005.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
Kim, Jinseok, et al. "Biohybrid microsystems actuated by cardiomyocytes: microcantilever, microrobot, and micropump." Robotics and Automation, 2008. ICRA 2008. IEEE International Conference on. IEEE, 2008.
King T, et al. (2000) Piezoactuators for 'real-world' applications—Can they deliver sufficient displacement? Power Engineering. 14: 105-110.
Kingshott P And Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable h ESC lines for fluorescent tracking and drug resistance selection of cardiomyocytes. PLoS One. 4: e5046.
Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Klein WL. (2002) Abeta toxicity in Alzheimer's disease: globular oligomers (ADDLs) as new vaccine and drug targets. Neurochem Int. 41: 345-352.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.
Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.
Kobayashi T, et al. (1987) Human muscle cultured in monolayer and cocultured with fetal rat spinal cord: importance of dorsal root ganglia for achieving successful functional innervation. JNeurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal A511. growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J and Walro J. (1992) Axotomy induces fusimotor-free muscle spindles in neonatal rats. Neurosci Lett. 136: 216-218.
Kucera J, et al. (1989) Role of nerve and muscle factors in the development of rat muscle spindles. Am J Anat. 186: 144-160.

Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of A518. skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kumar S, et al. (1998) NT-3-mediated TrkC receptor activation promotes proliferation and cell survival of rodent progenitor oligodendrocyte cells in vitro and in vivo. J Neurosci Res. 54: 754-765.
Kurek JB, et al. (1996) Leukemia inhibitory factor and interleukin-6 are produced by diseased and regenerating skeletal muscle. Muscle Nerve. 19: 1291-1301.
Lacor PN, et al. (2007) Abeta oligomer-induced aberrations m synapse composition, shape, and density provide a molecular basis for loss of connectivity in Alzheimer's disease. J Neurosci. 27: 796-807.
Lacor PN. (2007) Advances on the understanding of the origins of synaptic pathology in AD. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abeta1-42 are potent central nervous system neurotoxins. Proc Natl Acad Sci US A. 95:6448-6453.
Lambeth MJ and Kushmerick MJ. (2002) A computational model for glycogenolvsis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer Rand Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.

(56) References Cited

OTHER PUBLICATIONS

Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-I (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5 Proc Natl Acad Sci US A. 98: 12742-12747.
Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci U S A. 102: 701-706.
Lochter AJ, et al. (1995) Control of neuronal morphology in vitro: interplay between adhesive substrate forces and molecular instruction. J Neurosci Res. 42:145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Lou XJ. (2009) Statistical switching kinetics of ferroelectrics. J Phys Condens Matter. 21(1):012207.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit IC.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-50.
Malerba A, et al. (2009) Selection of multipotent cells and enhanced muscle reconstruction by myogenic macrophage-secreted factors. Exp Cell Res. 315:915-927.
Malm C, et al. (2004) Leukocytes, cytokines, growth factors and hormones in human skeletal muscle and blood after uphill or downhill running. J Physiol. 556:983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.

(56) References Cited

OTHER PUBLICATIONS

Masu Y, et al. (1993) Disruption of the CNTF gene results in motor neuron degeneration. Nature. 365: 27-32.

Matsakas A and Patel K. (2009) Skeletal muscle fibre plasticity in response to selected environmental and physiological stimuli. Histol Histopathol. 24: 611-629.

Matsuda T, et al. (1992) Two-dimensional cell manipulation technology. An artificial neural circuit based on surface microphotoprocessing. ASAIO J. 38:M243-M247.

Matthews PB. (1964) Muscle spindles and their motor control. Physiol Rev. 44:219-288.

Mattson MP, et al. (1992) Beta-Amyloid Peptides Destabilize Calcium Homeostasis and Render Human Cortical-Neurons Vulnerable to Excitotoxicity. J Neurosci. 12: 376-389.

Matzno S, et al. (2003) Evaluation of the synergistic adverse effects of concomitant therapy with statins and fibrates on rhabdomyolysis. J Pharm Pharmacol. 55: 795-802.

Maves L, et al. (2007) Pbx homeodomain proteins direct Myod activity to promote fast-muscle differentiation. Development. 134: 3371-3382.

Maynard EM. (2001) Visual prostheses. Annu Rev Biomed Eng. 3: 145-168.

McAuliffe GJ, et al. (2008) Development of a gastrointestinal tract microscale cell culture analog to predict drug transport. Mol Cell Biomech. 5: 119-132.

McBeath R, et al. (2004) Cell shape, cytoskeletal tension, and RhoA regulate stem cell lineage commitment. Dev Cell. 6: 483-495.

McDevitt TC, et al. (2002) In vitro generation of differentiated cardiac myofibers on micropatterned laminin surfaces. J Biomed Mater Res. 60: 472-479.

McMahon JA, et al. (1998) Noggin-mediated antagonism of BMP signaling is required for growth and patterning of the neural tube and somite. Genes Dev. 12:1438-1452.

Megeney LA, et al. (1996) bFGF and LIF signaling activates STAT3 in proliferating myoblasts. Dev Genet. 19: 139-145.

Mehra S, et al. (2004) A boolean algorithm for reconstructing the structure of regulatory networks. Metab Eng. 6: 326-339.

Meijer L and Raymond E. (2003) Roscovitine and other purines as kinase inhibitors. From starfish oocytes to clinical trials. Ace Chem Res. 36: 417-425.

Melendez-Vasquez CV, et al. (2001) Nodes of Ranvier form in association with ezrin-radixin-moesin (ERM)-positive Schwann cell processes. Proc Natl Acad Sci US A. 98: 1235-1240.

Mendelsohn JD, et al. (2003) Rational design of cytophilic and cytophobic polyelectrolyte multilayer thin films. Biomacromolecules. 2003 4: 96-106.

Menendez L, et al. (2011) Wnt signaling and a Smad pathway blockade direct the differentiation of human pluripotent stem cells to multipotent neural crest cells. Proc Natl Acad Sci US A. 108: 19240-19245.

Menn B, et al. (2010) Delayed treatment with systemic (S)-roscovitine provides neuroprotection and inhibits in vivo CDK5 activity increase in animal stroke models. PLoS One. 5: e1211.

Metzger SW, et al. (1999) Development and characterization of surface chemistries for microfabricated biosensors. J of Vacuum Sci & Tech a-Vacuum Surfaces and Films. 17: 2623-2628.

Meyer G and Nabil MA. (1988) Novel optical approach to atomic force microscopy. Applied Physics Letters. 53: 1045-1047.

Meyer T, et al. (2004) Micro-electrode arrays in cardiac safety pharmacology—A novel tool to study QT interval prolongation. Drug Saf. 27: 763-772.

Meyer T, et al. (2004b) QT-screen: high-throughput cardiac safety pharmacology by extracellular electrophysiology on primary cardiac myocytes. Assay Drug Dev Technol. 2: 507-514.

Miles GB, et al. (2004) Functional properties of motoneurons derived from mouse embryonic stem cells. J Neurosci. 24: 7848-7858.

Miller FD. (2007) Riding the waves: neural and nonneural ongms for mesenchymal stem cells. Cell Stem Cell. 1: 129-130.

Miller SC, et al. (1988) Tumor necrosis factor inhibits human myogenesis in vitro. Mol Cell Biol. 8: 2295-2301.

Mitsumoto H, et al. (2001) Effects of cardiotrophin-1 (CT-1) in a mouse motor neuron disease. Muscle Nerve. 24: 769-777.

Mizuseki K, et al. (2003) Generation of neural crest-derived peripheral neurons and floor plate cells from mouse and primate embryonic stem cells. Proc Natl Acad Sci US A. 100: 5828-5833.

Moe GK. (1962) On the multiple wavelet hypothesis of atrial fibrillation. Arch Int Pharmacodyn Ther. 183-188.

Mohammed JS, et al. (2004) Micropatteming of nanoengineered surfaces to study neuronal cell attachment in vitro. Biomacromolecules. 5: 1745-1755.

Mohan DK, et al. (2006) Toxin detection based on action potential shape analysis using a realistic mathematical model of differentiated NG 108-15 cells. Biosens Bioelectron. 21: 1804-1811.

Mokry J, et al. (2007) Differentiation of neural stem cells into cells of oligodendroglial lineage. Acta Medica (Hradec Kralove). 50: 35-41.

Molnar P, et al. (2007) Photolithographic Patterning of C2C12 Myotubes using Vitronectin as Growth Substrate in Serum-Free Medium. Biotechnol Prog. 23:265-268.

Molnar P, et al. (2007b) Synaptic connectivity in engineered neuronal networks. Methods Mol Biol. 403: 165-173.

Molnar P, et al. (2007c) Modeling of action potential generation in NG 108-15 cells. Methods Mol Biol. 403: 175-184.

Monaco EA 3rd and Vallano ML. (2005) Roscovitine triggers excitotoxicity in cultured granule neurons by enhancing glutamate release. Mol Pharmacol. 68:1331-1342.

Monaco EA 3rd. (2004) Recent evidence regarding a role for Cdk5 dysregulation in Alzheimer's disease. Curr Alzheimer Res. 1: 33-38.

Monyer H, et al. (1994) Developmental and regional expression in the rat brain and functional properties of four NMDA receptors. Neuron. 12: 529-540.

Moore JW, et al. (1991) The mRNAs encoding acidic FGF, basic FGF and FGF receptor are coordinately downregulated during myogemc differentiation. Development. 111: 741-748.

Morefield SI, et al. (2000) Drug evaluations using neuronal networks cultured on microelectrode arrays. Biosens Bioelectron. 15: 383-396.

Morimoto, S., & Masuda, M. (1984). Dependence of conduction velocity on spike interval during voluntary muscular contraction in human motor units. European journal of applied physiology and occupational physiology, 53(3), 191-195.

Morin F, et al. (2006) Constraining the connectivity of neuronal networks cultured on microelectrode arrays with microfluidic techniques: a step towards neuron-based functional chips. Biosens Bioelectron. 21: 1093-1100.

Morrow NG, et al. (1990) Increased expression of fibroblast growth factors in a rabbit skeletal muscle model of exercise conditioning. J Clin Invest. 85: 1816-1820.

Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.

Moulard G, et al. (1998) Improvement of the cantilever beam technique for stress measurement during the physical vapor deposition process. J Vac Science Technol A. 16(2): 736-742.

Mousavi K, et al. (2004) BDNF rescues myosin heavy chain IIB muscle fibers after neonatal nerve injury. Am J Physiol Cell Physiol. 287: C22-C29.

Mrksich M. (2000) A surface chemistry approach to studying cell adhesion. Biosensors & Bioelectronics. 29: 267-273.

Mufti NA and Shuler ML. (1998) Different In Vitro Systems Affect CYPIAI Activity in Response to 2,3,7,8-Tetrachlorodibenzo-p-dioxin. Toxicol In Vitro. 12: 259-272.

Mulkey D, et al. (2003) Hyperbaric oxygen and chemical oxidants stimulate $CO_2/H+$-sensitive neurons in rat brain stem slices. J Appl Physiol. 95: 910-92.

Mullen RJ, et al. (1992) NeuN, a neuronal specific nuclear protein in vertebrates. Development. 116: 201-211.

Muller FJ, et al. (2006) Gene therapy: can neural stem cells deliver? Nat Rev Neurosci. 7: 75-84.

(56) References Cited

OTHER PUBLICATIONS

Muller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481:617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan To Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2006) Evidence for multiple mechanisms in human ventricular fibrillation. Circulation. 114: 536-542.
Nash, M. P., & Panfilov, A. V. (2004). Electromechanical model of excitable tissue to study reentrant cardiac arrhythmias. Progress in biophysics and molecular biology, 85(2), 501-522.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32:4267-4274.
Natarajan A, et al. (2013) Engineered In Vitro Feed-Forward Networks. J Biotechnol Biomater. 3:153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24:1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(1-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nugaeva, N, et al. (2005). Micromechanical cantilever array sensors for selective fungal immobilization and fast growth detection. Biosensors and Bioelectronics, 21(6), 849-856.
Nyitrai G, et al. (2006) Extracellular level of GABA and Glu: III Vivo microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helixloop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.

(56) References Cited

OTHER PUBLICATIONS

Orentas DM and Miller RH. (1998) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Park, TH et al. (2003) Integration of Cell Culture and Microfabrication Technology. Biotechnol. Prog. 19: 243-253.
Parker KK, et al. (2008) Myofibrillar architecture m engineered cardiac myocytes. Circ Res. 103: 340-342.
Pamg C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23:5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci USA. 101: 12543-12548.
Peters A. (1964) Observations on the Connexions Between A709. Myelin Sheaths and Glial Cells in the Optic Nerves of Young Rats. J Anat. 98: 125-134.
Peterson CA, et al. (1999) Effects of moisture on Fowler-Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3:215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90:1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and Mc Morris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B-Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly( ethylene glycol) Photolithography to Create High-Density Cell Arrays on Glass. Langmuir. 19:9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.

(56) References Cited

OTHER PUBLICATIONS

Richert L, et al. (2004) pH dependent growth of poly (L-lysine )/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation m apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci USA. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-I. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sandi E, et al. (2008) Neural agrin controls maturation of the excitation-contraction coupling mechanism in human myotubes developing in vitro. Am J Physiol, Cell Physiol. 294(1):C66-73.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. ( 1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-64.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-11.
Scherer J, et al. (1995) Differentiation and maturation of rabbit retinal oligodendrocyte precursor cells in vitro. Brain Res Dev Brain Res. 89: 214-226.

Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276:C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster Rand Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12:1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.

(56) References Cited

OTHER PUBLICATIONS

Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor beta1a subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14:1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19:317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313:107-1.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-172.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.
Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2005) Molecular biology and genetics of Alzheimer's disease.CR Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 7.
Stenger DA, et al. (1992) Coplanar Molecular Assemblies of Aminoalkylsilane and Perfluorinated Alkylsilane-Characterization and Geometric Definition of Mammalian-Cell Adhesion and Growth. Journal of the American Chemical Society. 114: 8435-8442.
Stenger DA, et al. (1993) Surface determinants of neuronal survival and growth on self-assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.

(56) References Cited

OTHER PUBLICATIONS

Swasdison Sand Mayne R. (1992) Formation of highly organized skeletal muscle fibers in vitro. Comparison with muscle development in vivo. J Cell Sci. 102:643-652.
Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. JN eurosci Res. 85: 4 7-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-9.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J.

Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu A Y. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-20.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
Van de Ven C, et al. (2007) The potential of umbilical cord blood multipotent stem cells for non hematopoietic tissue and cell regeneration. Exp Hematol. 35:1753-1765.
Van der Valk J, et al. (2010) Optimization of chemically defined cell culture media-replacing fetal bovine serum in mammalian in vitro methods. Toxicol In Vitro. 24: 1053-1063.
Van Rijen HV, et al. (2006) Connexins and cardiac arrhythmias. Adv Cardiol. 42:150-160.
Van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue A888. culture: Effects on skeletal muscle organogenesis. In Vitro Cell Dev Biol. 24:609-619.
Varghese K, et al. (2009) Regeneration and characterization of adult mouse A889. hippocampal neurons in a defined in vitro system. J N eurosci Methods. 177: 51-59.
Varghese K, et al. (2010) A new target for amyloid beta toxicity validated by standard and high-throughput electrophysiologv. PLoS One. 5: e8643.
Vargo TG, et al. (1992) Monolayer Chemical Lithography and Characterization of Fluoropolymer Films. Langmuir. 8: 130-1.
Vartanian T, et al. (1988) Oligodendrocyte substratum adhesion modulates expression of adenylate cyclase-linked receptors. Proc Natl Acad Sci US A. 85:939-943.
Ventimiglia R, et a. (1987) Localization of beta-adrenergic receptors on differentiated cells of the central nervous system in culture. Proc Natl Acad Sci USA. 84: 5073-507.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.

(56) References Cited

OTHER PUBLICATIONS

Vogel V and Sheetz M. (2006) Local force and geometry sensing regulate cell functions. Nat Rev Mol Cell Biol. 7: 265-275.
Vogel Zand Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS. and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J N eurochem. 101: 1172-1184.
Walsh K, et al. (2005) Human central nervous system tissue culture: a historical review and examination ofrecent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and A907. ciliary neurotrophic factor on the proliferation and differentiation of adult human myoblasts. Cell Mol Neurobiol. 28: 113-124.
Ward JH, et al. (2001) Micropatteming of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacal. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122:R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation ofmyelination by Schwann cells. Ann NY Acad Sci. 605: 1-14.
Wright CD, et al. (2008) Nuclear alphal-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity m functional mammalian neuronal networks grown on patterned surfaces. J Neurosci Methods. 117: 123-131.
Xi J, et al. (2005) Self-assembled microdevices driven by muscle. Nat Mater. 4:180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26:93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-33.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly( diol citrate) biodegradable elastomers. Biomaterials. 27: 1889-1898.
Yang L, et al. (2007) Increased asynchronous release and aberrant calcium channel activation m amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatteming capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.

(56) References Cited

OTHER PUBLICATIONS

Yap FL and Zhang Y. (2007) Protein and cell micropatterning and its integration with micro/nanoparticles assembly. Biosens Bioelectron. 22: 775-788.

Yasuda SI, et al. (2001) A novel method to study contraction characteristics of a single cardiac myocyte using carbon fibers. Am J Physiol Heart Circ Physiol. 281: H1442-H1446.

Yeung CK, et al. (2007) Drug profiling using planar microelectrode arrays. Anal Bioanal Chem. 387: 2673-2680.

Yin SH, et al. (2005) Measuring single cardiac myocyte contractile force via moving a magnetic bead. Biophys J. 88: 1489-1495.

Zhao BL, et al. (1989) Scavenging effect of extracts of green tea and natural antioxidants on active oxygen radicals. Cell Biophys. 14: 175-185.

Zhou L, et al. (2005) Mechanistic model of cardiac energy metabolism predicts localization of glycolysis to cytosolic subdomain during ischemia. Am J Physiol Heart Circ Physiol. 288: H2400-H2411.

Zhou Z, et al. (1999) Block of HERG potassium channels by the antihistamine astemizole and its metabolites desmethylastemizole and norastemizole. J Cardiovasc Electrophysiol. 10: 836-843.

Zimmermann WH, et al. (2000) Three-dimensional engineered heart tissue from neonatal rat cardiac myocytes. Biotechnol Bioeng. 68: 106-114.

Zimmermann WH, et al. (2002) Tissue Engineering of a Differentiated Cardiac Muscle Construct. Circ Res. 90: 223-230.

Zorzano A, et al. (2003) Intracellular signals involved in the effects of insulin-A957. like growth factors and neuregulins on myofibre formation. Cell Signal. 15: 141-149.

Zurn AD, et al. (1996) Combined effects of GDNF, BDNF, and CNTF on motoneuron differentiation in vitro. J Neurosci Res. 44: 133-141.

Zweigerdt R, et al. (2003) Generation of confluent cardiomyocyte monolayers derived from embryonic stem cells in suspension: a cell source for new therapies and screening strategies. Cytotherapy. 5: 399-413.

Co-Pending U.S. Appl. No. 14/422,082, filed Feb. 17, 2015.
Co-Pending U.S. Appl. No. 14/764,683, filed Jul. 30, 2015.
Co-Pending U.S. Appl. No. 15/190,958, filed Jun. 23, 2016.
Kim, IEEE Poster Micropatterning of Cardiomyocytes using adhesion-resistant polymeric microstructions, International Conf on Solid-State Sensors Kores Jun. 5-6, 2005.

Natarajan et al, Patterned Cardiomyocytes on Microelectrode Arrays for High-Throughput Functional Side Effect Screening with Enhanced Information Content, Oct. 21-23, 2008.

Advisory Action issued in U.S. Appl. No. 15/190,958, dated May 18, 2020.

Advisory Action issued in U.S. Appl. No. 14/764,683, dated Apr. 13, 2020.

\* cited by examiner

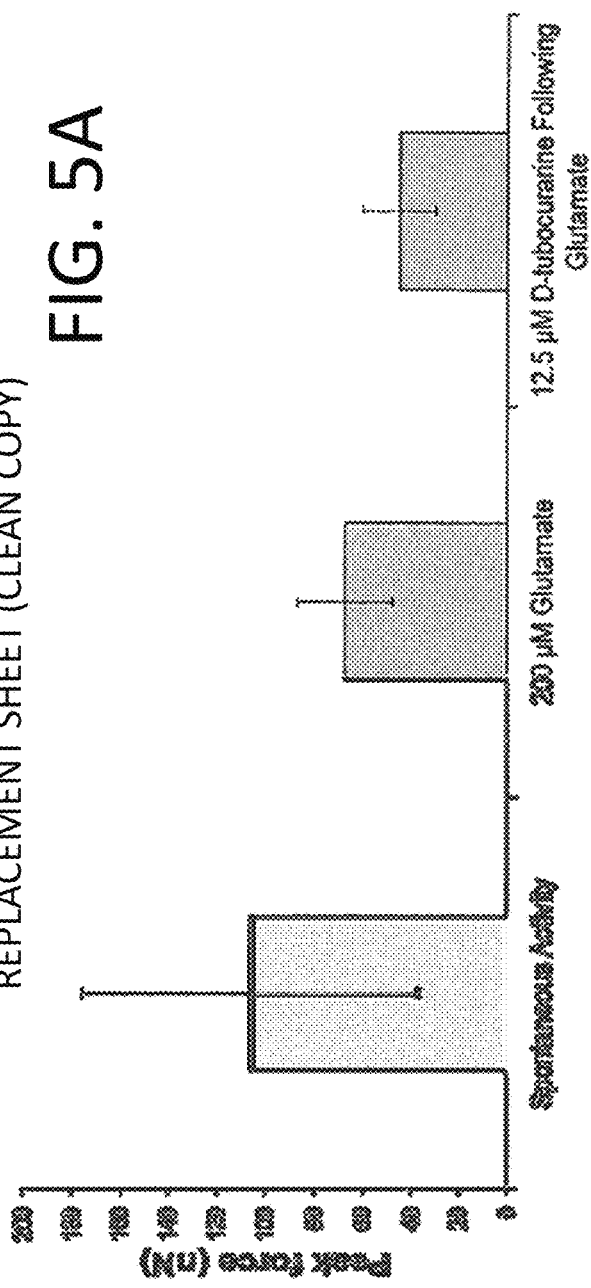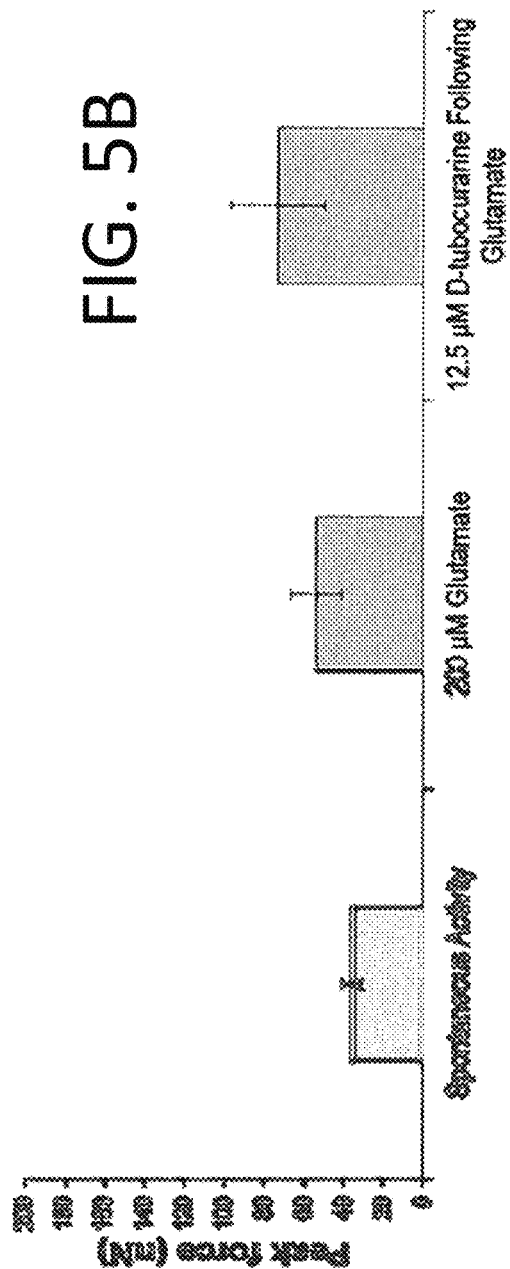

DEVICES AND METHODS COMPRISING NEUROMUSCULAR JUNCTIONS

CROSS-REFERENCE TO RELATED APPLICATIONS

This application claims the benefit of U.S. Provisional Patent Application No. 62/034,217, filed on Aug. 7, 2014, entitled "DEVICES AND METHODS COMPRISING NEUROMUSCULAR JUNCTIONS," the disclosure of which is expressly incorporated herein by reference in its entirety.

STATEMENT REGARDING FEDERALLY SPONSORED RESEARCH

This invention was made with Government support under agency contract/grant number R01-NS050452 and EB009429 awarded by the National Institutes of Health. The United States government has certain rights in the invention.

BACKGROUND

The ability to measure and record physiologically relevant, functional outputs from neuromuscular synaptic contacts in vitro is necessary for the study of peripheral nervous system diseases and disorders such as neuropathies (e.g., Amyotrophic Lateral Sclerosis (ALS)) and muscle wasting conditions (e.g., muscular dystrophy and sarcopenia).

However, there is a scarcity of devices and methods that afford the skilled person with an opportunity to examine neuromuscular transmission in vitro. These needs and other needs are satisfied by the compositions and methods disclosed herein.

SUMMARY

Disclosed herein is a device, comprising a plurality of cantilevers, at least two of the plurality of cantilevers comprising one or more neuromuscular junctions formed by a co-culture of myotubes and motoneurons; and an automated detection system configured to detect a deflection of one or more of the plurality of cantilevers.

Disclosed herein is an in vitro device, comprising at least one cantilever comprising a co-culture of myotubes and motoneurons forming at least one neuromuscular junction; and a detection system configured to detect a movement the at least one cantilever. In some aspects, the detection system is automated.

In some aspects, the detection system can include a laser and a photo-detector. In some aspects, the detection system includes a plurality of linear actuators attached to XY translational stages that control the position of the laser and photo-detector. In some aspects, each of the cantilevers includes one or more piezoelectric materials (e.g., quartz, bone, sodium tungstate, zinc oxide, or lead zirconate titante). In some aspects, one or more of the cantilevers can be surface-modified or surface-coated. In some aspects, the cantilever can have a (3-Trimethoxysilyl propyl) diethylenetriamine (DETA) surface modification. The detection system can optionally include a transducer for detecting a change in electrical conductivity of the cantilever. The detection system can also include a digitizer and a computer, wherein the photo-detector is in communication with the digitizer and wherein the digitizer is in communication with the computer.

In some aspects, the devices can include a temperature-controlled stage. Each of the cantilevers can be maintained on the temperature-controlled stage. The temperature-controlled stage can include one or more electrodes and one or more pulse generators. In some aspects, the detection system can also include a digitizer and a computer. The one or more pulse generators can be in communication with the digitizer, and wherein the digitizer is in communication with the computer.

In some aspects, muscle cells or myblast fuse together to form the myotubes. In some aspects, the myotubes are human or rat myotubes. In some aspects, the motoneurons are human or rat motoneurons. In some aspects, at least one of the myotubes or motoneurons is obtained from a subject diagnosed with or suspected of having a muscle wasting condition, a peripheral neuropathy, or both. The co-culture of myotubes or motoneurons can be maintained in a serum-free medium.

In some aspects, the devices can include a first chamber including the plurality of cantilevers (or the at least one cantilever) and the myotubes, and second chamber that is spaced apart from the first chamber and including the motoneurons. One or more axons extend from the motoneurons toward the first chamber. In some aspects, the second chamber includes a plurality of electrodes in contact with the motoneurons. In some aspects, the plurality of electrodes take the form of a microelectrode array.

In some aspects, the devices can include at least one guide configured to route the one or more axons extending from the motoneurons toward the first chamber. In some aspects, the devices can include a barrier arranged between the first chamber and the second chamber. The guide can include one or more channels that are formed through the barrier. The barrier may be made of a polydimethylsiloxane material. In some aspects, the guide can include patterned extracellular matrix molecules, chemotactic features, or a combination thereof.

Disclosed herein is a method of screening for an agent that affects neuromuscular transmission, comprising (i) recording data from a device comprising a plurality of cantilevers, at least two of the cantilevers comprising a co-culture of myotubes and motoneurons forming at least one functional neuromuscular junction; and an automated detection system comprising a laser and a photo-detector; (ii) contacting one or more agents with the at least one functional neuromuscular junction; and (iii) recording data generated using the device; wherein a change in the data obtained in step (iii) when compared to the data obtained in step (i) indicates that the one or more agents affects neuromuscular transmission.

In some aspects of the method, recording data can include measuring a change in reflection angle of the laser. Measuring a change in reflection angle of the laser includes scanning a laser across a tip of each of the plurality of cantilevers. A change in reflection angle of the laser indicates a change in the position of a cantilever. In some aspects of the method, recording data can include measuring a change in resistance or electrical conductivity of a cantilever. The methods disclosed herein can also include using the change in reflection angle of the laser to determine myotube force, a change in the electrical conductivity to determine myotube force, or both.

In some aspects of the methods, a step may be included for confirming the structural integrity of the myotubes. Confirming the structural integrity of the myotubes can include applying electrical stimulation to the co-culture of myotubes and motoneurons.

The one or more agents used in the methods disclosed herein can include a metabolic inhibitor, a nutritional supplement, a therapeutic compound, a therapeutic composition, a therapeutic drug, an investigational compound, an investigational composition, and an investigational drug, a biosimilar, an agonist, an antagonist, a hormone, a growth factor, a small molecule, a monoclonal antibody, and a combination thereof. At least one of the myotubes or motoneurons can be obtained from a subject diagnosed with or suspected of having a muscle wasting condition, a peripheral neuropathy, or both.

Disclosed herein is a method of screening for an agent that affects neuromuscular transmission, comprising (i) recording data from a device comprising a plurality of cantilevers, at least two of the plurality of cantilevers comprising a co-culture of myotubes and motoneurons forming at least one functional neuromuscular junction; and an automated detection system comprising (i) a laser and a photo-detector and (ii) a transducer for detecting a change in electrical conductivity; (ii) contacting one or more agents with the at least one functional neuromuscular junction; and (iii) recording data generated using the device; wherein a change in the data obtained in step (iii) when compared to the data obtained in step (i) indicates that the one or more agents affects neuromuscular transmission.

BRIEF DESCRIPTION OF THE FIGURES

The accompanying Figures, which are incorporated in and constitute a part of this specification, illustrate several aspects of the invention and together with the description serve to explain the principles of the invention.

FIG. 5A shows the average peak force (nN) of a co-culture following glutamate treatment and following glutamate treatment with tubocurarine. FIG. 5B shows the average peak force (nN) of muscle cells only following glutamate treatment and following glutamate treatment with tubocurarine.

FIG. 6A shows staining for the presynaptic marker Synaptic Vesicle Protein 2. FIG. 6B shows staining for β-III-Tubulin. FIG. 6C shows staining for α-bungarotoxin. FIG. 6D shows a composite image of FIG. 6A, FIG. 6B, and FIG. 6C.

FIG. 8A shows that the cantilevers are located in the first chamber and are spaced from the second chamber by a PDMS barrier. FIG. 8B shows a magnified schematic. In this example, a positive (+) and a negative (−) electrode extend into the second chamber with the motoneurons. The barrier shown in FIG. 8B comprises guide channels extending through the PDMS between the two chambers.

FIG. 9A shows myotubes cultured on the surface of the cantilevers in the first chamber. FIG. 9B shows the guide channels extending through the barrier between the chambers. FIG. 9C shows motoneurons cultured on the surface of a plurality of electrodes in the second chamber. In this example, the electrodes shown are part of a microelectrode array.

FIG. 10A is a phase contrast image overlaid with immunocytochemical staining FIGS. 10B and 10C are the same field of view as FIG. 10A but FIG. 10B shows only the immunocytochemical staining for myosin heavy chain (a myotube marker). FIG. 10C shows only immunocytochemical staining for neurofilament (a neural marker).

FIG. 11A is a phase contrast image overlaid with immunocytochemical staining FIGS. 11B and 11C are the same field of view as FIG. 11A but FIG. 11B shows only the immunocytochemical staining for myosin heavy chain (a myotube marker). FIG. 11C shows only the immunocytochemical staining for neurofilament (a neural marker).

FIGS. 11 D-F are magnified views of the circles from FIGS. 11A-C.

FIG. 12A shows myotube contractions prior to addition of the agent. FIG. 12B shows myotube contractions after addition of 5 nM bungarotoxin. FIG. 12C shows myotube contractions after addition of 50 nM bungarotoxin. FIG. 12D shows myotube contractions after addition of 100 nM bungarotoxin. As shown in the figures, increasing concentrations of α-bungarotoxin caused decreased contraction of the myotubes. FIG. 12E shows a time plot of myotube contractions detected by a video camera following treatment with 100 nM α-bungarotoxin (e.g., FIG. 12D) but stimulated from the first chamber (the myotube side). This demonstrates that the myotubes are functional (i.e., contractions are still possible) but the neuromuscular junctions are not functional.

Figure 1A:
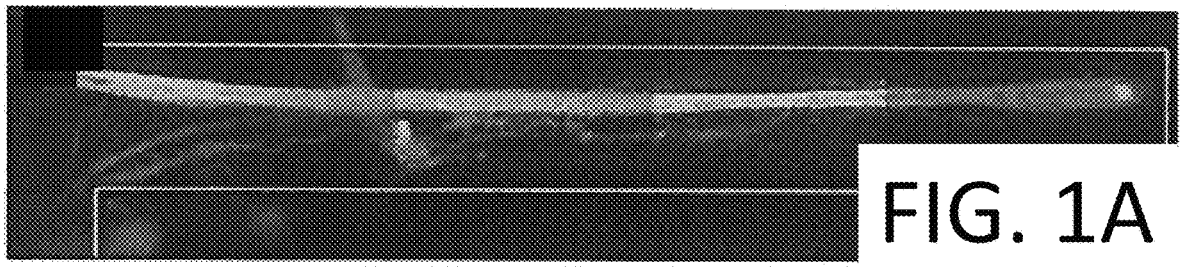
FIG. 1A shows a composite image of a primary rat myotube co-cultured with primary rat motoneurons on a cantilever.

The differential in pixel intensity over time may then be used to generate time plots of the contraction of the myotubes.

DESCRIPTION

The present invention can be understood more readily by reference to the following detailed description of the invention and the Examples included therein.

Additional advantages of the invention will be set forth in part in the description which follows, and in part will be clear from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Before the present devices and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not. For example, a serum-free medium disclosed herein can optionally comprise one or more growth factors and/or hormones known to the art.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, the subject is a human being.

In an aspect, a subject can be afflicted with one or more diseases or disorders, such as, for example, a CNS (central nervous system) disease or disorder. As used herein, the terms "CNS disease" or "CNS disorder" refer to neurological and/or psychiatric changes in the CNS, e.g., brain and spinal cord, which changes manifest in a variety of symptoms. Examples of CNS diseases or disorders include, but are not limited to, the following: migraine headache; cerebrovascular deficiency; psychoses including paranoia, schizophrenia, attention deficiency, and autism; obsessive/compulsive disorders including anorexia and bulimia; convulsive disorders including epilepsy and withdrawal from addictive substances; cognitive diseases including Parkinson's disease and dementia; and anxiety/depression disorders such as anticipatory anxiety (e.g., prior to surgery, dental work and the like), depression, mania, seasonal affective disorder (SAD); and convulsions and anxiety caused by withdrawal from addictive substances such as opiates, benzodiazepines, nicotine, alcohol, cocaine, and other substances of abuse. CNS diseases and disorders also include, but are not limited to, the following: Abercrombie's degeneration, Acquired epileptiform aphasia (Landau-Kleffner Syndrome), Acute Disseminated Encephalomyelitis, Adrenoleukodystrophy, Agnosia, Alexander Disease, Alpers' Disease, Alternating Hemiplegia, Amyotrophic Lateral Sclerosis, Angelman Syndrome, Ataxia Telangiectasia, Ataxias and Cerebellar/Spinocerebellar Degeneration, Attention Deficit Disorder, Binswanger's Disease, Canavan Disease, Cerebral Hypoxia, Cerebro-Oculo-Facio-Skeletal Syndrome, Charcot-Marie-Tooth, Chronic Inflammatory Demyelinating Polyneuropathy (CIDP), Corticobasal Degeneration, Creutzfeldt-Jakob disease, Degenerative knee arthritis, Diabetic neuropathy, Early Infantile Epileptic Encephalopathy (Ohtahara Syndrome), Epilepsy, Friedreich's Ataxia, Guillain-Barre Syndrome (GBS), Hallervorden-Spatz Disease, Huntington's Disease, Krabbe Disease, Kugelberg-Welander Disease (Spinal Muscular Atrophy), Leigh's Disease, Lennox-Gastaut Syndrome, Machado-Joseph Disease, Macular degeneration, Monomelic Amyotrophy, Multiple Sclerosis, Neuroacanthocytosis, Niemann-Pick disease, Olivopontocerebellar Atrophy, Paraneoplastic Syndromes, Parkinson's Disease, Pelizaeus-Merzbacher Disease, Pick's Disease, Primary Lateral Sclerosis, Progressive Locomotor Ataxia (Syphilitic Spinal Sclerosis, Tabes Dorsalis), Progressive Supranuclear Palsy, Rasmussen's Encephalitis, Rett Syndrome, Tourette's Syndrome, Usher syndrome, West syndrome (Infantile Spasms), and Wilson Disease. General characteristics of such diseases are known in the art. The skilled person can identify additional CNS diseases and disorders known in the art without undue experimentation.

In an aspect, a subject can be afflicted with one or more diseases or disorders, such as, for example, a PNS (peripheral nervous system) disease or disorder. As used herein, the terms "PNS disease" or "PNS disorder" can refer to a disease, illness, condition, or disorder that affects part or all of the peripheral nervous system. The PNS can comprise all the nerves in your body, aside from the ones in the brain and spinal cord. The PNS can act as a communication relay between the brain and the extremities. Unlike the CNS, the PNS is not protected by bone or the blood-brain barrier, which renders it exposed to toxins and mechanical injuries. Generally, the PNS can be divided into the somatic nervous system and the autonomic nervous system. As known to the art, there are over 100 types of PNS diseases and disorders. The causes of these PNS diseases or disorders include, but are not limited to, the following: diabetes, genetic predispositions (hereditary causes); exposure to toxic chemicals, alcoholism, malnutrition, inflammation (infectious or autoimmune), injury, and nerve compression; and by taking certain medications such as those used to treat cancer and HIV/AIDS. PNS diseases and disorders include anesthesia, hyperesthesia, paresthesia, and neuralgia. PNS diseases and disorders include, but are not limited to, the following: accessory nerve disorder, acrodynia, hand-arm vibration syndrome, amyloid neuropathies, anesthesia dolorosa, antimag peripheral neuropathy, autonomic dysreflexia, axillary nerve dysfunction, axillary nerve palsy, brachial plexus neuropathies, carpal tunnel syndrome, Charcot-Marie-Tooth disease, chronic solvent-induced encephalopathy, CMV polyradiculomyelopathy, complex regional pain syndromes, congenital insensitivity to pain with anhidrosis, diabetic neuropathies, dysautonomia, facial nerve paralysis, facial palsy, familial dysautonomia, Guillain-Barre syndrome, hereditary sensory and autonomic neuropathy, Horner's syndrome, Isaacs syndrome, ischiadica, leprosy, mononeuropathies, multiple system atrophy, myasthenia gravis, myotonic dystrophy, nerve compression syndrome, nerve injury, neuralgia, neuritis, neurofibromatosis, orthostatic hypotension, orthostatic intolerance, primary autonomic failure, pain insensitivity (congenital), peripheral nervous system neoplasms, peripheral neuritis, peripheral neuropathy, piriformis syndrome, plexopathy, polyneuropathies, polyneuropathy, post-herpetic neuralgia, postural orthostatic tachycardia syndrome, pronator teres syndrome, proximal diabetic neuropathy, pudendal nerve entrapment, pure autonomic failure, radial neuropathy, radiculopathy, sciatica, Tarlov cysts, thoracic outlet syndrome, trigeminal neuralgia, ulnar neuropathy, vegetative-vascular dystonia, Villaret's syndrome, Wartenberg's syndrome, and winged scapula.

As used herein, the term "diagnosed" means having been subjected to a physical examination by a person of skill, for example, a physician, and found to have a condition that can be diagnosed, evaluated, or treated by a disclosed device or a disclosed method. In an aspect, a subject can be diagnosed with one or more CNS disease or disorder. In an aspect, a subject can be diagnosed with one or more PNS disease or disorder. In an aspect, a subject can be diagnosed with one or more CNS disease or disorder and one or more PNS disease or disorder. For example, in an aspect, "diagnosed with a PNS disease or disorder" can refer to a diagnosis of a subject with a muscle wasting condition or a peripheral neuropathy. In an aspect, "diagnosed with a PNS disease or disorder" can refer to a diagnosis of a subject with one or more of the PNS diseases or disorders listed herein. In other words, "diagnosed with a PNS disease or disorder" means having been subjected to a physical examination by a person of skill, for example, a physician, and found to have a condition that can be diagnosed, evaluated, or treated by a disclosed device or a disclosed method. For example, in an aspect, "diagnosed with a CNS disease or disorder" can refer to a diagnosis of a subject one or more of the CNS diseases or disorders listed herein. In other words, "diagnosed with a CNS disease or disorder" means having been subjected to a physical examination by a person of skill, for example, a physician, and found to have a condition that can be diagnosed, evaluated, or treated by a disclosed device or a disclosed method.

As used herein, the term "treatment" refers to the medical management of a subject with the intent to cure, ameliorate, stabilize, or prevent a disease, pathological condition, or disorder (such as, for example, a muscle wasting condition or a peripheral neuropathy). In an aspect, a subject can have one or more CNS disease or disorder. In an aspect, a subject can have one or more PNS disease or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action. In an aspect, something can be one or more CNS diseases or disorders. In an aspect, something can be one or more PNS diseases or disorders (such as, for example, a muscle wasting condition or a peripheral neuropathy). It is understood that where reduce, inhibit, or prevent are used herein, unless specifically indicated otherwise, the use of the other two words is also expressly disclosed.

As used herein, the terms "administering" and "administration" refer to any method of providing a disclosed composition, complex, or a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition, such as, for example, a CNS disease or disorder or a PNS disease or disorder. Examples of CNS and PNS diseases and disorders are listed herein.

The term "contacting" as used herein refers to bringing a disclosed composition, compound, or complex together with an intended target (such as, e.g., a cell or population of cells, a receptor, an antigen, or other biological entity) in such a manner that the disclosed composition, compound, or complex can affect the activity of the intended target (such as, e.g., a cell or population of cells, a receptor, an antigen, or other biological entity), either directly (i.e., by interacting with the target itself), or indirectly (i.e., by interacting with another molecule, co-factor, factor, or protein on which the activity of the target is dependent). For example, in an aspect of a disclose device or disclosed method, one or more agents can be contacted with a disclosed co-culture (e.g., motoneurons and muscle cells such as myotubes or myocytes) in a disclosed device via direct application or via introduction to the serum-free medium.

As used herein, the term "determining" can refer to measuring or ascertaining (i) an activity or an event, (ii) a quantity or an amount, (iii) a change in activity or an event, or (iv) a change in a quantity or an amount. Determining can also refer to measuring a change in prevalence and/or incidence of an activity, or an event, or a trait, or a characteristic. For example, determining can refer to measuring or ascertaining the level of a physiological response, such as, for example, peak force, time to half relaxation, and recovery following myotube exhaustion. In an aspect, for example, determining can refer to measuring or ascertaining cantilever deflection, stress produced by a myotube, and/or force of the myotube. The art is familiar with methods and techniques used to measure or ascertain (i) an activity or an event, (ii) a quantity or an amount, (iii) a change in activity or an event, (iv) a change in a quantity or an amount, or (v) a change prevalence and/or incidence of an activity, or an event, or a trait, or a characteristic. For example, the art is well versed in the use of immunohistochemistry to identify, characterize, and quantify a particular cell type (e.g., a motoneuron, a muscle cell, a myoblast, a myotube, a myocyte, a stem cell, a neural progenitor cell) or a cellular structure such as a neuromuscular junction.

As used herein, the terms "effective amount" and "amount effective" refer to an amount that is sufficient to achieve the desired result or to have an effect on an undesired condition. For example, in an aspect, an effective amount of a disclosed composition or agent is the amount effective to elicit or evoke neurotransmission using a disclosed device.

A "therapeutically effective amount" refers to an amount that is sufficient to achieve the desired therapeutic result or to have an effect on undesired symptoms, but is generally insufficient to cause adverse side effects. The specific therapeutically effective dose level for any particular subject will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a composition or complex at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "transgene" can refer to a nucleic acid sequence encoding a foreign protein, which is partly or entirely heterologous to the transgenic animal or cell into which is introduced. A transgene contains optionally one or more transcriptional regulatory sequences and any other nucleic acid, such as introns, that may be necessary for optimal expression of the selected nucleic acid, all operably linked to the selected nucleic acid, and may have an enhancer sequence. The transgenic gene may be placed into an organism by introducing the foreign gene into embryonic stem (ES) cells, fertilized eggs or early embryos. Furthermore, "transgenic animal" refers to any animal in which one or more or all of the cells of the animal include a transgene. The transgene is introduced into the cell, directly or indirectly by introduction into a precursor of the cell, through genetic manipulation such as by microinjection or infection with a vector (such as a plasmid). Transgenes and methods used to introduce transgenes into cells and animals are known to the art. Transgenic animals are known to the art.

As used herein, "growth factors" can refer to proteins that bind to receptors on the surface of one or more cells to effect cellular proliferation and/or differentiation. In an aspect, one or more growth factors can be added to a medium, such as, for example, a disclosed serum-free medium. Growth factors are known to the art and can include, but are not limited to, the following: Epidermal Growth Factor (EGF), Platelet-Derived Growth Factor (PDGF), Fibroblast Growth Factors (FGFs), Transforming Growth Factors-β TGFs-β), Transforming Growth Factor-α (TGF-α), Erythropoietin (Epo), Insulin-Like Growth Factor-1 (IGF-1), Insulin-Like Growth Factor-2 (IGF-2), Interleukin-1 (IL-1), Interleukin-2 (IL-2), Interleukin-6 (IL-6), Interleukin-8 (IL-8), Tumor Necrosis Factor-α (TNF-α), Tumor Necrosis Factor-β (TNF-β), Interferon-γ (INF-γ), and Colony Stimulating Factors (CSFs). In an aspect, one or more growth factors can be added to the serum-free medium.

Culture surfaces can be patterned. For example, treatment of surfaces with cytophilic and cytophobic surface modifications allows for a high degree of control over cellular location within in vitro culture systems. Such patterning also facilitates dictation of cellular outgrowth direction, allowing investigators to influence when and how different cell populations interact in culture. Pattern geometries can influence various aspect of the culture. For example, not only contact interaction with the surface, but also the shape of the attachment area determines the physiology of cell types (such as myocytes). Methods for cell patterning are known to the art. For example, methods can comprise direct placement of cells or extracellular matrix molecules on desired locations and can include patterning through microfluidic channels, microcontact printing and inkjet printing. Another method known to the art can comprises photolithography following surface modification with self-assembled monolayers (SAMs) for neurons as well as myocytes. Also, the cell surface can comprise a negative surface (e.g., polyethylene glycol, polyacrylic acid, and polyacrylamide) resistant to cell attachment. The negative surface can bear a pattern ablated thereon. A positive surface promoting cell attachment can be deposited on the pattern ablated on the negative surface.

In an aspect, a device disclosed herein can comprise one or more patterned surfaces upon which one or more cell populations are cultured. In an aspect, a device disclosed herein can comprise one or more patterned cantilevers upon which one or more cell populations are cultured. For example, in an aspect, one or more cell populations can comprise myotubes, myocytes, motoneurons, stem cells, neural progenitor cells, and sensory neurons. In an aspect, a disclosed device can comprise myotubes culturing on a patterned surface. In an aspect, a disclosed device can comprise myocytes culturing on a patterned surface. In an aspect, a disclosed device can comprise motoneurons culturing on a patterned surface. In an aspect, a disclosed device can comprise stem cells culturing on a patterned surface. In an aspect, a disclosed device can comprise neural progenitor cells culturing on a patterned surface. In an aspect, a disclosed device can comprise sensory neurons culturing on a patterned surface. In an aspect, a disclosed device can comprise co-culturing cells on a patterned surface. In an aspect, a disclosed device can comprise co-culturing myotubes and motoneurons on a patterned surface.

As used herein, "hormone" refers to a chemical that interacts with a receptor in a target tissue to effect a change in the function of that tissue. In an aspect, one or more hormones can be added to a medium, such as, for example, a disclosed serum-free medium. Hormones are known to the art and can include, but are not limited to, the following: Adrenocorticotrophic hormone, Antidiuretic hormone, Cortisol, Dehydroepiandrostendione, Dihydrotestosterone, Estrogens (e.g., estradiol, estrone, estriol), Follicle Stimulating hormone, Growth Hormone, Inhibin, Insulin, Luteinizing hormone, Melanocyte stimulating hormone, Melatonin, Progesterone, Prolactin, Proopiomelanocortin, Testosterone, Thyroid stimulating hormone, Thyroxine, and Triiodothyronine.

As used herein, "surface-modified" or "surface coated" refers to a coating or modification of some sort to a solid support or surface (i.e., glass coverslip or cantilever). Surface modifications and surface coatings are known to the skilled person in the art. Surface modification can comprise modifying one or more surfaces of a material by bringing physical, chemical, or biological characteristics different from the ones originally found on the one or more surfaces of a material. In an aspect, a surface modification can alter a range of characteristics of the one or more surfaces, including, but not limited to the following: roughness, hydrophilicity, hydrophobicity, surface charge, surface energy, biocompatibility, and reactivity.

In the art, a surface modification can be generated using traditional protein absorption, for example, of extracellular matrix proteins, or can be generated using self-assembled monolayers (SAMs). In an aspect, SAMs comprise extracellular matrix components. Extracellular matrix components are known to the skilled person in the art and can comprise, for example, fibronectin and collagen. SAMs disclosed herein may comprise organo silanes containing amine moieties, and polyethylene-glycol moieties. Organo silanes containing amine moieties can comprise trimethoxysilylpropyldiethylenetriamine (DETA). Polyethylene-glycol moieties can comprise 2-[Methoxypoly(ethyleneoxy) propyl]trimethoxysilane). Surface-modifications and surface-coatings can comprise other self-assembled monolayers (e.g., tridecafluoro-1,1,2,2-tetrahydrooctyl-1-25 dimethylchlorosilane (13F) and polyethylene glycol silane (PEG)) known to the art. Other biopolymer coatings are known to the art including, but not limited to, the following: collagen, laminin, poly-D-lysine, poly-L-ornithine, fibronectin, vitronectin, and Matrigel.

In an aspect, surface modifications and/or surface coatings can comprise plasma modifications, plasma coatings, or plasma activation. In an aspect, modifications and/or coatings can comprise chemical vapor deposition (CVD). In an aspect, modifications and/or coatings can comprise addition of polymers or polymer modifications. Plasma is a partially ionized gas generated by applying an electrical field to a gas under at least partial vacuum. Plasma applications can comprise surface activation and modifications. For example, in an aspect, plasma can modify surfaces by attachment or adsorption of functional groups to tailor surface properties for one or more specific applications. In an aspect, plasma modification can restructure polymer surfaces through crosslinking, deposit polymer layers by plasma polymerization, can graft functional polymers or end groups onto plasma-activated surfaces, can prepare surfaces for subsequent processing, e.g., film deposition or adsorption of molecules, can improve surface coverage and spreading of coatings and enhance adhesion between two surfaces, can modify wettability to render a surface hydrophilic or hydrophobic with the appropriate process gas(es), and/or change surface properties without affecting the bulk material. As known to the art, plasma processing methods include, but are not limited to, the following: oxygen or air plasma, argon plasma, carbon tetrafluoride ($CF_4$) plasma.

Chemical vapor deposition (CVD) is known to the art. CVD can be practiced in a variety of formats. For example, in an aspect, CVD can be classified by operating pressure such as (i) atmospheric pressure CVD, (ii) low-pressure CVD, and (iii) ultrahigh vacuum CVD. In an aspect, CVD can be classified by physical characteristics of vapor such as (i) aerosol assisted CVD and (ii) direct liquid injection CVD. The art is familiar with other types of CVD including, but not limited to, the following: plasma methods (such as microwave plasma-assisted CVD, plasma-enhanced CVD, remote plasma-enhanced CVD), atomic-layer CVD, combustion chemical vapor deposition, hot-wire CVD (i.e., catalytic CVD or hot filament CVD), hybrid physical-chemical vapor deposition, metalorganic chemical vapor deposition, rapid thermal CVD, vapor-phase epitaxy, and photo-initiated CVD.

Polymer modification is well known to the art. For example, the art is familiar with methods and techniques used to achieve covalent attachment of bioactive compounds to functionalized polymer surfaces. These techniques include, but are not limited to, the following: wet chemical, organosilanization, ionized gas treatments, and UV irradiation. Methods of analysis of biofunctionalized polymer surfaces, including spectral methods (e.g., X-ray photoelectron spectroscopy, Fourier transform infrared spectroscopy, atomic force microscopy, and others) as well as non-spectral methods (e.g., contact angle, dye assays, biological assays, and zeta potential) are also considered. The skilled person is familiar with the covalent conjugation of bioactive compounds to modified polymer surfaces, such as usage of hydrophilic, bifunctional, and/or branched spacer molecules.

As used herein, "SAMs" or "self-assembled monolayers" are known in the art as providing the needed design flexibility, both at the individual molecular and at the material levels, and offer a vehicle for investigation of specific interactions at interfaces, and of the effect of increasing molecular complexity on the structure and stability of two-dimensional assemblies. Generally, self-assembled monolayers (SAMs) can be prepared by immersing clean silica substrates in organic solvents containing 1-2% silane, and then rinsing the slide three times with the same solvent. After the final rinsing step, the slides are baked on a hotplate to quickly remove residual solvent and to promote complete reaction of the silanes with the reactive surface groups. SAM-modified surfaces can be characterized using X-ray photoelectron spectroscopy (XPS) (Briggs 1992) to demonstrate formation of the SAM and contact angle measurements to quantify wettability. Contact angle measurements are a rapid and simple measure of wettability. Contact angles are measured by application of static, sessile drops (5-30 µL) of deionized water to substrate surfaces with a micropipetter.

As used herein, "GlutaMAX™" refers to L-alanyl-L-glutamine, which is a dipeptide substitute for L-glutamine. GlutaMAX™ (Life Technologies) can be used as a direct substitute for L-glutamine at equimolar concentrations in mammalian cell cultures with minimal or no adaptation. GlutaMAX™ improves growth efficiency and performance of mammalian cell culture systems. GlutaMAX™ eliminates problems associated with the spontaneous breakdown of L-glutamine during incubation. It is highly soluble in aqueous solution and is heat stable.

As used herein, "neurobasal medium" refers to a basal medium that is formulated to meet the special requirements of neuronal cells. Neurobasal medium (Life Technologies) allows for long-term maintenance of the normal phenotype and growth of neuronal cells and maintains pure populations of neuronal cells without the need of an astrocyte feeder layer. Neurobasal medium can comprise amino acids, vitamins, inorganic salts, or other components. For example, in an aspect, neurobasal medium can comprise (i) the amino acids Glycine, L-Alanine, L-Arginine hydrochloride, L-Asparagine-$H_2O$, L-Cysteine, L-Histidine hydrochloride-$H_2O$, L-Isoleucine, L-Leucine, L-Lysine hydrochloride, L-Methionine, L-Phenylalanine, L-Proline, L-Serine, L-Threonine, L-Tryptophan, L-Tyrosine, and L-Valine; (ii) the vitamins Choline chloride, D-Calcium pantothenate, Folic Acid, Niacinamide, Pyridoxine hydrochloride, Riboflavin, Thiamine hydrochloride, Vitamin B12, and i-Inositol; (iii) the inorganic salts Calcium Chloride ($CaCl_2$) (anhyd.), Ferric Nitrate ($Fe(NO_3)_3$"$9H_2O$), Magnesium Chloride (anhydrous), Potassium Chloride (KCl), Sodium Bicarbonate ($NaHCO_3$), Sodium Chloride (NaCl), Sodium Phosphate monobasic ($NaH_2PO_4$—$H_2O$), and Zinc sulfate ($ZnSO_4$-$7H_2O$); and (iv) D-Glucose (Dextrose), HEPES, Phenol Red, and Sodium Pyruvate.

As used herein, "B27" or "B-27® Supplement" refers to serum-free supplement used to support the low or high density growth and short or long-term viability of hippocampal and other CNS neurons. B27 (Life Technologies) can be used in conjunction with neurobasal medium and can be used for neuronal cell culture without the need for an astrocyte feeder layer. B27 can comprise vitamins, proteins, or other components. For example, in an aspect, B27 can comprise (i) the vitamins Biotin, DL Alpha Tocopherol Acetate, DL Alpha-Tocopherol, and Vitamin A (acetate); (ii) the proteins BSA, fatty acid free Fraction V, Catalase, Human Recombinant Insulin, Human Transferrin, and Superoxide Dismutase; and (iii) Corticosterone, D-Galactose, Ethanolamine HCl, Glutathione (reduced), L-Carnitine HCl, Linoleic Acid, Linolenic Acid, Progesterone, Putrescine 2HCl, Sodium Selenite, and T3 (triodo-I-thyronine).

As used herein, "myotube" refers to a large, elongated muscle cell that contains many nuclei. In an aspect, skeletal myoblasts fuse together to form a multinucleated myotube. In an aspect of a disclosed method or device, myoblasts can fuse together to form a functional myotube that forms a synapse with a motoneuron. In an aspect, myoblasts can exist as part of the collection of muscle cells subjected to co-culturing with motoneurons. As used herein, "myoblasts" and "muscle cells" are synonymous.

As used herein, "stem cells" can have remarkable potential to develop into many different cell types in the body during early life and growth. In many tissues, stem cells can also serve as a sort of internal repair system, dividing essentially without limit to replenish other cells as long as the person or animal is still alive. When a stem cell divides, each new cell can have the potential either to remain a stem cell or become another type of cell with a more specialized function, such as a muscle cell or a motoneuron. Stem cells can be distinguished from other cell types by two important characteristics. First, stem cells are unspecialized cells capable of renewing themselves through cell division, sometimes after long periods of inactivity. Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions. Given the unique regenerative abilities, stem cells can offer new potentials for treating diseases and/disorders such as CNS diseases or disorders and PNS diseases or disorders. Stem cells are unspecialized, which means that a stem cell does not have any tissue-specific structures that allow it to perform specialized functions. However, unspecialized stem cells can give rise to specialized cells, including heart muscle cells, blood cells, or nerve cells. Stem cells can give rise to specialized cells, which means that the unspecialized stem cells give rise to specialized cells through differentiation. U.S. Patent Application No. 61/784,923 is incorporated by reference in its entirety for its disclosures and teachings related to methods of generating sensory neurons, Schwann cells, and neural crest stem cells, the methods comprising proliferating a population of neural progenitor cells.

As used herein, "piezoelectricity" refers to the electric charge that accumulates in certain solid materials and biological matter in response to applied mechanical stress. As known to the art, the piezoelectric effect can be understood as the linear electromechanical interaction between the mechanical and the electrical state in crystalline materials with no inversion symmetry. The piezoelectric effect is a reversible process in that materials exhibiting the direct piezoelectric effect (the internal generation of electrical charge resulting from an applied mechanical force) also exhibit the reverse piezoelectric effect (the internal generation of a mechanical strain resulting from an applied electrical field). For example, as described herein, a cantilever's bending or vibration initiates strain in the piezoresistor that leads to a change in its electrical conductivity. This conductance is easily monitored with simple circuitry. The governing equation for piezoresistance is:

$$\frac{\Delta R}{R} = \sigma_l \pi_l + \sigma_t \pi_t$$

Here, R is the resistance, $\sigma_l$ is the longitudinal stress component (stress component parallel to the direction of the current), $\sigma_t$ is the transversal stress component (the stress component perpendicular to the direction of current), $\pi_l$ is the longitudinal piezoresistance coefficient, and $\pi_t$ is the transversal piezoresistance coefficient. The piezoresistance coefficients are functions of the material and the crystal orientation within the material. When a piezoelectric cantilever is used, the read-out microelectronics can easily be integrated on the silicon chip.

As known to the art, both natural and synthetic materials exhibit piezoelectricity. For example, several naturally occurring crystals can exhibit piezoelectricity including, but not limited to, the following: berlinite ($AlPO_4$), sucrose (table sugar), quartz, rochelle salt, topaz, and tourmaline-group mineral. Bone can also exhibit piezoelectricity. Several biological materials can exhibit piezoelectric properties including, but not limited to, the following: tendon, silk, wood, enamel, dentin, DNA, and certain viral proteins. Synthetic crystals such as gallium orthophosphate ($GaPO_4$), a quartz analogic crystal, and langasite ($La_3Ga_5SiO_{14}$), also a quartz analogic crystal, can demonstrate piezoelectric properties. Several synthetic ceramics, especially those with perovskite or tungsten-bronze structures, can exhibit piezoelectricity (i.e., Barium titanate ($BaTiO_3$), Lead titanate ($PbTiO_3$), Lead zirconate titanate ($Pb[Zr_xTi_{1-x}]O_3$ $0 \leq x \leq 1$) and more commonly known as PZT or lead zirconate titanate, potassium niobate ($KNbO_3$), Lithium niobate ($LiNbO_3$), Lithium tantalate ($LiTaO_3$), Sodium tungstate ($Na_2WO_3$), Zinc oxide (ZnO), $Ba_2NaNb_5O_5$, and $Pb_2KNb_5O_{15}$. There are also lead-free piezoceramics that demonstrate piezoelectricity (i.e., sodium potassium niobate ((K,Na)$NbO_3$), bismuth ferrite ($BiFeO_3$), sodium niobate ($NaNbO_3$), bismuth titanate ($Bi_4Ti_3O_{12}$), sodium bismuth titanate ($Na_{0.5}Bi_{0.5}TiO_3$). Polymers also demonstrate piezoelectricity (e.g., polyvinylidene fluoride (PVDF)) as do some organic nanostructures (e.g., self-assembled diphenyl-alanine peptide nanotubes (PNTs)).

As used herein, neuromuscular junctions (NMJs) are peripheral synapses essential for conveying efferent signals from the motoneurons of the central nervous system to their proximal skeletal muscle fibers. NMJs and their structural components are known to the art.

B. Devices i) Device Comprising Detection System Comprising a Laser and a Photo-Detector Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers). In an aspect, a disclosed detection system can comprise a laser and a photo-detector.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantlievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

As known to the art, a cantilever can be a projecting structure that is supported at only one end. Typically, microcantilevers can be used for the measurement of deflections resulting from small surface stress changes or surface mass changes due to adsorption of molecules. The two common methods of measuring the response of a microcantilever are determination of bending of the beam and measurement of a change in the resonance frequency. Both of these detection methods can be achieved with optical and/or electrical methods.

Figure 7:
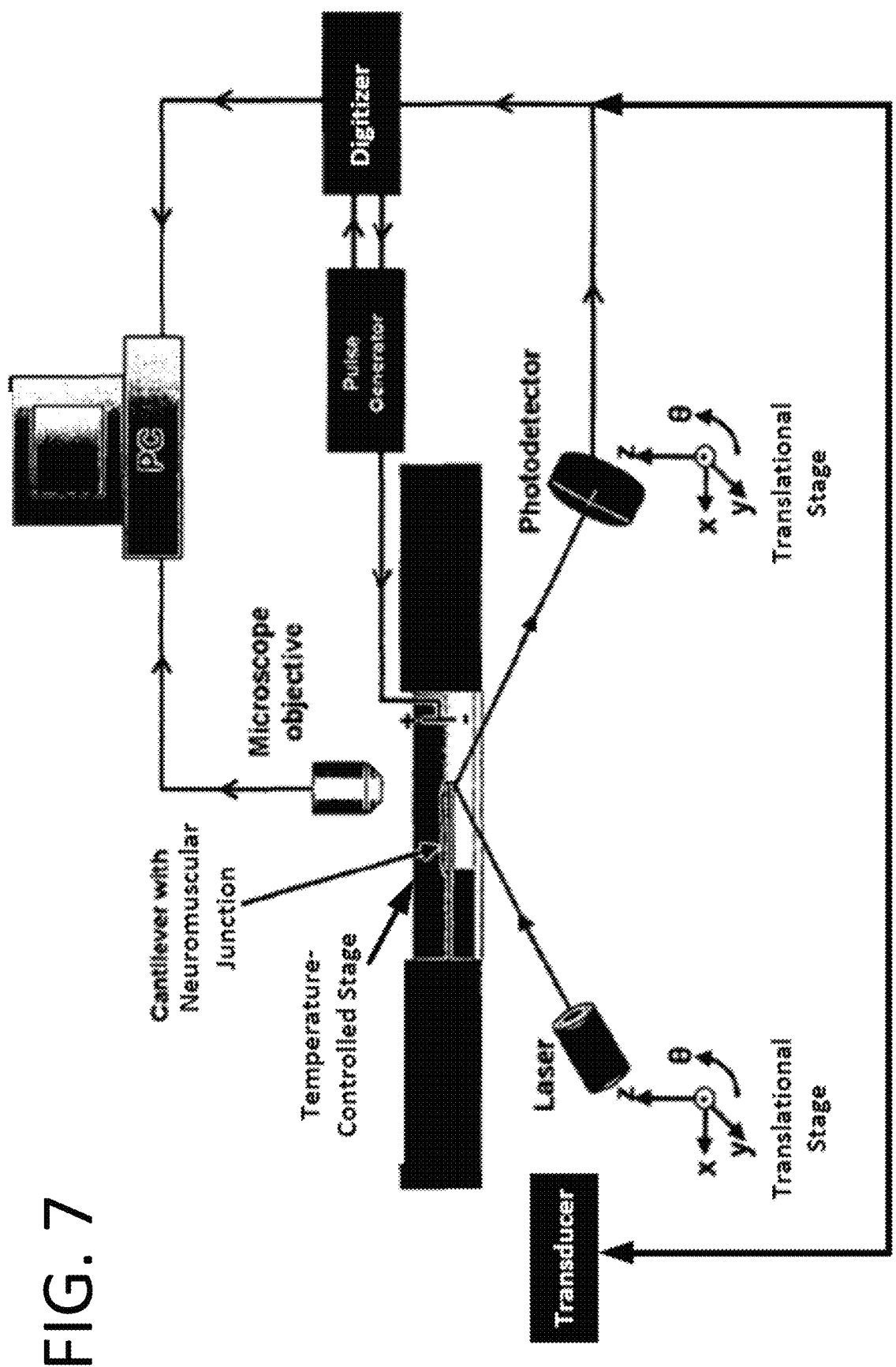
FIG. 7 is a schematic representation of an example detection system used with implementations described herein.

In an aspect, a disclosed detection system (e.g., as shown in FIG. 7) can comprise a plurality of linear actuators attached to XY translational stages that control the position of the laser and photo-detector. In an aspect, a detection system comprising a plurality of linear actuators can comprise a digitizer and a computer, wherein the photo-detector is in communication with the digitizer and wherein the digitizer is in communication with the computer. In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, each cantilever can be surface-modified or surface-coated. Surface modifications are known to those skilled in the art. In an aspect, a surface modification can comprise ((3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells (e.g., myoblasts, etc.) or motoneurons can be obtained from a subject diagnosed with or suspected of having a muscle wasting condition. As known to the art, a muscle wasting condition can be considered a peripheral nervous system disease or disorder. As known to the art, muscle wasting or atrophy is a serious complication of various clinical conditions that significantly worsens the prognosis of the illnesses. Two types of muscle atrophy are commonly recognized: (1) disuse atrophy and (2) neurogenic atrophy. Disuse atrophy can occur from a lack of physical activity and typically can be reversed with exercise and better nutrition. Neurogenic atrophy is more severe and can occur when there is an injury to, or disease of, a nerve that connects to the muscle. This type of muscle atrophy tends to occur more suddenly than disuse atrophy. Causes of muscle wasting or muscle atrophy include, but are not limited to, the following: alcohol-associated myopathy, amyotrophic lateral sclerosis (ALS or Lou Gehrig's disease), burns, dermatomyositis and polymyositis, Guillain-Barre syndrome, other physical injury, long-term corticosteroid therapy, malnutrition, motor neuropathy (such as diabetic neuropathy), muscular dystrophy, immobilization, osteoarthritis, polio, rheumatoid arthritis, spinal cord injury, and stroke.

In an aspect, if at least one muscle cell (e.g., myoblasts, etc.) is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells (e.g., myoblasts, etc.) or motoneurons can be obtained from a subject diagnosed with or suspected of having a peripheral neuropathy. As known to the art, peripheral neuropathy can occur as a result of nerve damage sustained due to traumatic injuries, infections, metabolic problems, and exposure to toxins. Because every peripheral nerve has a highly specialized function in a specific part of the body, a wide array of symptoms can occur when nerves are damaged. Some subjects may experience temporary numbness, tingling, and pricking sensations (paresthesia), sensitivity to touch, or muscle weakness. Others may suffer more extreme symptoms, including burning pain (especially at night), muscle wasting, paralysis, or organ or gland dysfunction. Subjects may become unable to digest food easily, maintain safe levels of blood pressure, sweat normally, or experience normal sexual function. In the most extreme cases, breathing may become difficult or organ failure may occur. The art has identified more than 100 types of peripheral neuropathies, each with its own characteristic set of symptoms, pattern of development, and prognosis.

In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to have or suspected of having a role in the etiology of a muscle wasting condition or a peripheral neuropathy. In an aspect, a transgenic animal can comprise one or more transgenes known to have or suspected of having a role in the etiology of a muscle wasting condition or a peripheral neuropathy. In an aspect, a transgenic animal can comprise one or more transgenes known to have or suspected of having a role in the etiology of a CNS disease or disorder. In an aspect, a transgenic animal can comprise one or more transgenes known to have or suspected of having a role in the etiology of a PNS disease or disorder.

In an aspect of a disclosed device, the co-culture can be maintained in a serum-free medium. Mediums, including serum-free mediums, are known to the skilled person in the art. Methods and techniques to optimize one or more mediums for a particular cell type or a particular set of culture conditions are known to the skilled person in the art. For example, a disclosed medium can be optimized via the use of additional components, such as, for example, growth factors and/or hormones and/or antibiotics. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

ii) Device Comprising Detection System Comprising a Transducer

Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers).

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantlievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed detection system (e.g., as shown in FIG. 7) can comprise a transducer for detecting a change in electrical conductivity of the cantilever. In an aspect, each of the cantilevers can comprise one or more piezoelectric materials. In an aspect, piezoelectric materials can comprise quartz, bone, sodium tungstate, zinc oxide, and lead zirconate titanate. In an aspect, piezoelectric materials can comprise any piezoelectric material known to the art. As known to the art, both natural and synthetic materials exhibit piezoelectricity. For example, several naturally occurring crystal exhibit piezoelectricity including, but not limited to, the following: berlinite ($AlPO_4$), sucrose (table sugar), quartz, rochelle salt, topaz, and tourmaline-group mineral. Bone also exhibits piezoelectricity. Several biological materials exhibit piezoelectric properties including but not limited to, the following: tendon, silk, wood, enamel, dentin, DNA, and certain viral proteins. Synthetic crystals such as gallium orthophosphate ($GaPO_4$), a quartz analogic crystal, and langasite ($La_3Ga_5SiO_{14}$), a quartz analogic crystal, demonstrate piezoelectric properties. Several synthetic ceramics, especially those with perovskite or tungsten-bronze structures, exhibits piezoelectricity (i.e., Barium titanate ($BaTiO_3$), Lead titanate ($PbTiO_3$), Lead zirconate titanate ($Pb[Zr_xTi_{1-x}]O_3$ $0 \leq x \leq 1$) and more commonly known as PZT or lead zirconate titanate, potassium niobate ($KNbO_3$), Lithium niobate ($LiNbO_3$), Lithium tantalate ($LiTaO_3$), Sodium tungstate ($Na_2WO_3$), Zinc oxide (ZnO), $Ba_2NaNb_5O_5$, and $Pb_2KNb_5O_{15}$. There are also lead-free piezoceramics that demonstrate piezoelectricity (i.e., sodium potassium niobate ($(K,Na)NbO_3$), bismuth ferrite ($BiFeO_3$), sodium niobate ($NaNbO_3$), bismuth titanate ($Bi_4Ti_3O_{12}$), sodium bismuth titanate ($Na_{0.5}Bi_{0.5}TiO_3$). Polymers also demonstrate piezoelectricity (e.g., polyvinylidene fluoride (PVDF)) as do some organic nanostructures (e.g., self-assembled diphenylalanine peptide nanotubes (PNTs)).

In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, a "computer" or "computer system" can refer to the hardware components, software components, and data storage components used to store and/or analyze data generated, obtained, and/or collected using a disclosed device. A computer can comprise a computer readable medium and a processor for accessing and manipulating data generated, obtained, and/or collected using a disclosed device. In an aspect, a computer readable medium can comprise magnetically readable media, optically readable media, electronically readable media, or magnetic/optical media. For example, in an aspect, a computer readable medium can be a hard disc, a floppy disc, a magnetic tape, CD-ROM, DVD, RAM, or ROM or any other type of media known to those skilled in the art. In an aspect, a disclosed computer or disclosed computer system can be a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable. In an aspect, the computer system can comprise processor connected to a bus which is connected to a main memory, preferably implemented as RAM, and one or more data storage devices, such as a hard drive and/or other computer readable media having data recorded thereon. In an aspect, the computer system can comprise one or more data retrieving devices for reading the data stored on the data storage components. In an aspect, a data retrieving device can comprise, for example, a floppy disk drive, a compact disk drive, a magnetic tape drive, a hard disk drive, a CD-ROM drive, a DVD drive, etc. In an aspect, a data storage component can be a removable computer readable medium such as a floppy disk, a compact disk, a magnetic tape, etc. containing control logic and/or data recorded thereon. In an aspect, a computer system can be programmed by appropriate software for reading the control logic and/or the data from the data storage component once inserted in the data retrieving device. In an aspect, software for accessing and processing the data generated, collected, and/or obtained using a disclosed device (such as search tools, compare tools, modeling tools, etc.) can reside in main memory during execution.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells (e.g., myoblasts, etc.) or motoneurons can be obtained from a subject diagnosed with or suspected of having a peripheral neuropathy. The art is familiar with peripheral neuropathies. A description of peripheral neuropathies is provided above. The art is familiar with PNS diseases and disorders, which are also described above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

iii) Device Comprising Detection System Comprising a Video Camera

Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers).

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed detection system can comprise a video camera. The video camera may be configured to monitor the movement of one or more myotubes, for example, in response to an electrical stimulus. For example, pixels in each frame of the video can be normalized to the first frame in the video, and the pixels can then be combined on a frame-by-frame basis to generate a time plot of contractions (e.g., FIG. 13), as explained in the experimental section below. It is contemplated that any video camera capable of detecting movement of the myotubes can be used in the disclosed detection system.

In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, a "computer" or "computer system" can refer to the hardware components, software components, and data storage components used to store and/or analyze data generated, obtained, and/or collected using a disclosed device. A computer can comprise a computer readable medium and a processor for accessing and manipulating data generated, obtained, and/or collected using a disclosed device. In an aspect, a computer readable medium can comprise magnetically readable media, optically readable media, electronically readable media, or magnetic/optical media. For example, in an aspect, a computer readable medium can be a hard disc, a floppy disc, a magnetic tape, CD-ROM, DVD, RAM, or ROM or any other type of media known to those skilled in the art. In an aspect, a disclosed computer or disclosed computer system can be a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable. In an aspect, the computer system can comprise processor connected to a bus which is connected to a main memory, preferably implemented as RAM, and one or more data storage devices, such as a hard drive and/or other computer readable media having data recorded thereon. In an aspect, the computer system can comprise one or more data retrieving devices for reading the data stored on the data storage components. In an aspect, a data retrieving device can comprise, for example, a floppy disk drive, a compact disk drive, a magnetic tape drive, a hard disk drive, a CD-ROM drive, a DVD drive, etc. In an aspect, a data storage component can be a removable computer readable medium such as a floppy disk, a compact disk, a magnetic tape, etc. containing control logic and/or data recorded thereon. In an aspect, a computer system can be programmed by appropriate software for reading the control logic and/or the data from the data storage component once inserted in the data retrieving device. In an aspect, software for accessing and processing the data generated, collected, and/or obtained using a disclosed device (such as search tools, compare tools, modeling tools, etc.) can reside in main memory during execution.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells (e.g., myoblasts, etc.) or motoneurons can be obtained from a subject diagnosed with or suspected of having a peripheral neuropathy. The art is familiar with peripheral neuropathies. A description of peripheral neuropathies is provided above. The art is familiar with PNS diseases and disorders, which are also described above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

iv) Device Comprising Detection System Comprising a Laser and a Photo-Detector and a Transducer Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers).

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantlievers. Alternatively or additionally, in some aspects, the neuromuscular junctions are formed on or in guides, for example, channels, that direct the axons of the motoneurons toward the myotubes. In an aspect, a disclosed detection system can comprise (i) a laser and a photo-detector and (ii) a transducer for detecting a change in electrical conductivity of the cantilever. In an aspect, muscle cells or myoblasts can fuse together to form one or more of the myotubes.

In an aspect, a disclosed detection system (e.g., as shown in FIG. 7) can comprise a plurality of linear actuators attached to XY translational stages that control the position of the laser and photo-detector. In an aspect, a detection system comprising a plurality of linear actuators can comprise a digitizer and a computer, wherein the photo-detector is in communication with the digitizer and wherein the digitizer is in communication with the computer. Acceptable computers and computer systems are known to the art and are discussed above. In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, each of the cantilevers of a disclosed device can comprise one or more piezoelectric materials. In an aspect, piezoelectric materials can comprise quartz, bone, sodium tungstate, zinc oxide, and lead zirconate titanate. In an aspect, piezoelectric materials can comprise any piezoelectric material known to the art. A description of both piezoelectricity and piezoelectric materials is provided above.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells.

In an aspect of a disclosed device, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells or motoneurons can be obtained from a subject diagnosed with or suspected of having a peripheral neuropathy. The art is familiar with peripheral neuropathies. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

v) In Vitro Device Comprising Detection System Comprising a Laser and a Photo-Detector Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers). In an aspect, a disclosed detection system can be automated. In an aspect, a disclosed detection system can comprise a laser and a photo-detector.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantlievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed detection system (e.g., as shown in FIG. 7) can comprise a plurality of linear actuators attached to XY translational stages that control the position of the laser and photo-detector. In an aspect, a detection system comprising a plurality of linear actuators can comprise a digitizer and a computer, wherein the photo-detector is in communication with the digitizer and wherein the digitizer is in communication with the computer. Computers are known to the art and are discussed above. In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells or motoneurons can be obtained from a subject diagnosed with or suspected of having a peripheral neuropathy. The art is familiar with peripheral neuropathies. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

vi) In Vitro Device Comprising Detection System Comprising a Transducer

Disclosed herein is a device, comprising at least one cantilever (e.g., cantilevers 100 in FIG. 1) comprising a co-culture of myotubes and motoneurons forming at least one neuromuscular junction, (e.g., neuromuscular junction 150 in FIG. 1) and a detection system (e.g., as shown in FIG. 7). In an aspect, a disclosed detection system can be automated. In an aspect, a disclosed detection system can comprise a transducer for detecting a change in electrical conductivity of the cantilever.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantlievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, each of the cantilevers can comprise one or more piezoelectric materials. In an aspect, piezoelectric materials can comprise quartz, bone, sodium tungstate, zinc oxide, and lead zirconate titanate. In an aspect, piezoelectric materials can comprise any piezoelectric material known to the art. A description of both piezoelectricity and piezoelectric materials is provided above.

In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer. Computers are known to the art and are discussed above.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells or motoneurons can be obtained from a subject diagnosed with or suspected of having a peripheral neuropathy. The art is familiar with peripheral neuropathies. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more trasgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

vii) In Vitro Device Comprising Detection System Comprising a Laser and a Photo-Detector and a Transducer Disclosed herein is a device, comprising at least one cantilever (e.g., cantilevers 100 in FIG. 1) comprising a co-culture of myotubes and motoneurons forming at least one neuromuscular junction, (e.g., neuromuscular junction 150 in FIG. 1) and a detection system. In an aspect, a disclosed detection system can comprise (i) a laser and a photo-detector and (ii) a transducer for detecting a change in electrical conductivity of the cantilever. In an aspect, a disclosed detection system can be automated.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed detection system (e.g., as shown in FIG. 7) can comprise a plurality of linear actuators attached to XY translational stages that control the position of the laser and photo-detector. In an aspect, a detection system comprising a plurality of linear actuators can comprise a digitizer and a computer, wherein the photo-detector is in communication with the digitizer and wherein the digitizer is in communication with the computer. Computers are known to the art and are discussed above. In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect of a disclosed device, each of the cantilevers can comprise one or more piezoelectric materials. In an aspect, piezoelectric materials can comprise quartz, bone, sodium tungstate, zinc oxide, and lead zirconate titanate. In an aspect, piezoelectric materials can comprise any piezoelectric material known to the art. A description of both piezoelectricity and piezoelectric materials is provided above.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed device, at least one of the muscle cells (e.g., myoblasts, etc.) or motoneurons can be obtained from a subject diagnosed with or suspected of having a muscle wasting condition. Muscle wasting conditions are known to the art. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells (e.g., myoblasts, etc.) or motoneurons can be obtained from a subject diagnosed with or suspected of having a peripheral neuropathy. Peripheral neuropathies are known to the art. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more trasgences known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

viii) Device Comprising a First Chamber Comprising Myotubes and a Second Chamber Comprising Motoneurons Disclosed herein is a device comprising at least one cantilever comprising a beam and a base (e.g., cantilevers 100 in FIG. 1), wherein the at least one cantilever comprises one or more neuromuscular junctions (e.g., neuromuscular junctions 150 in FIG. 1) formed by a co-culture of myotubes and motoneurons and positioned on or adjacent to the cantilever beam or base, and an automated detection system. In an aspect, the device can include a plurality of cantilevers. In some aspects, the plurality of cantilevers can refer to all of the cantilevers of the device. In other aspects, the plurality of cantilevers can refer to less than all of the cantilevers of the device (e.g., at least two cantilevers). In an aspect, a detection system can comprise (i) a laser and a photo-detector, (ii) a transducer for detecting a change in electrical conductivity of the cantilever, or both.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, the device can comprise a first chamber and a second chamber, wherein the second chamber is spaced apart from the first chamber. The first chamber can comprise the plurality of cantilevers and the myotubes. The second chamber can comprise the motoneurons. One or more axons can extend from the motoneurons towards the first chamber. In some aspects, the axons extend from the motoneurons and into the first chamber. In some aspects, the axons extend between the motoneurons and the myotubes in the first chamber.

In some aspects, the device comprising a first chamber and a second chamber may further comprise a guide configured to route the axons extending from the motoneurons toward the first chamber. In some aspects, the device can further comprise a barrier arranged between the first chamber and the second chamber, and the guide can comprise one or more channels that are formed through the barrier. In some aspects, the barrier may be formed polydimethylsiloxane (PDMS).

In some aspects the guide may comprise extracellular matrix molecules, chemotactic features, or a combination thereof. For example, the extracellular matrix molecules may be patterned on the surface of the device to promote axon growth in the direction of the first chamber. In some aspects, chemotactic features may include a gradient of molecules the promote axon growth in the direction of the first chamber.

In some aspects, the second chamber can further comprise a plurality of electrodes in contact with the motoneurons. The plurality of electrodes may be arranged, for example, as a microelectrode array.

In an aspect, a disclosed detection system (e.g., as shown in FIG. 7) can comprise a plurality of linear actuators attached to XY translational stages that control the position of the laser and photo-detector. In an aspect, a detection system comprising a plurality of linear actuators can comprise a digitizer and a computer, wherein the photo-detector is in communication with the digitizer and wherein the digitizer is in communication with the computer. Acceptable computers and computer systems are known to the art and are discussed above. In an aspect, a disclosed device can comprise a temperature-controlled stage, wherein the each of the cantilevers is maintained on the temperature-controlled stage, and wherein the temperature-controlled stage comprises one or more electrodes and one or more pulse generators. In an aspect, a disclosed device comprising a temperature-controlled stage can comprise a digitizer and a computer, wherein the one or more pulse generators is in communication with the digitizer, and wherein the digitizer is in communication with the computer.

In an aspect, each of the cantilevers of a disclosed device can comprise one or more piezoelectric materials. In an aspect, piezoelectric materials can comprise quartz, bone, sodium tungstate, zinc oxide, and lead zirconate titanate. In an aspect, piezoelectric materials can comprise any piezoelectric material known to the art. A description of both piezoelectricity and piezoelectric materials is provided above.

In an aspect, each cantilever can be surface-modified or surface-coated. Surface modifications are known to those skilled in the art. In an aspect, a surface modification can comprise (3-Trimethoxysilyl propyl) diethylenetriamine (DETA).

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells.

In an aspect of a disclosed device, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect of a disclosed device, at least one of the muscle cells or motoneurons can be obtained from a subject diagnosed with or suspected of having a peripheral neuropathy. The art is familiar with peripheral neuropathies. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed device, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

C. Methods i) Method of Screening Using a Device Comprising a Laser and a Photo-Detector Disclosed herein is a method of screening for an agent that affects neuromuscular transmission, comprising: (i) recording data from a device comprising a plurality of cantilevers, at least two of the plurality of cantilevers comprising a co-culture of myotubes and motoneurons forming at least one functional neuromuscular junction, and an automated detection system comprising a laser and a photo-detector; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Disclosed herein is a method of screening for an agent that affects neuromuscular transmission, comprising: (i) recording data from a device comprising at least one cantilever comprising a co-culture of myotubes and motoneurons forming at least one functional neuromuscular junction, and an automated detection system comprising a laser and a photo-detector; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed method can comprise confirming the structural integrity of the myotubes. The structural integrity is related to the degree of myotube maturation, so confirming the structural integrity may be used to evaluate the degree of myotube maturation. Confirming the structural integrity of the myotubes can comprise applying electrical stimulation to the co-culture of myotubes and motoneurons. In an aspect, confirming the structure integrity of the myotubes can occur prior to or after recording data from a disclosed device. In an aspect, confirming the structure integrity of the myotubes can occur both prior to and after recording data from a disclosed device. In an aspect, confirming the structure integrity of the myotubes can occur prior to or after contacting one or more agents with the at least one functional neuromuscular junction. In an aspect, confirming the structure integrity of the myotubes can occur both prior to and after contacting one or more agents with the at least one functional neuromuscular junction.

In an aspect, a disclosed method can comprise repeating one or more steps of the method. For example, in an aspect, a disclosed method can comprise repeating all of the steps of the method.

In an aspect, recording data can comprise measuring a change in reflection angle of the laser. In aspect, a change in reflection angle of the laser can indicate a change in the position of a cantilever. In an aspect, measuring a change in reflection angle of the laser can comprise scanning a laser across a tip of each of the plurality of cantilevers for a pre-determined amount of time. In an aspect, a pre-determined amount of time can be user-defined. In an aspect, a pre-determined amount of time can be determined based on experimental design. In an aspect, a pre-determined amount of time can be 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or more seconds.

In an aspect, there can be a delay as the laser moves from cantilever tip to cantilever tip. In an aspect, the delay can be user defined. In an aspect, the delay can be 0.5, 1, 2, 3, 4, 5, 6, 7, 8, 9, 10, or more seconds.

A change in reflection angle of the laser can be used to determine cantilever deflection. For example, in an aspect, cantilever deflection ($\delta$) can be determined using the equation:

$$\delta = \frac{2L}{3}\tan\left[\frac{\theta}{2} - \frac{1}{2}\arctan\left(\tan\theta - \frac{\text{Voltage}}{C_{detector} \times P \times \cos\theta}\right)\right],$$

wherein $C_{detector}$ is the system-specific coefficient relating voltage to laser position on the photo-detector, $\theta$ is the angle of the laser and detector relative to the plane of the cantilever, L is cantilever length, and P is the path length of laser from cantilever tip to detector.

In an aspect, a change in reflection angle of the laser can be used to determine stress produced by the myotube. For example, in an aspect, stress produced by the myotube ($\sigma_c$) can be determined using the equation:

$$\sigma_c = \frac{E_{Si}t_{Si}^3}{6t_f(1-v_{Si})(t_f+t_{Si})}\frac{3\delta}{2L^2} \times \frac{1}{1+\frac{t_f}{t_{Si}}},$$

wherein, assuming a uniform thick film the full width of the cantilever, $E_{Si}$ is the elastic modulus of silicon, $t_{Si}$ is the thicknesses of the cantilever, $t_f$ is the thickness of the myotube, $v_{Si}$ is poison's ratio of silicon, L is cantilever length, and $\delta$ is cantilever deflection.

In an aspect, a change in reflection angle of the laser can be used to determine the force in the myotube. In an aspect, the force in the myotube can be determined using the equation: $F_{myotube} = \sigma_c \times t_f \times w_{Si}$.

In an aspect, the one or more agents of a disclosed method can comprise a metabolic inhibitor, a nutritional supplement, a therapeutic compound, a therapeutic composition, a therapeutic drug, an investigational compound, an investigational composition, an investigational drug, a biosimilar, an agonist, an antagonist, a hormone, a growth factor, a small molecule, a monoclonal antibody, and a combination thereof.

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed method, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed method, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

ii) Method of Screening Using a Device Comprising a Transducer

Disclosed herein is a method of screening for an agent that affects neuromuscular transmission, comprising: (i) recording data from a device comprising a plurality of cantilevers, at least two of the plurality of cantilevers comprising a co-culture of myotubes and motoneurons forming at least one functional neuromuscular junction, and an automated detection system comprising a transducer for detecting a change in electrical conductivity of the cantilever; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Disclosed herein is a method of screening for an agent that affects neuromuscular transmission, comprising: (i) recording data from a device comprising at least one cantilever comprising a co-culture of myotubes and motoneurons forming at least one functional neuromuscular junction, and an automated detection system comprising a transducer for detecting a change in electrical conductivity of the cantilever; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilievers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed method can comprise confirming the structural integrity of the myotubes. Confirming the structural integrity of the myotubes can comprise applying electrical stimulation to the co-culture of myotubes and motoneurons. In an aspect, confirming the structure integrity of the myotubes can occur prior to or after recording data from a disclosed device. In an aspect, confirming the structure integrity of the myotubes can occur both prior to and after recording data from a disclosed device. In an aspect, confirming the structure integrity of the myotubes can occur prior to or after contacting one or more agents with the at least one functional neuromuscular junction. In an aspect, confirming the structure integrity of the myotubes can occur both prior to and after contacting one or more agents with the at least one functional neuromuscular junction. In an aspect, a disclosed method can comprise repeating one or more steps of the method. For example, in an aspect, a disclosed method can comprise repeating all of the steps of the method.

In an aspect, recording data can comprise measuring a change in resistance of a cantilever. In an aspect, measuring a change in resistance of a cantilever can comprise measuring a change in the electrical conductivity of the cantilever. In an aspect, piezoelectric materials can be used to measure a change in electrical conductivity of the cantilever. In an aspect, any piezoelectric material known to the art can be used. A description of both piezoelectricity and piezoelectric materials is provided above. In an aspect, change in resistance of the cantilever can be used to determine cantilever deflection. In an aspect, a change in resistance of the cantilever can be used to determine the force in the myotube force. In an aspect, a change in resistance of the cantilever can be used to determine stress produced by the myotube.

In an aspect, the one or more agents of a disclosed method can comprise a metabolic inhibitor, a nutritional supplement, a therapeutic compound, a therapeutic composition, a therapeutic drug, an investigational compound, an investigational composition, an investigational drug, a biosimilar, an agonist, an antagonist, a hormone, a growth factor, a small molecule, a monoclonal antibody, and a combination thereof.

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed method, at least one of the muscle cells (e.g., myoblasts, etc.) or motoneurons can be obtained from a subject diagnosed with or suspected of having a muscle wasting condition. The art is familiar with muscle wasting conditions. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect, at least one of the muscle cells (e.g., myoblasts, etc.) or motoneurons can be obtained from a subject diagnosed with or suspected of having a peripheral neuropathy. Peripheral neuropathies are known to the art. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed method, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

iii) Method of Screening Using a Device Comprising a Video Camera

Disclosed herein is a method of screening for an agent that affects neuromuscular transmission, comprising: (i) recording data from a device comprising a plurality of cantilevers, at least two of the plurality of cantilevers comprising a co-culture of myotubes and motoneurons forming at least one functional neuromuscular junction, and an automated detection system comprising a video camera for monitoring the movement of one or more myotubes, for example, in response to an electrical stimulus; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Disclosed herein is a method of screening for an agent that affects neuromuscular transmission, comprising: (i) recording data from a device comprising at least one cantilever comprising a co-culture of myotubes and motoneurons forming at least one functional neuromuscular junction, and an automated detection system comprising a video camera for monitoring the movement of one or more myotubes, for example, in response to an electrical stimulus; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed method can comprise confirming the structural integrity of the myotubes. Confirming the structural integrity of the myotubes can comprise applying electrical stimulation to the co-culture of myotubes and motoneurons. In an aspect, confirming the structural integrity of the myotubes can occur prior to or after recording data from a disclosed device. In an aspect, confirming the structure integrity of the myotubes can occur both prior to and after recording data from a disclosed device. In an aspect, confirming the structure integrity of the myotubes can occur prior to or after contacting one or more agents with the at least one functional neuromuscular junction. In an aspect, confirming the structure integrity of the myotubes can occur both prior to and after contacting one or more agents with the at least one functional neuromuscular junction.

In an aspect, a disclosed method can comprise repeating one or more steps of the method. For example, in an aspect, a disclosed method can comprise repeating all of the steps of the method.

In an aspect, recording data can comprise recording a plurality of video frames with the video camera and storing the video frames to the computer for processing. In an aspect, the method may further include processing the plurality of video frames. Processing may include comparing the position of a myotube in a first video frame to the position of the same myotube in a subsequent video frame.

In an aspect, the one or more agents of a disclosed method can comprise a metabolic inhibitor, a nutritional supplement, a therapeutic compound, a therapeutic composition, a therapeutic drug, an investigational compound, an investigational composition, an investigational drug, a biosimilar, an agonist, an antagonist, a hormone, a growth factor, a small molecule, a monoclonal antibody, and a combination thereof.

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed method, at least one of the muscle cells (e.g., myoblasts, etc.) or motoneurons can be obtained from a subject diagnosed with or suspected of having a muscle wasting condition. Muscle wasting conditions are known to the art. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect, at least one of the muscles cells (e.g., myoblasts, etc.) or motoneurons can be obtained from a subject diagnosed with or suspected of having a peripheral neuropathy. Peripheral neuropathies are known to the art. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed method, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

iv) Method of Screening Using a Device Comprising a Laser and a Photo-Detector and a Transducer Disclosed herein is method of screening for an agent that affects neuromuscular transmission, comprising: (i) recording data from a device comprising a plurality of cantilevers, at least two of the plurality of cantilevers comprising a co-culture of myotubes and motoneurons forming at least one functional neuromuscular junction, and an automated detection system comprising (a) a laser and a photo-detector and (b) a transducer for detecting a change in electrical conductivity; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Disclosed herein is method of screening for an agent that affects neuromuscular transmission, comprising: (i) recording data from a device comprising at least one cantilever comprising a co-culture of myotubes and motoneurons forming at least one functional neuromuscular junction, and an automated detection system comprising (a) a laser and a photo-detector and (b) a transducer for detecting a change in electrical conductivity; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In an aspect, a disclosed method can comprise confirming the structural integrity of the myotubes. Confirming the structural integrity of the myotubes can comprise applying electrical stimulation to the co-culture of myotubes and motoneurons. In an aspect, confirming the structure integrity of the myotubes can occur prior to or after recording data from a disclosed device. In an aspect, confirming the structure integrity of the myotubes can occur both prior to and after recording data from a disclosed device. In an aspect, confirming the structure integrity of the myotubes can occur prior to or after contacting one or more agents with the at least one functional neuromuscular junction. In an aspect, confirming the structure integrity of the myotubes can occur both prior to and after contacting one or more agents with the at least one functional neuromuscular junction.

In an aspect, a disclosed method can comprise repeating one or more steps of the method. For example, in an aspect, a disclosed method can comprise repeating all of the steps of the method.

In an aspect, recording data can comprise measuring a change in reflection angle of the laser and measuring a change in resistance of a cantilever. For example, in an aspect, measuring a change in resistance of a cantilever can comprise measuring a change in the electrical conductivity of the cantilever. In an aspect, piezoelectric materials can be used to measure a change in electrical conductivity of the cantilever. In an aspect, any piezoelectric material known to the art can be used. A description of both piezoelectricity and piezoelectric materials is provided above. In an aspect, a change in resistance of the cantilever can be used to determine cantilever deflection. In an aspect, a change in resistance of the cantilever can be used to determine the force in the myotube force. In an aspect, a change in resistance of the cantilever can be used to determine stress produced by the myotube. For example, in an aspect, a change in reflection angle of the laser can indicate a change in the position of a cantilever. In an aspect, measuring a change in reflection angle of the laser can comprise scanning a laser across a tip of each of the plurality of cantilevers for a pre-determined amount of time. In an aspect, a pre-determined amount of time can be user-defined. In an aspect, a pre-determined amount of time can be determined based on experimental design. In an aspect, a pre-determined amount of time can be 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or more seconds. In an aspect, there can be a delay as the laser moves from cantilever tip to cantilever tip. In an aspect, the delay can be user defined. In an aspect, the delay can be 0.5, 1, 2, 3, 4, 5, 6, 7, 8, 9, 10, or more seconds.

In an aspect, a change in reflection angle of the laser can be used to determine cantilever deflection. For example, in an aspect, cantilever deflection ($\delta$) can be determined using the equation:

$$\delta = \frac{2L}{3}\tan\left[\frac{\theta}{2} - \frac{1}{2}\arctan\left(\tan\theta - \frac{\text{Voltage}}{C_{detector} \times P \times \cos\theta}\right)\right],$$

wherein $C_{detector}$ is the system-specific coefficient relating voltage to laser position on the photo-detector, $\theta$ is the angle of the laser and detector relative to the plane of the cantilever, L is cantilever length, and P is the path length of laser from cantilever tip to detector.

In an aspect, a change in reflection angle of the laser can be used to determine stress produced by the myotube. For example, in an aspect, stress produced by the myotube ($\sigma_c$) can be determined using the equation:

$$\sigma_c = \frac{E_{Si} t_{Si}^3}{6 t_f (1 - v_{Si})(t_f + t_{Si})} \frac{3\delta}{2L^2} \times \frac{1}{1 + \frac{t_f}{t_{Si}}},$$

wherein, assuming a uniform thick film the full width of the cantilever, $E_{Si}$ is the elastic modulus of silicon, $t_{Si}$ is the thicknesses of the cantilever, $t_f$ is the thickness of the myotube, $v_{Si}$ is poison's ratio of silicon, L is cantilever length, and $\delta$ is cantilever deflection.

In an aspect, a change in reflection angle of the laser can be used to determine the force in the myotube. In an aspect, the force in the myotube can be determined using the equation: $F_{myotube} = \sigma_c \times t_f \times w_{Si}$.

In an aspect, the one or more agents of a disclosed method can comprise a metabolic inhibitor, a nutritional supplement, a therapeutic compound, a therapeutic composition, a therapeutic drug, an investigational compound, an investigational composition, an investigational drug, a biosimilar, an agonist, an antagonist, a hormone, a growth factor, a small molecule, a monoclonal antibody, and a combination thereof.

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed method, at least one of the muscle cells (e.g., myoblasts, etc.) or motoneurons can be obtained from a subject diagnosed with or suspected of having a muscle wasting condition. Muscle wasting conditions are known to the art. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect, at least one of the muscles cells (e.g., myoblasts, etc.) or motoneurons can be obtained from a subject diagnosed with or suspected of having a peripheral neuropathy. Peripheral neuropathies are known to the art. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed method, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

v) Method of Screening Using a Device Comprising a First Chamber Comprising Myotubes and a Second Chamber Comprising Motoneurons Disclosed herein is method of screening for an agent that affects neuromuscular transmission, comprising: (i) recording data from a device comprising a plurality of cantilevers, at least two of the plurality of cantilevers comprising a co-culture of myotubes and motoneurons forming at least one functional neuromuscular junction, and an automated detection system comprising (a) a laser and a photo-detector, (b) a transducer for detecting a change in electrical conductivity, or both; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Disclosed herein is method of screening for an agent that affects neuromuscular transmission, comprising: (i) recording data from a device comprising at least one cantilever comprising a co-culture of myotubes and motoneurons forming at least one functional neuromuscular junction, and an automated detection system comprising (a) a laser and a photo-detector, (b) a transducer for detecting a change in electrical conductivity, or both; (ii) contacting the at least one functional neuromuscular junction with one or more agents; and (iii) recording data generated using the device; wherein a change in the data obtained in step (iii) when compared to the data obtained in step (i) indicates that the one or more agents affects neuromuscular transmission.

Neuromuscular junctions can be formed anywhere on the device where the motoneurons and the myotubes come into contact. For example, the neuromuscular junctions can be formed on or adjacent to the cantilevers. In some aspects, the neuromuscular junctions are formed on the plurality of cantilevers. Alternatively or additionally, in some aspects, the neuromuscular junctions are formed at the base of the cantilevers. Alternatively or additionally, in some aspects, the neuromuscular junctions are formed on or in guides, for example, channels, that direct the axons of the motoneurons toward the myotubes. In an aspect, muscle cells or myoblasts can fuse together to form one or more of the myotubes.

In some aspects, the device further comprises a first chamber and a second chamber spaced apart from the first chamber. The first chamber comprises the plurality of cantilevers and the myotubes, the second chamber comprises the motoneurons. One or more axons extend from the motoneurons and toward the first chamber. In some aspects, the axons extend from the motoneurons and into the first chamber. In some aspects, the axons extend between the motoneurons and the myotubes in the first chamber. In some aspects, the motoneurons can be in contact with a plurality of electrodes.

In an aspect, a disclosed method can comprise confirming the structural integrity of the myotubes. Confirming the structural integrity of the myotubes can comprise applying electrical stimulation to the co-culture of myotubes and motoneurons. In an aspect, confirming the structural integrity of the myotubes can occur prior to or after recording data from a disclosed device. In an aspect, confirming the structure integrity of the myotubes can occur both prior to and after recording data from a disclosed device. In an aspect, confirming the structure integrity of the myotubes can occur prior to or after contacting one or more agents with the at least one functional neuromuscular junction. In an aspect, confirming the structure integrity of the myotubes can occur both prior to and after contacting one or more agents with the at least one functional neuromuscular junction.

In an aspect, a disclosed method can comprise repeating one or more steps of the method. For example, in an aspect, a disclosed method can comprise repeating all of the steps of the method.

In an aspect, recording data can comprise measuring a change in reflection angle of the laser and measuring a change in resistance of a cantilever. For example, in an aspect, measuring a change in resistance of a cantilever can comprise measuring a change in the electrical conductivity of the cantilever. In an aspect, piezoelectric materials can be used to measure a change in electrical conductivity of the cantilever. In an aspect, any piezoelectric material known to the art can be used. A description of both piezoelectricity and piezoelectric materials is provided above. In an aspect, a change in resistance of the cantilever can be used to determine cantilever deflection. In an aspect, a change in resistance of the cantilever can be used to determine the force in the myotube force. In an aspect, a change in resistance of the cantilever can be used to determine stress produced by the myotube. For example, in an aspect, a change in reflection angle of the laser can indicate a change in the position of a cantilever. In an aspect, measuring a change in reflection angle of the laser can comprise scanning a laser across a tip of each of the plurality of cantilevers for a pre-determined amount of time. In an aspect, a pre-determined amount of time can be user-defined. In an aspect, a pre-determined amount of time can be determined based on experimental design. In an aspect, a pre-determined amount of time can be 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or more seconds. In an aspect, there can be a delay as the laser moves from cantilever tip to cantilever tip. In an aspect, the delay can be user defined. In an aspect, the delay can be 0.5, 1, 2, 3, 4, 5, 6, 7, 8, 9, 10, or more seconds.

In an aspect, a change in reflection angle of the laser can be used to determine cantilever deflection. For example, in an aspect, cantilever deflection (δ) can be determined using the equation:

$$\delta = \frac{2L}{3}\tan\left[\frac{\theta}{2} - \frac{1}{2}\arctan\left(\tan\theta - \frac{\text{Voltage}}{C_{detector} \times P \times \cos\theta}\right)\right],$$

wherein $C_{detector}$ is the system-specific coefficient relating voltage to laser position on the photo-detector, θ is the angle of the laser and detector relative to the plane of the cantilever, L is cantilever length, and P is the path length of laser from cantilever tip to detector.

In an aspect, a change in reflection angle of the laser can be used to determine stress produced by the myotube. For example, in an aspect, stress produced by the myotube ($\sigma_c$) can be determined using the equation:

$$\sigma_c = \frac{E_{Si}t_{Si}^3}{6t_f(1-v_{Si})(t_f+t_{Si})}\frac{3\delta}{2L^2} \times \frac{1}{1+\frac{t_f}{t_{Si}}},$$

wherein, assuming a uniform thick film the full width of the cantilever, $E_{Si}$ is the elastic modulus of silicon, $t_{Si}$ is the thicknesses of the cantilever, $t_f$ is the thickness of the myotube, $v_{Si}$ is poison's ratio of silicon, L is cantilever length, and δ is cantilever deflection.

In an aspect, a change in reflection angle of the laser can be used to determine the force in the myotube. In an aspect, the force in the myotube can be determined using the equation: $F_{myotube} = \sigma_c \times t_f \times w_{Si}$.

In an aspect, the one or more agents of a disclosed method can comprise a metabolic inhibitor, a nutritional supplement, a therapeutic compound, a therapeutic composition, a therapeutic drug, an investigational compound, an investigational composition, an investigational drug, a biosimilar, an agonist, an antagonist, a hormone, a growth factor, a small molecule, a monoclonal antibody, and a combination thereof.

In an aspect, the muscle cells can be human muscle cells (e.g., myoblasts, etc.) or the motoneurons can be human motoneurons. In an aspect, both the muscle cells and motoneurons can be human. In an aspect, the muscle cells can be rat muscle cells (e.g., myoblasts, etc.) or the motoneurons can be rat motoneurons. In an aspect, both the muscle cells and the motoneurons can be rat. In an aspect, the muscle cells can be derived from stem cells. In an aspect, the motoneurons can be derived from stem cells. In an aspect, both the muscle cells and the motoneurons can be derived from stem cells. In an aspect, stem cells can be human stem cells or rat stem cells.

In an aspect of a disclosed method, at least one of the muscle cells (e.g., myoblasts, etc.) or motoneurons can be obtained from a subject diagnosed with or suspected of having a muscle wasting condition. Muscle wasting conditions are known to the art. As known to the art, a muscle wasting condition can be considered a peripheral nervous system disease or disorder. A description of muscle wasting conditions is provided above. In an aspect, if at least one muscle cell is obtained from a subject diagnosed with or suspected of having a muscle wasting condition, then at least one motoneuron can be obtained from a healthy subject or a subject not diagnosed with or not suspected of having a muscle condition. In an aspect, if at least one motoneuron is obtained from a subject diagnosed with or suspected of having a muscle wasting condition, then at least one muscle cell can be obtained from a healthy subject or a subject not diagnosed with or not suspected of having a muscle condition. In an aspect, if at least one muscle cell is obtained from a subject diagnosed with or suspected of having a muscle wasting condition, then at least one motoneuron can be obtained from a subject diagnosed with or suspected of having a muscle wasting condition. In an aspect, if at least one muscle cell is obtained from a healthy subject or a subject not diagnosed with or not suspected of having a muscle condition, then at least one motoneuron can be obtained from a healthy subject or a subject not diagnosed with or not suspected of having a muscle condition.

In an aspect, at least one of the muscles cells (e.g., myoblasts, etc.) or motoneurons can be obtained from a subject diagnosed with or suspected of having a peripheral neuropathy. Peripheral neuropathies are known to the art. A description of peripheral neuropathies is provided above. In an aspect, if at least one muscle cell is obtained from a subject diagnosed with or suspected of having a peripheral neuropathy, then at least one motoneuron can be obtained from a healthy subject or a subject not diagnosed with or not suspected of having a peripheral neuropathy. In an aspect, if at least one motoneuron is obtained from a subject diagnosed with or suspected of having a peripheral neuropathy, then at least one muscle cell can be obtained from a healthy subject or a subject not diagnosed with or not suspected of having a peripheral neuropathy. In an aspect, if at least one muscle cell is obtained from a subject diagnosed with or suspected of having a peripheral neuropathy, then at least one motoneuron can be obtained from a subject diagnosed with or suspected of having a peripheral neuropathy. In an aspect, if at least one muscle cell is obtained from a healthy subject or a subject not diagnosed with or not suspected of having a peripheral neuropathy, then at least one motoneuron can be obtained from a healthy subject or a subject not diagnosed with or not suspected of having a peripheral neuropathy.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect of a disclosed method, the co-culture can be maintained in a serum-free medium. Mediums, including serum-free mediums, are known to the skilled person in the art and are discussed above. In an aspect, a serum-free medium can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

D. Kits

Disclosed herein is a kit, comprising a disclosed device, muscle cells and motoneurons, and serum-free medium. In an aspect, a disclosed kit can comprise instructions for assembling and/or using a disclosed device, instructions for culturing muscle cells and motoneurons, instructions for generating and/or using a serum free medium, and/or instructions for using a disclosed device to record physiological data. In an aspect, muscle cells or myoblasts can fuse together to form one or more of the myotubes.

Disclosed herein is a kit, comprising a disclosed device, muscle cells (e.g., myoblasts, etc.) and motoneurons, serum-free medium, and instructions for assembling and/or using a disclosed device, instructions for culturing muscle cells and motoneurons, instructions for generating and/or using a serum free medium, and/or instructions for using a disclosed device to record physiological data. In an aspect, muscle cells or myoblasts can fuse together to form one or more myotubes.

In an aspect, a disclosed device can be any device disclosed herein. For example, in an aspect, a disclosed device of a disclosed kit can comprise at least one cantilever and a detection system. In some aspects, the disclosed device can comprise a plurality of cantilevers. In some aspects, the disclosed device can include a first chamber and a second chamber spaced from the first chamber. The first chamber can comprise the plurality of cantilevers and the myotubes. The second chamber can comprise the motoneurons. One or more axons can extend from the motoneurons towards the first chamber. In some aspects, the axons extend from the motoneurons and into the first chamber. In some aspects, the axons extend between the motoneurons and the myotubes in the first chamber. In an aspect, a disclosed detection system of a disclosed kit (i) can be automated, (ii) can comprise a laser and a photo-detector, and/or (iii) can comprise a laser and a photo-detector and a transducer.

In an aspect, each cantilever of a disclosed kit can comprise one or more piezoelectric materials. A description of both piezoelectricity and piezoelectric materials is provided above.

In an aspect, each cantilever of a disclosed kit can be surface-modified or surface-coated, such as, for example, a modification or coating comprising (3-Trimethoxysilyl propyl) diethylenetriamine (DETA). Surface modifications are known to those skilled in the art and are described above.

In an aspect, the muscle cells (e.g., myoblasts, etc.) and/or motoneurons of a disclosed kit can be human. In an aspect, the muscle cells and/or motoneurons of a disclosed kit can be rat. In an aspect, at least one of the muscle cells and/or motoneurons of a disclosed kit can be obtained from a subject diagnosed with or suspected of having a muscle wasting condition. The art is familiar with muscle wasting conditions, which are described above. In an aspect, at least one of the muscle cells and/or motoneurons of a disclosed kit can be obtained from a subject diagnosed with or suspected of having a peripheral neuropathy. The art is familiar with peripheral neuropathies, which are described above.

In an aspect, one or more of muscle cells (e.g., myoblasts that fuse to form one or more myotubes) and/or one or more motoneurons can be obtained from a transgenic animal. For example, in an aspect, a transgenic animal can comprise a transgene known to or suspected of having a role in the etiology of a muscle wasting condition or a peripheral neuropathy. In an aspect, a transgenic animal can comprise one or more transgenes known to or suspected of having a role in the etiology of a muscle wasting condition or a peripheral neuropathy.

In an aspect, a serum-free medium of a disclosed kit can comprise one or more of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. In an aspect, a serum-free medium of a disclosed kit can comprise all of the following: neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP. Components such as neurobasal medium, B27, and Glutamax are known to the art and described above.

E. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

i) Experimental Materials and Methods a. Device Fabrication

Chips containing an array of individual cantilevers were produced from silicon-on-insulator (SOI) wafers fabricated using previously published methods (Das et al., 2007; Wilson et al., 2010, each of which is incorporated herein by reference in its entirety for teachings related to cantilever fabrication). Briefly, to produce the devices, 100 mm SOI wafers with a 4 µm thick device layer and buried oxide layer of 1 µm were used. The cantilever structures were produced in the device layer by patterning with photolithography methods using S1818 photoresist and etching using deep reactive ion etching (DRIE). The buried oxide layer acted as an etch stop. A 1 µm thick layer of silicon dioxide was deposited on top of each of the cantilevers using plasma enhanced chemical vapor deposition (PECVD) so as to protect the cantilevers during processing. The backside of the wafer was similarly patterned and etched using a second mask. When the silicon beneath the cantilevers was removed, a large window underneath an array of cantilevers remained. The buried oxide layer and oxide layer protecting the cantilevers were removed using a buffered oxide etch solution. The resulting structures were freestanding, bare silicon cantilevers that could be imaged from above and interrogated with a laser from below. The chips were separated by cleaving along perforated edge lines produced during the backside etch. Dimensions of the cantilevers were verified using scanning electron microscopy.

Some embodiments of the device have a separate chamber including a plurality of microelectrodes or a microelectrode array. The MEAs may be obtained commercially and prepared for cell culture. Foe example, MEA's containing sixty (60) electrodes (10 µm diameter) (Multichannel Systems, Germany) were cleaned by soaking the arrays in a detergent solution for 2 hours followed by sonication for 10 minutes. The arrays were then oxygen plasma cleaned for 20 minutes. Surface modification was completed by incubation of the MEAs in a 3 mM PEG silane, 2-[Methoxypoly(ethyleneoxy) propyl]trimethoxysilane (MW=460-590, Gelest), solution in toluene, with 37% concentrated HCl added to achieve a final value of 0.08% (0.8 mL HCl/L), for 45 minutes at room temperature. The arrays were then rinsed once in toluene, twice in ethanol, twice in water and sonicated in water for 2 minutes to remove the non-covalently linked material (Popat et al., 2004). The arrays were air dried with nitrogen and stored in a dessicator overnight.

Some embodiments of the device may include a barrier separating the first chamber with the cantilevers from the second chamber with the plurality of electrodes. The barrier may include microchannels for guiding axons that extend from the motoneurons toward the first chamber and the myotubes. The microchannels may also be formed by photolithographic techniques.

b. DETA Surface Modification

To promote cell adhesion to the cantilevers and control glass coverslips, the surfaces were coated with an amine-terminated alkylsilane, (3-Trimethoxysilyl propyl) diethylenetriamine (DETA) (United Chemical Technologies, Bristol, Pa.) using methods published previously (Das et al., 2010; Guo et al., 2010; Wilson et al., 2010, each of which is incorporated herein by reference in its entirety for teachings related to DETA surface modification). DETA is an analog of spermidine; a natural polyamine known to promote long term survival of cells in vitro (Eisenberg et al., 2009; Kaeberlein 2009). This surface coating has been used extensively to modify surfaces for the culture of a variety of cell types (Das et al., 2010; Guo et al., 2010; Das et al., 2007; Wilson et al., 2010; Das et al., 2006; Rumsey et al., 2010; Rumsey et al., 2009).

The cantilevers and glass coverslips were acid washed in baths of concentrated HCl in methanol (1:1) and concentrated $H_2SO_4$, followed by rinsing in boiling de-ionized water and oven drying. The surfaces were silanized using a solution of 0.1% DETA-silane in toluene, which was heated to 70° C. for 30 minutes. To remove any unreacted silane, the surfaces were subjected to a series of toluene rinses with reheating to 70° C. for 30 minutes in fresh toluene. The surfaces were oven cured at 110° C. for 2 hours and stored in a desiccator until use. The surface coatings were verified using X-ray photoelectron spectroscopy and contact angle goniometry.

c. Cell Culture

All incubations were performed in a 37° C., 5% $CO_2$ incubator. Muscle cells were isolated from E18 Sprague-Dawley rat fetuses and motoneurons were isolated from E15 Sprague-Dawley rat fetuses. Pregnant rats were then euthanized by exposure to an excess of $CO_2$.

Muscle tissue was dissected from the hind limbs of E18 fetuses and transferred to a 0.25% trypsin solution (Life Technologies, Grand Island, N.Y.). To dissociate the tissue fragments into a single cell suspension, this solution was placed in a shaking water bath set at 37° C. and 100 rpm for 25 minutes. The cell suspension was triturated and run through a 100 μm mesh filter in order to remove any un-dissociated tissue fragments. The cells were then plated onto an uncoated, 100 mm dish and left for 30 minutes at room temperature. After this time, the non-adherent cells were collected in the supernatant and the adherent cells were discarded. Because fibroblasts adhere more rapidly to tissue culture plastic and therefore are selected out, this step enriched the myogenic precursor (myoblast) population, (Machaida et al., 2004). The muscle cell suspension was spun at 300 g for 5 minutes and the pelleted cells re-suspended in a defined muscle proliferation medium developed previously (Table 1). Cells were plated onto DETA coated silicon cantilever chips at an initial density of 2000 cells/mm² and maintained for 4 days in vitro (DIV). At this point the proliferation medium was replaced with a differentiation medium to promote myoblast fusion into primary myotubes. The differentiation medium contained NBActiv4 (Brain Bits, Springfield, Ill.)+1% antibiotic/anti-mycotic (i.e., Amphotericin B, Penicillin, and Streptomycin mixture at 100× concentration) (Life Technologies). As described in Brewer et al., 2008, NbActiv4™ comprises all of the ingredients in Neurobasal™, B27™, and Glutamax™, and can also comprise creatine, estrogen, and cholesterol. Cells were maintained in this medium for another 3 days in vitro (DIV).

TABLE 1

Components of Defined Muscle Proliferation Medium

| Component | Concentration | Company (Catalog No.) |
|---|---|---|
| Neurobasal medium | N/A | Life Technologies (21103-049) |
| B27 (50x) | 1x | Life Technologies (17504044) |
| Glutamax (100x) | 1x | Life Technologies (35050061) |
| G5 supplement | 1x | Life Technologies (17503-012) |
| Glial-Derived Neurotrophic Factor | 20 ng/mL | Cell Sciences (CRG400B) |
| Brain-Derived Neurotrophic Factor | 20 ng/mL | Cell Sciences (CRB600B) |
| Ciliary Neurotrophic Factor | 40 ng/mL | Cell Sciences (CRC400A) |
| Neurotrophin-3 | 20 ng/mL | Cell Sciences (CRN500B) |
| Neurotrophin-4 | 20 ng/mL | Cell Sciences (CRN501B) |
| Acidic Fibroblast Growth Factor | 25 ng/mL | Life Technologies (13241-013) |
| Vascular Endothelial Growth Factor | 20 ng/mL | Life Technologies (P2654) |
| Cardiotrophin-1 | 20 ng/mL | Cell Sciences (CRC700B) |
| Heparin Sulphate | 100 ng/mL | Sigma (D9809) |
| Leukemia Inhibitory Factor | 20 ng/mL | Sigma (L5158) |
| Vitronectin | 100 ng/mL | Sigma (V0132) |

Spinal cords were dissected from E15 fetuses and the dorsal horn carefully removed using a fine surgical blade (Fine Science Tools, Foster City, Calif.). The isolated cords were transferred to a 0.25% trypsin solution and incubated for 12 minutes. The tissue was then carefully triturated to dissociate it into a single cell suspension using a P1000 pipette tip. The resulting cell suspension was layered onto a 4 mL step gradient (Optiprep (Sigma-Aldrich, St. Louis, Mo.) diluted 0.505:0.495 (v/v) with Hibernate E (Brain Bits)+GlutaMAX™ (Life Technologies)+AB/AM+B27 (Life Technologies) and then made up to 15%, 20%, 25% and 35% solutions (v/v) in Hibernate E+AB/AM+B27 and spun at 200 g for 15 minutes at 4° C. Motoneurons, with large somas, formed the upper-most band and were collected using a P1000 pipette before being spun again at 200 g for 5 minutes. The resulting cell pellet was then re-suspended in a co-culture medium described in Table 2. This co-culture medium has been used to generate ventral horn cultures, enriched for motoneurons (Das et al., 2010).

TABLE 2

Components of Co-Culture Medium

| Component | Concentration | Company (Catalog No.) |
|---|---|---|
| Neurobasal medium | N/A | Life Technologies (21103-049) |
| B27 (50x) | 1x | Life Technologies (17504044) |
| Glutamax (100x) | 1x | (35050061) |
| Glial-Derived Neurotrophic Factor | 10 ng/mL | Cell sciences (CRG400B) |
| Brain-Derived Neurotrophic Factor | 20 ng/mL | Cell sciences (CRB600B) |
| Ciliary neurotrophic factor | 5 ng/mL | Cell sciences (CRC400A) |
| Insulin-like growth factor-1 | 25 ng/mL | Sigma (I2656) |
| Neurotrophin-3 | 20 ng/mL | Cell sciences (CRN500B) |
| Neurotrophin-4 | 20 ng/mL | Cell sciences (CRN501B) |
| Mouse laminin | 1 µg/mL | Life Technologies (23017-015) |
| cAMP | 1 µM | Sigma (A9501) |

Muscle cultures, maintained for 3 days in vitro in muscle differentiation medium, were aspirated and were fed with co-culture medium. Isolated ventral horn cells were then plated directly on top of the cultured muscle cells at a density of 250 cells/mm$^2$. Co-cultures were maintained in the co-culture medium for another 7 days in vitro, with half the medium replaced every 2-3 days. Following 7 days in co-culture, the growth factors in the medium were slowly diluted out by replacing half the medium every 2 days with NBActiv4+1% AB/AM. Co-cultures were analyzed for evidence of neuromuscular transmission following 13-14 days in vitro (i.e., a total culture time of 20-21 days in vitro).

Muscle-only control cultures were established in parallel to all co-cultures examined. These cultures were subjected to identical culture parameters minus the plating of ventral horn cells after 7 days in vitro.

d. Electrophysiological Recordings

After 11-13 days in vitro, electrophysiological properties of ventral horn motoneurons were investigated using whole-cell patch-clamp recording techniques. Glass coverslips with cultured ventral horn cells were transferred to a recording chamber located on the stage of a Zeiss Axioscope 2FS Plus upright microscope. Motoneurons were identified visually under an infrared differential interference contrast (DIC) video-microscope. The largest multipolar cells (15-20 µm diameters) with bright somas were identified as motoneurons. Borosilicate glass patch pipettes (BF 150-86-10; Sutter Instrument Company) with a resistance of 6-10 MΩ were made using a Sutter P97 pipette puller (Sutter Instrument Company). Current-clamp and voltage-clamp recordings were made using a Multiclamp 700 A amplifier (Axon instruments). The pipette (intracellular) solution contained 1 mM EGTA, 140 mM K-gluconate, 2 mM MgCl$_2$, 2 mM Na$_2$ATP and 10 mM HEPES (pH 7.2). NBActiv4 medium plus 10 mM HEPES (pH 7.2) was used as the extracellular solution.

After the formation of a giga-ohm seal and membrane puncture, the cell capacitance was compensated. Signals were filtered at 3 kHz and sampled at 20 kHz using a Digidata 1322A interface (Axon Instruments). Data recording and analysis were performed with pClamp8 software (Axon Instruments). Membrane potentials were corrected by subtraction of a 15 mV tip potential, which was calculated using Axon's pClamp8 program. Depolarization-evoked inward and outward currents were examined in voltage-clamp mode. Depolarization-evoked action potentials were examined in current-clamp mode and induced using 1 second depolarizing current injections from a −70 mV holding potential. Action potentials elicited in response to 200 µM glutamate (an excitatory neurotransmitter) (Sigma-Aldrich) injection into the extracellular solution were likewise measured in current-clamp mode from a −70 mV holding potential.

e. Automated Myotube Contraction Detection System

Myotube contraction was recorded and characterized via measurement of cantilever deflection using an automated system. In this system, cantilevers supporting co-cultured myotubes and motoneurons were inserted into a transparent culture dish fitted into a modified upright Olympus BX51WI electrophysiology microscope. The culture dish was filled with NBActiv4 medium (+10 mM HEPES) to maintain the cells during the analysis. A heated culture dish system (Delta T, Bioptechs, Butler, Pa.) was incorporated into the stage to maintain the culture at 37° C. throughout the analysis.

The automated system consisted of a Helium Neon laser beam that was automatically scanned across the tips of each cantilever at a 30° angle relative to the plane of the cantilever. A quadrant photo-detector module was also moved to detect the reflected beam. Four stepper motor-driven linear actuators attached to XY translational stages controlled the positions of the laser and photo-detector, with each unit mounted to an XY stage and requiring an actuator for the X and Y translation directions. A temperature-controlled stage was incorporated into the unit to maintain the cells at physiological temperature. Stainless steel electrodes were mounted inside the stage dish at a separation distance of 15 mm. To allow the system to produce field stimulation of myotubes when appropriate, the electrodes were connected to a pulse generator (A-M systems, Sequim, Wash.), which was capable of producing field stimulation pulses of varying intensity, frequency, and waveform.

Software was written in National Instruments LabVIEW to control the linear actuators that scanned across the cantilevers. To calibrate the system, the laser and photo-detector positions were automatically set to the approximate locations for each of four characteristic cantilevers that defined the array: the two end cantilevers on each of the two rows. Minor manual adjustment was required to precisely position the laser beam at the tip of the cantilever and to position the detector such that the reflected beam hit the center of the photo-detector. After these four positions were established for a particular cantilever chip, the LabVIEW program linearly interpolated the positions of the remaining cantilevers. The written software allowed for only minor manual adjustment of four positions to define all thirty-two cantilever positions. Slight modifications to the software to extend this system to many more cantilevers in the array would be trivial.

After automatically determining the positions of each cantilever in the array, the LabVIEW program scanned the laser and detector across the entire array of cantilevers, stopping the laser and detector at each cantilever tip for a user-defined period of time, set in the graphical user interface. Functions were written in the program to allow for the interrogation of a user-specified subset of cantilevers to maximize the collection of pertinent data.

The photo-detector and pulse stimulator were connected through an Axon Instruments 1440 digitizer (Molecular Devices, Union City, Calif.) to a computer running Axo-Scope 10.0. The change in position of the reflected laser beam on the photo-detector was recorded in AxoScope, along with the timing of any electrical field pulses produced by the pulse generator.

f. Measurement of Myotube Contraction in Response to Neuronal Stimulation

Broad field electrical stimulation was first used to verify the contractile ability of the cultured myotubes. Cultures were subjected to a 3 V, 40 ms pulse at a frequency of 1 Hz, and the cantilevers were scanned for 5 seconds each to identify those with active myotubes. A representative trace demonstrating the response of cultured myotubes to this stimulation is provided in FIG. 1. Across all experimental conditions, a successful contractile response was taken as any peak equal to or larger than 0.1 V.

The electrical stimulus was then switched off and the active cantilevers scanned again in order to observe the rate of spontaneous contraction. This condition was followed by bath application of 200 µM glutamate to stimulate motoneuron firing, and the cantilevers were again scanned for evidence of contractile activity. A second application of glutamate was made following addition of 12.5 µM D-tubocurarine (Sigma-Aldrich) to block neuromuscular transmission. The cantilevers were again scanned for contractile activity following this treatment. Finally, cantilevers were subjected to the same broad-field electrical stimulation as was used initially and scanned for contractile activity to verify that the treatments had not destroyed the contractile capability of the myotube or caused the cells to detach.

g. Calculation of Force Generation

Conversion of photo-detector readings to cantilever deflection and myotube force were performed using a modified Stoney's equation (Wilson et al., 2010). Briefly, the photo-detector measured the changes in cantilever bending-induced laser deflection (reported in Volts) from which the deflection of the cantilever tip was calculated. Equations (1) and (2) are restated equations (see, e.g., Wilson et al., 2010) for cantilever tip deflection ($\delta$) and stress produced by the myotube, assuming a uniform thick film the full width of the cantilever ($\sigma_c$). The system parameters used in these equations were the system-specific coefficient relating voltage to laser position on the photo-detector ($C_{detector}$), the angle of the laser and detector relative to the plane of the cantilever (A), the elastic modulus of silicon ($E_{Si}$), the thicknesses of the cantilever ($t_{Si}$) and myotube ($t_f$), poison's ratio of silicon ($v_{Si}$), cantilever length (L), path length of laser from cantilever tip to detector (P), and the width of the cantilever ($w_{si}$).

$$\delta = \frac{2L}{3}\tan\left[\frac{\theta}{2} - \frac{1}{2}\arctan\left(\tan\theta - \frac{Voltage}{C_{detector} \times P \times \cos\theta}\right)\right] \quad (1)$$

$$\sigma_c = \frac{E_{Si}t_{Si}^3}{6t_f(1-v_{Si})(t_f+t_{Si})} \frac{3\delta}{2L^2} \times \frac{1}{1+\frac{t_f}{t_{Si}}} \quad (2)$$

In Equation 2, the myotube was approximated as a uniform film. Therefore, the force in the myotube was equal to the force in the film, which leads to Equation 3, by equating the calculation of force from stress and the assumed cross sectional area that was used for the application of Stoney's equation.

$$F_{myotube} = \sigma_c \times t_f \times w_{Si} \quad (3)$$

h. Detection of Myotube Movement Using a Video Camera

Figure 13:
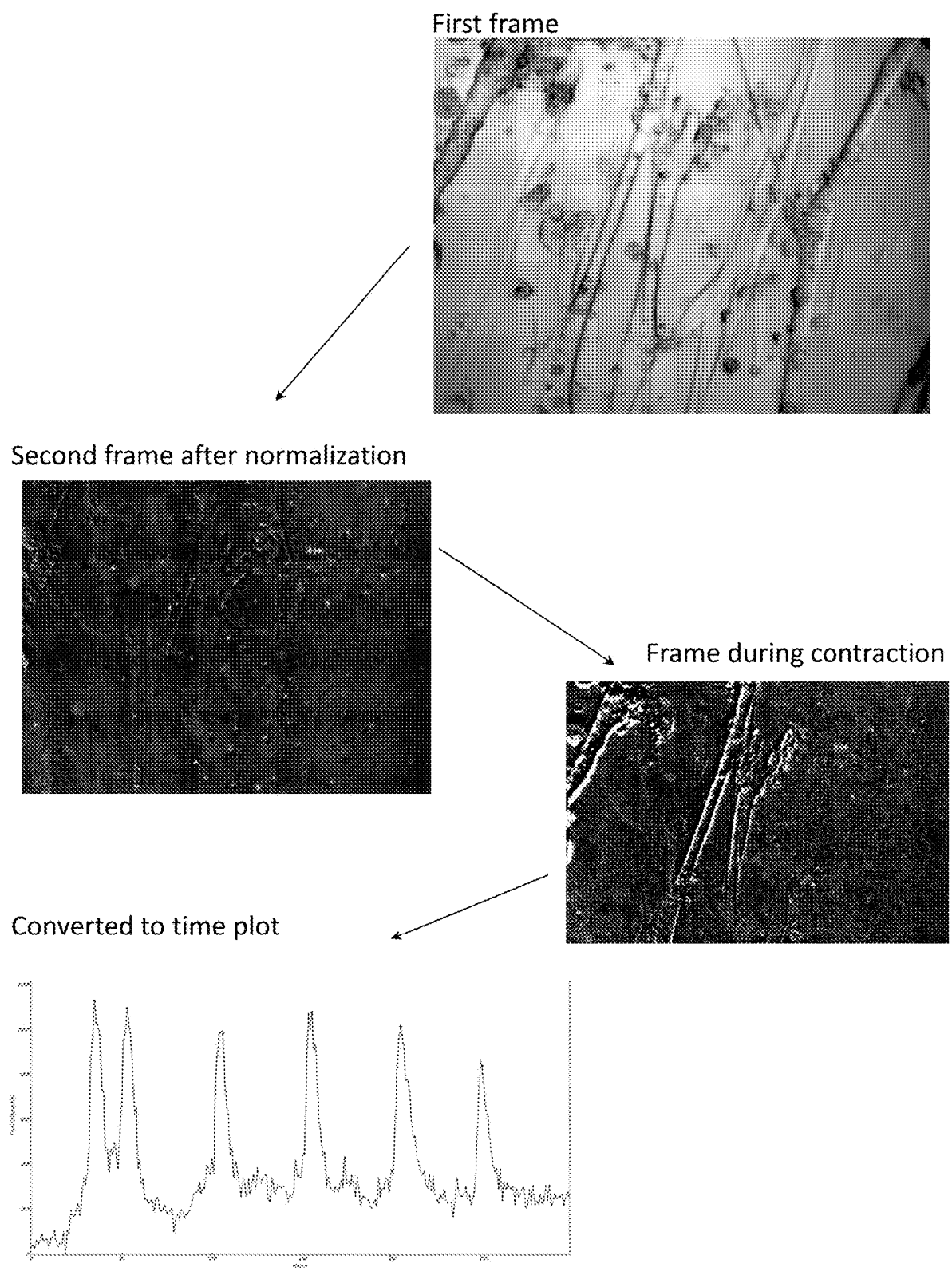
FIG. 13 shows a method using a device comprising a video camera. Movement of the myotubes may be monitored by tracking the intensity of a given pixel over time.

Movement of myotubes may be detected using a video camera mounted to a microscope as shown in FIG. 13. The video camera records frames and stores them to a computer. The frames are processed using a computer program that monitors a change in pixel intensity over time. For example, a given pixel of a video frame may have a first intensity when the associated myotube is in a relaxed state. The same pixel may have a second, different intensity when the associated myotube is in a contracted state. The differential in pixel intensity may be monitored over time and used to generate time plots of the contraction of the myotubes.

i. Immunocytochemistry

Cantilevers yielding functional neurotransmission data were assessed immunocytochemically for evidence of NMJ presence. Cantilever chips were first incubated with Alexa-Fluor-594-conjugated α-bungarotoxin (Life Technologies) for 1 hour at 37° C. and were then fixed in a 4% paraformaldehyde solution for 15 minutes.

Fixed cells were permeabilized through exposure to 0.1% triton X-100 (Sigma-Aldrich) diluted in phosphate buffered saline (PBS; Life Technologies). Following permeabilization and to reduce non-specific antibody binding, cells were blocked for one hour using 5% donkey serum (Millipore, Billerica, Mass.) and 0.5% bovine serum albumin (Sigma-Aldrich) diluted in PBS (blocking solution). After 1 hour, the blocking solution was aspirated and replaced with primary antibody solutions diluted in blocking solution. The primary antibodies used were as follows: Mouse-anti-Myosin Heavy Chain (MyHC) (DSHB, Iowa City, Iowa); diluted 1 in 10), rabbit-anti-β-III-Tubulin (Millipore; diluted 1 in 500) and mouse-anti-Synaptic Vesicle Protein 2 (SV2) (DSHB; diluted 1 in 10). Cells were incubated in the primary antibody solution overnight at 4° C.

Following primary antibody treatment, cells were washed three (3) times for 10 minutes each in PBS. The final wash was aspirated and replaced with secondary antibody solutions diluted in blocking solution. The secondary antibodies used were as follows: Donkey-anti-mouse-488 (Life Technologies; diluted 1 in 200), donkey-anti-rabbit-594 (Life Technologies; diluted 1 in 200) and donkey-anti-rabbit-647 (Life Technologies; diluted 1 in 200). Cultures were then placed in a darkened chamber for 2 hours at room temperature. After this time, cells were again washed three times for 10 minutes each in PBS. Immunostained cantilever chips were finally placed in 30 mm Petri dishes and submerged in fresh PBS. Imaging of the immunostained cells was carried out using water immersion lenses on a Zeiss Axioscope confocal microscope coupled to UltraVIEW™ LCI software (Perkin Elmer, Waltham, Mass.).

j. Statistical Analyses

Differences in force per contraction and in contraction frequency were measured for the three conditions: (i) Spontaneous activity, (ii) 200 μM glutamate, and (iii) 12.5 μM D-tubocurarine following glutamate. The differences were evaluated statistically using one-way repeated measures ANOVA ($\alpha=0.05$) both for the muscle-only controls and for the motoneuron-myotube co-cultures. Since the same set of myotubes were tested in all three conditions, the repeated measures ANOVA blocked for the variation among the myotubes and provided better power for the detection of differences caused by the testing conditions. The assumptions for ANOVA, i.e., quality of variances and normality, were tested using Bartlett's test and QQ-plots, respectively. Following the repeated measures ANOVA with a statistically significant F-statistic, means were statistically compared using Tukey's HSD test for multiple comparisons ($\alpha=0.05$). For the case of the contraction force, a logarithmic transformation was applied to the data to satisfy the ANOVA assumptions prior to ANOVA and Tukey's HSD tests. All values stated in the text are the mean±standard error of the mean.

ii) Example 1

Co-Culture of Myotubes and Motoneurons on Cantilevers

A. Characterization of Co-Culture

Figure 1B:
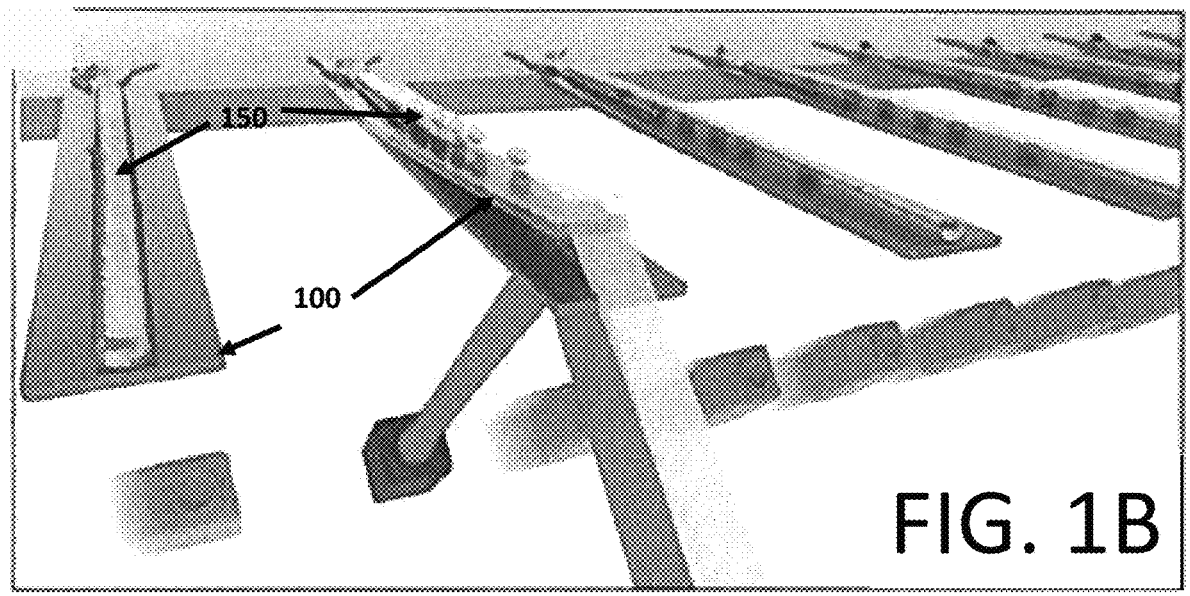
FIG. 1B shows a schematic representation of the scanning system used to measure cantilever deflection in response to myotube contraction.
Figure 1C:
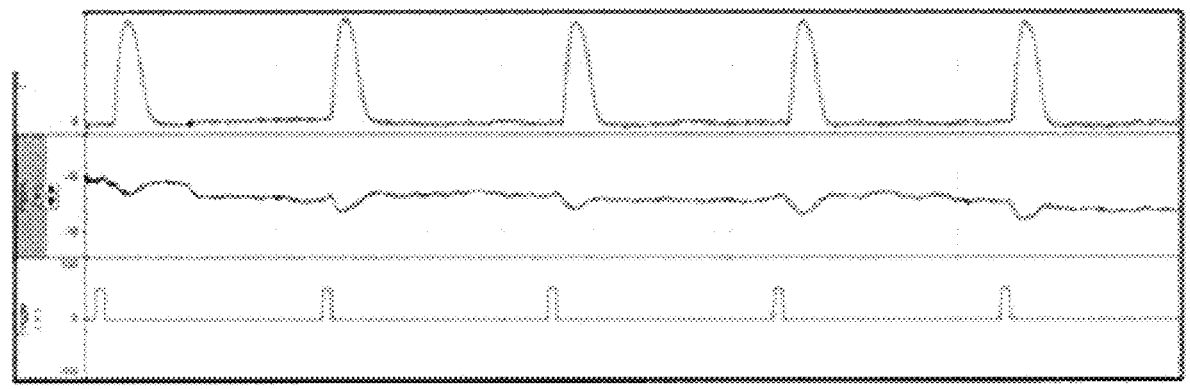
FIG. 1C shows an example of a trace recording from a myotube stimulated using broad field electrical pulses.

Prior to analysis, co-cultures of primary rat muscle cells and motoneurons were maintained on arrays of silicon cantilevers for 13 days in vitro. Measurement of myotube contraction on each cantilever was achieved using a scanning laser and photo-detector system which measured the deflection of the cantilever tip (FIG. 1). For example, FIG. 1B shows a schematic representation of the scanning system used to measure cantilever deflection in response to myotube contraction. Controlled movement of the laser and photo-detector was used to align the laser beam with the tip of each cantilever in turn. In this system, both myotube contraction in response to the neuronal stimulant glutamate, and cessation of contractions following addition of D-tubocurarine, were examined as evidence of functional neuromuscular transmission (and therefore NMJ formation). For instance, FIG. 1C shows an example of a trace recording from a myotube stimulated using broad field electrical pulses. In FIG. 1C, the top trace shows laser deflection (in Volts) in the x-axis, indicating lengthwise strain on the cantilever. In FIG. 1C, the middle trace shows laser deflection (in Volts) in the y-axis, indicating torsional strain across the cantilever. In FIG. 1C, the bottom trace shows indication of the temporal position of electrical pulses used to elicit myotube contraction in this system.

B. Stimulation of Motoneurons by Glutamate

Figure 2A:
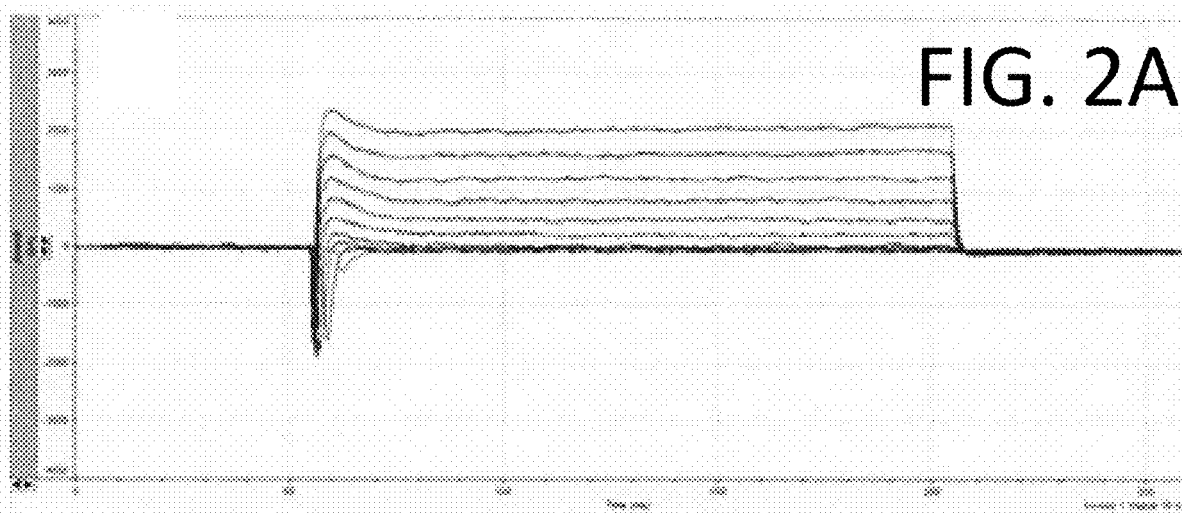
FIG. 2A shows using a disclosed device to generate voltage-clamp recordings.
Figure 2B:
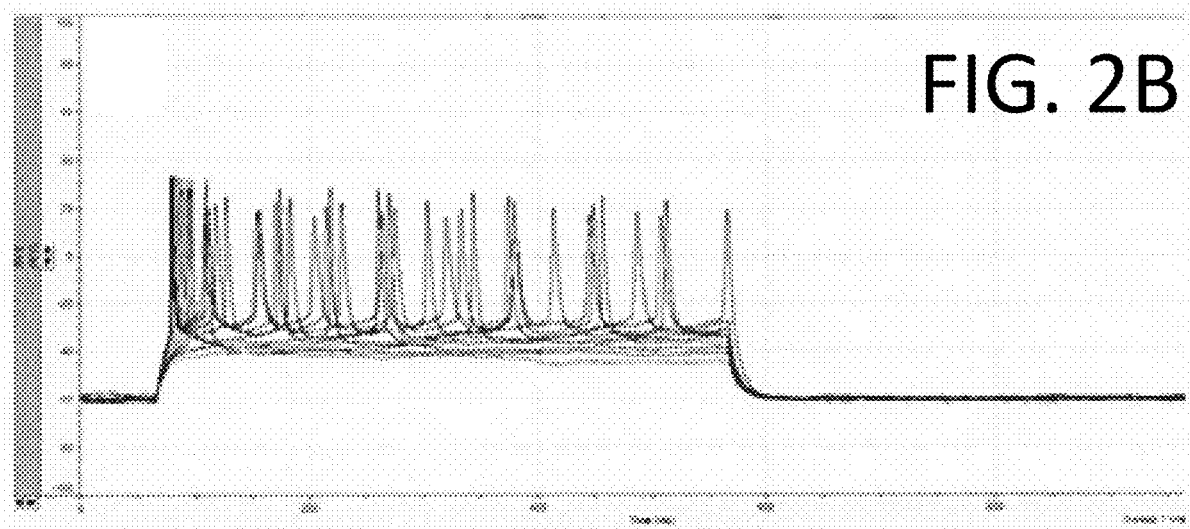
FIG. 2B shows a current-clamp recording at −70 mV.
Figure 2C:
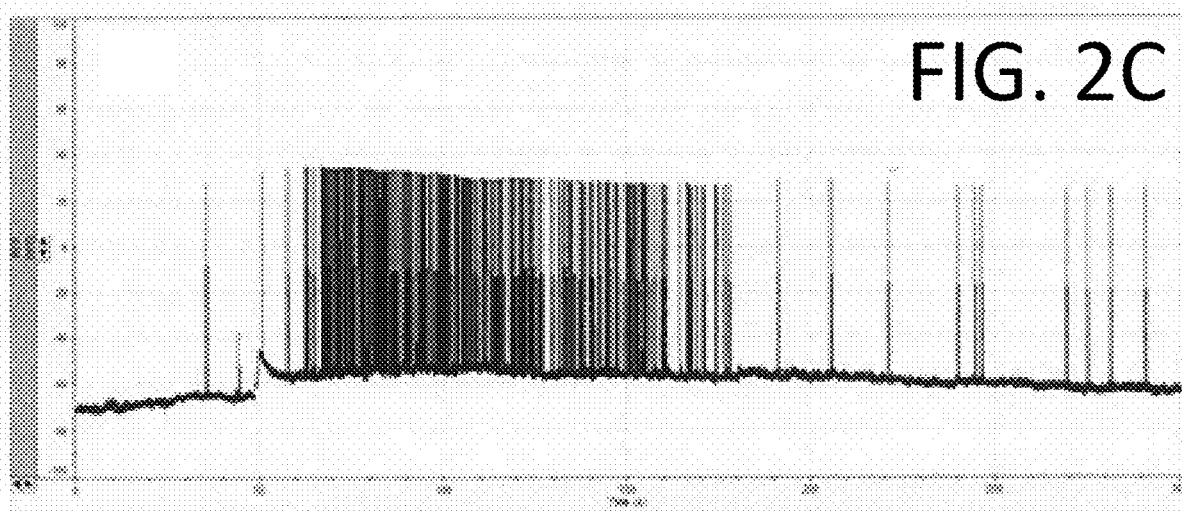
FIG. 2C shows gap-free, current-clamp (continuous) recordings following administration of glutamate.

Patch-clamp recordings verified the ability of the co-culture protocol to promote the maturation of electrically-active motoneurons after 11-13 days in culture. Such cells exhibited characteristic inward and outward ionic currents and depolarization-evoked action potentials as well as the ability to fire action potentials repetitively (voltage-clamp recording in FIG. 2A and current-clamp recording at −70 mV in FIG. 2B). Gap-free, current-clamp (continuous) recordings also demonstrated the response of these cells to bath application of glutamate (FIG. 2C—200 μM glutamate was added to the culture medium after 35 seconds recording). Such treatment resulted in the depolarization of the membrane and elicited action potentials in all motoneurons examined (n=17), which indicated the suitability of this treatment for stimulating these cells in vitro. Motoneuron activity in response to glutamate lasted roughly 2.5 minutes. To ensure a lack of contractile response was due to blocked AChR receptors rather than a lack of motoneuron firing, a second application of glutamate was provided prior to D-tubocurarine treatment during neurotransmission assessment. A second application of glutamate to patched cells again depolarized the motoneuron membrane in all cells examined (n=3).

C. Analysis of Functional Neuromuscular Transmission

In this examples described herein, an increase in contraction frequency of 2 Hz in response to glutamate treatment when compared to baseline spontaneous activity was the initial indicator of functional neuromuscular transmission. To exclude false positives, this increase in frequency criterion was selected as a means to distinguish small increases in frequency due to random variation. Cantilevers displaying such increases were further investigated through the addition of the neuromuscular blocking agent, D-tubocurarine. In all cases of glutamate increasing contraction frequency by at least 2 Hz, treatment with D-tubocurarine returned the contraction frequency to spontaneous levels.

Figure 3A:
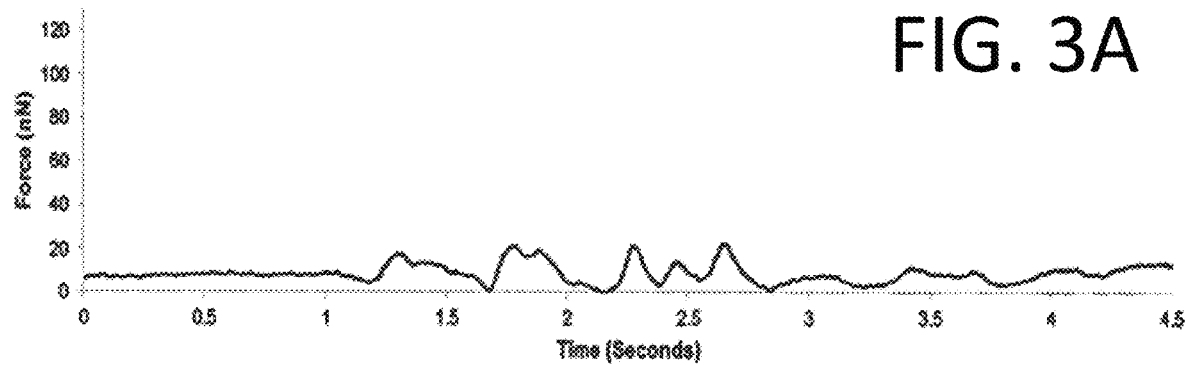
FIG. 3A shows using a disclosed device to measure spontaneous contractions by the cultured myotubes without neuronal stimulation.
Figure 3B:
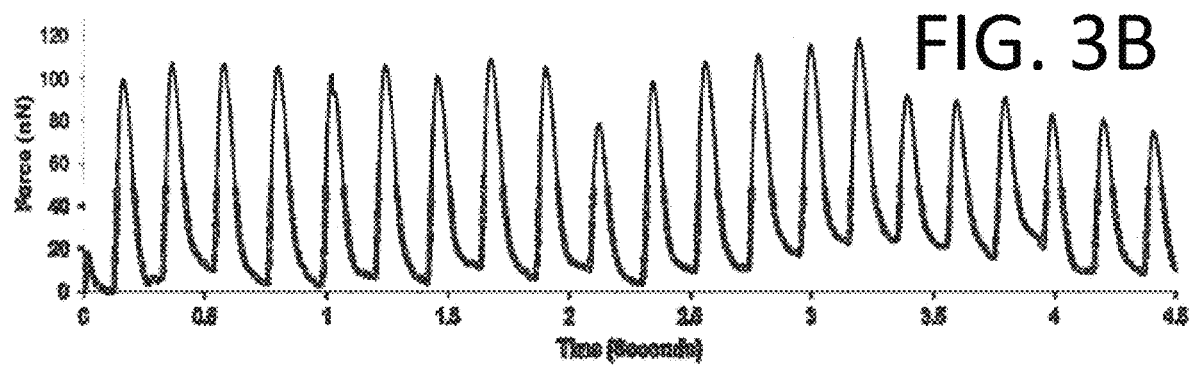
FIG. 3B shows myotube contraction following neuronal stimulation via the addition of 200 µM glutamate.
Figure 3C:
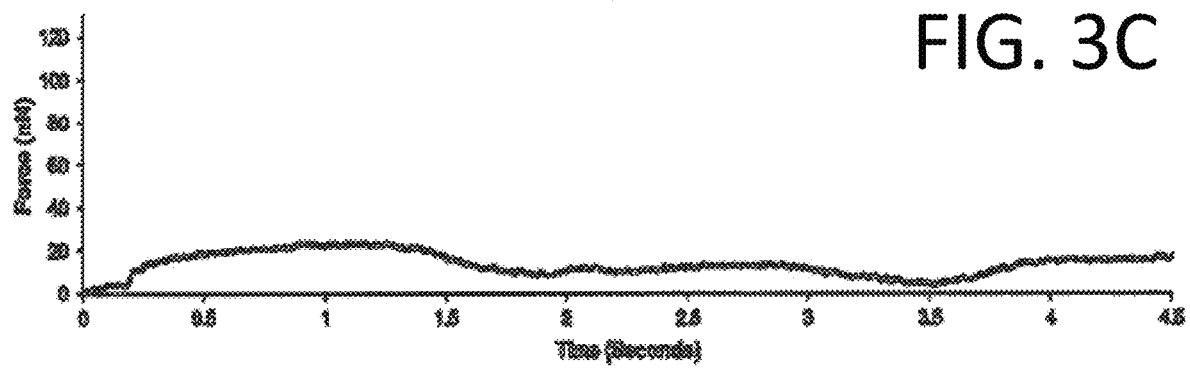
FIG. 3C shows myotube contraction following glutamate and tubocurarine treatment.

Using a disclosed device, approximately 12% of cantilevers examined provided such responses (n=10 out of 83 electrically active myotubes from 6 independent cultures), which indicated that successful neuromuscular transmission was possible and could be recorded using the described device. For example, FIG. 3 shows representative traces from analysis of the muscle-motoneuron co-culture cantilever system, demonstrating the functional effects of motoneuron stimulation with and without addition of a NMJ blocker. In FIG. 3, raw data (in volts) was converted to a measurement of myotube force (in nano-Newtons) and replotted. FIG. 3A shows measurement of spontaneous contractions by the cultured myotubes without neuronal stimulation. FIG. 3B shows measurement of myotube contraction following neuronal stimulation via the addition of 200 μM glutamate. FIG. 3C shows measurement of myotube contraction following glutamate and 12.5 μM curare treatment.

Among these cantilevers (which contained muscle-motoneuron co-cultures maintained for 13 days in vitro), the average contraction frequency increased significantly (p=0.002) from 1.4 Hz spontaneously to 4.9 Hz with glutamate treatment, and returned to 1.4 Hz with the addition of D-tubocurarine (FIG. 4A) (p=0.002). No significant difference was observed between spontaneous frequency and frequency after the combined additions of glutamate and D-tubocurarine (p=0.99).

Figure 4A:
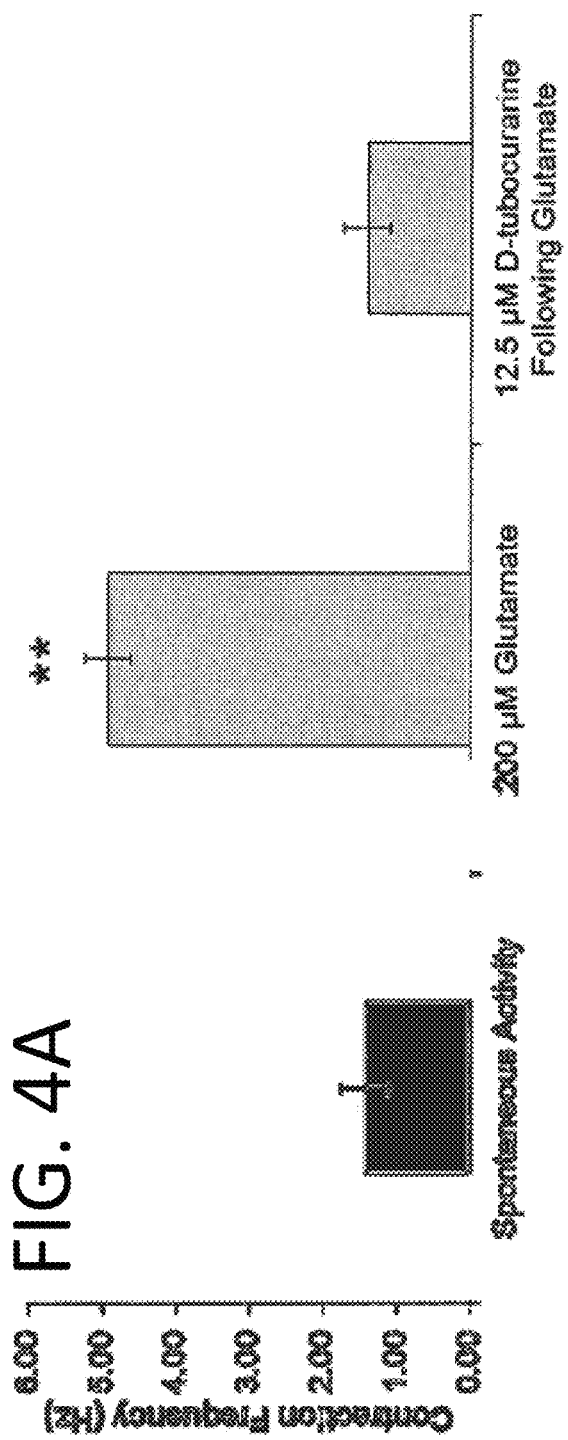
FIG. 4A shows the average contraction frequency of a co-culture following glutamate treatment and following glutamate treatment with tubocurarine.
Figure 4B:
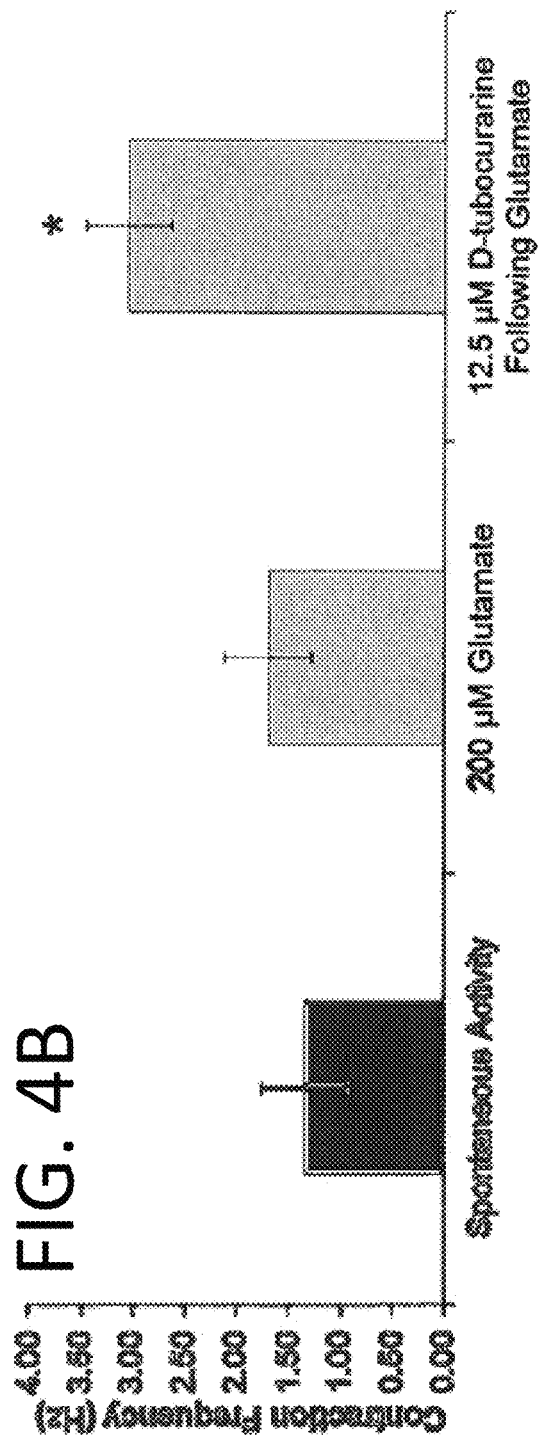
FIG. 4B shows the average contraction frequency of muscle cells only following glutamate treatment and following glutamate treatment with tubocurarine.

Controls behaved as expected. Glutamate treatment on electrically active myotubes from muscle-only cultures did not significantly alter contraction frequency across all cantilevers examined (n=10). In the muscle-only controls, the largest increase in frequency observed in response to glutamate was 0.85 Hz (FIG. 4B), roughly 2.5 times smaller than the selection criterion used to indicate neuromuscular transmission. Additionally, D-tubocurarine had no inhibitory effect on myotube contraction in all control cases. In FIG. 4A and FIG. 4B, the following apply: n=10 (individual cantilever recordings selected from 6 separate cultures), the error bars=standard error of the mean, * indicates a p value of p<0.05, and ** indicates a p value of p<0.01. A significant increase in contraction frequency was observed in D-tubocurarine treated, muscle-only controls when compared with the frequency these myotubes exhibited in response to glutamate treatment (p=0.04).

FIG. 5 shows an assessment of the functional effects of glutamate and tubocurarine tubocurarine on myotube contractile force in the muscle-motoneuron co-cultures. Analysis of the contractile peaks demonstrated that glutamate treatment had no significant effect on the force generated by the contracting myotubes in co-culture with motoneurons (FIG. 5A; n=10; p=0.60) and no effect in muscle-only controls (FIG. 5B; n=7; p=0.24). In co-cultures, a non-significant decrease in force between spontaneous contractions (106.0 nN±70.0) and glutamate-evoked contractions (67.4 nN±19.4) was observed. Once neuromuscular transmission was blocked through addition of D-tubocurarine to the culture medium, the resulting spontaneous contractions (45.1 nN±15.0) were not significantly different from the contractile force produced in response to glutamate treatment.

D. Immunocytochemical Characterization of Co-Cultures

Cultures stained for Myosin Heavy Chain (MyHC) and β-III-Tubulin demonstrated the close association of myotubes and neuritic extensions on cantilevers. For example, FIG. 1A is a composite image of a primary rat myotube co-cultured with primary rat motoneurons on a cantilever for 13 days in vitro and immunostained for Myosin Heavy Chain (green) and β-III-Tubulin (red). Cantilever edges in this image were reinforced artificially to give an indication of their scale in relation to the cultured cells. (scale bar=100 µm). The highly striated nature of the examined myotubes indicated development of organized contractile machinery within these cells and supported evidence from the laser and photo-detector system for functional maturity of the analyzed myotubes.

Figure 6:
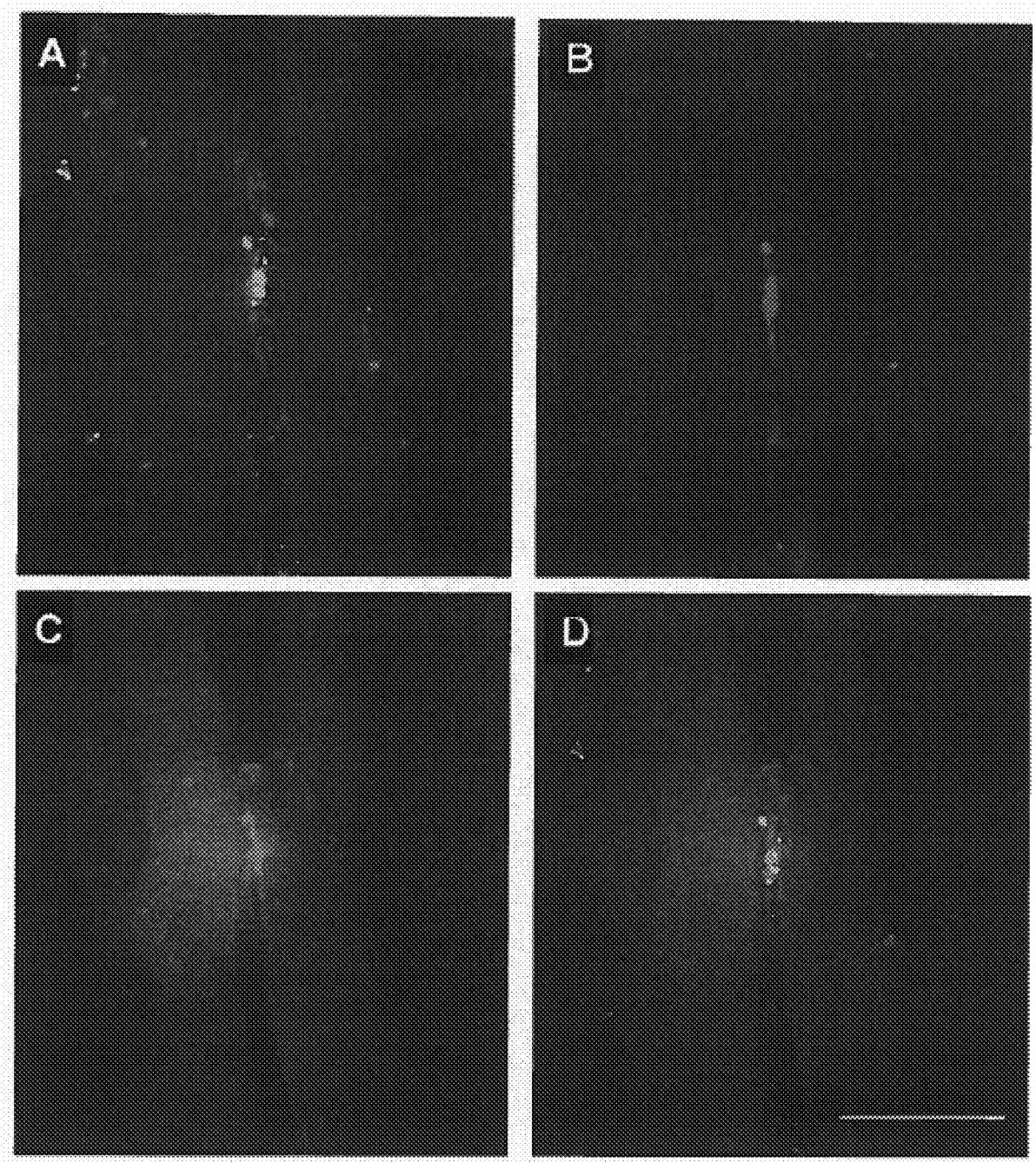
FIG. 6 shows immunocytochemical evidence for synaptic contact between myotubes and motoneurons maintained in a co-culture.

Extensive β-III-Tubulin (FIG. 6B) staining not only verified the survival of neurons in this co-culture model, but also identified substantial levels of neurite outgrowth from cells in this system. FIG. 6D shows co-localization of the pre-synaptic marker, Synaptic Vesicle Protein 2 (SV2) (FIG. 6A), with acetylcholine receptors (AChRs) stained with Alexa-Fluor-594-conjugated α-bungarotoxin (FIG. 6C), which indicated the close association of pre- and post-synaptic markers in the examined cultures. This close association identified the likely locations for neuromuscular cellular contact and synaptic transmission. FIG. 6 provides representative composite images of the appositions observed on examined cantilevers.

iii) Example 2

Co-Culture of Myotubes and Motoneurons in a Two-Chamber Device

A. Design of a Two-Chamber Device

Figure 8A:
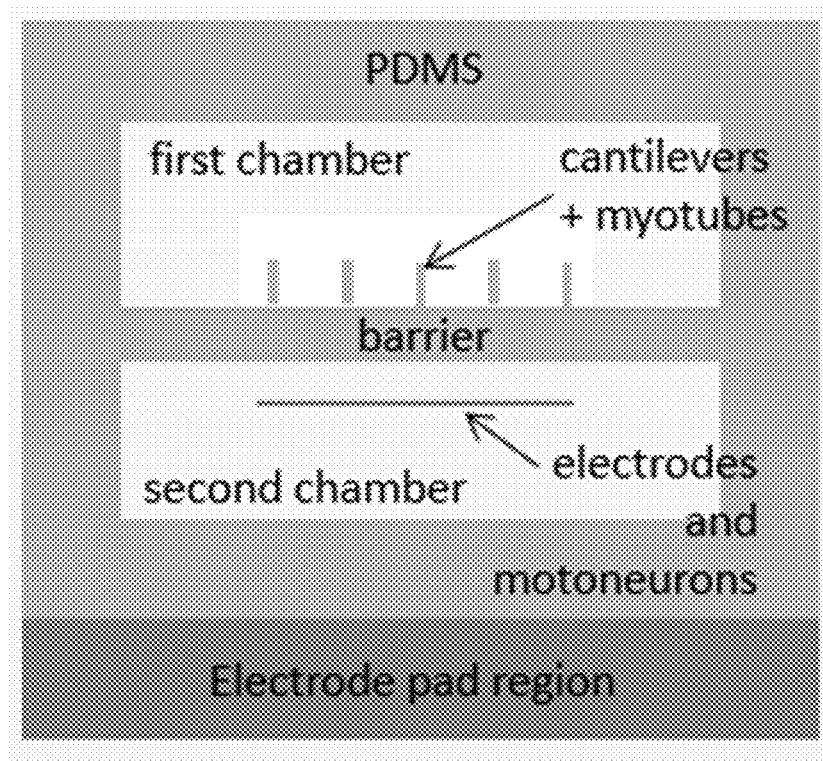
FIGS. 8A-B are schematics of a device comprising a first chamber and a second chamber.
Figure 8B:
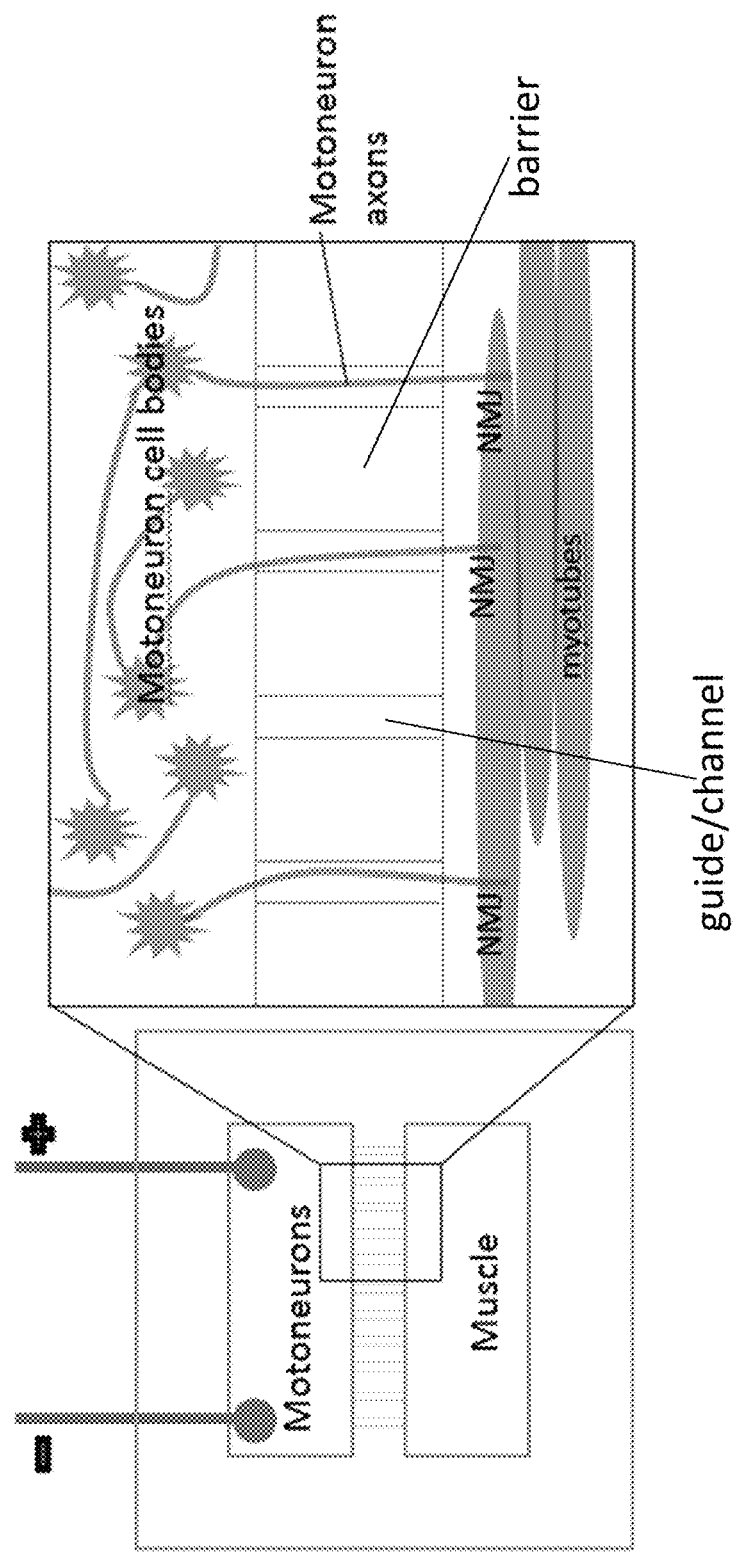

FIGS. 8A-B are schematics of a device comprising a first chamber and a second chamber. As shown in FIG. 8A, the cantilevers are located in the first chamber and are spaced from the second chamber by a PDMS barrier. The barrier, in this example, isolates the cantilevers from an electrode region in the adjacent second chamber. A magnified schematic is shown in FIG. 8B. In this example, a positive (+) and a negative (−) electrode extend into the second chamber with the motoneurons. The barrier comprises guide channels extending through the PDMS between the two chambers. Axons from motoneurons can extend through the channels formed through the barrier and synapse with the myotubes cultured on the other side, in the first chamber. The synapsing of the motoneuron axons to the myotubes forms neuromuscular junctions (NMJ).

Figure 9A:
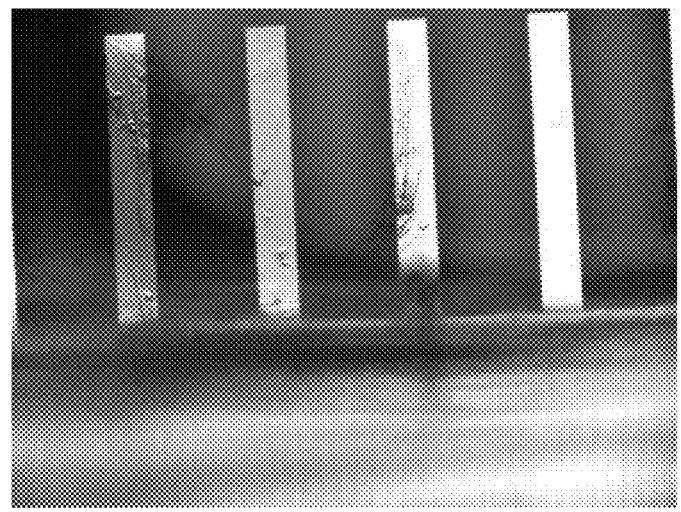
FIGS. 9A-C show phase contrast images.
Figure 9B:
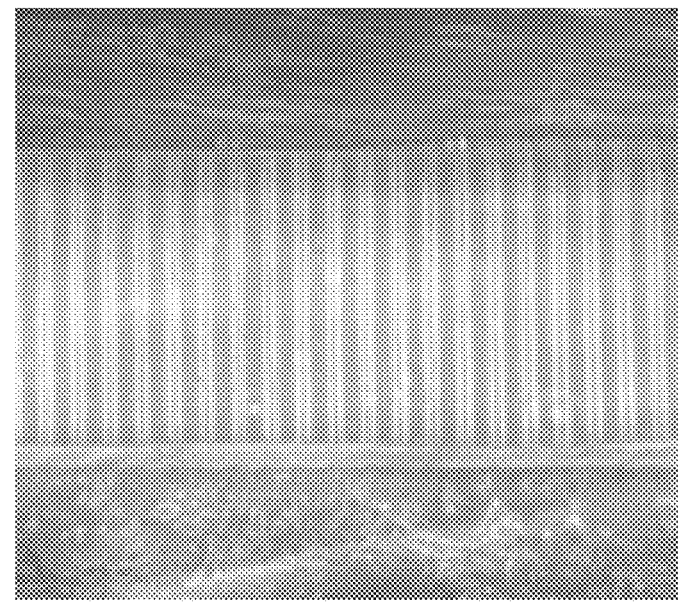
Figure 9C:
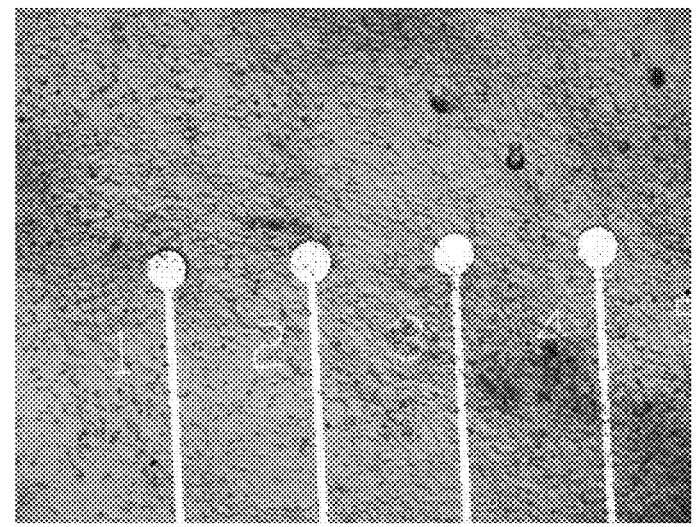

FIGS. 9A-C show phase contrast microscopy images of myotubes cultured on the surface of the cantilevers in the first chamber (FIG. 9A), the guide channels extending through the barrier between the chambers (FIG. 9B), and motoneurons cultured on the surface of a plurality of electrodes in the second chamber (FIG. 9C). In this example, the electrodes shown are part of a microelectrode array.

In some examples, the electrodes (such as those shown in FIG. 8B or 9C) may stimulate the motoneuron culture. Functioning neuromuscular junctions may be detected by monitoring the effect of the electrode stimulation on the myotubes cultured in the opposite, first chamber. Movement of a myotube indicates transmission of the electrical signal through a functioning neuromuscular junction. Movement of a myotube may be detected either by a video camera or by deflection of a cantilever (using the laser/photo detector system or transducer systems described above).

B. Immunocytochemical Characterization

Figure 10A:
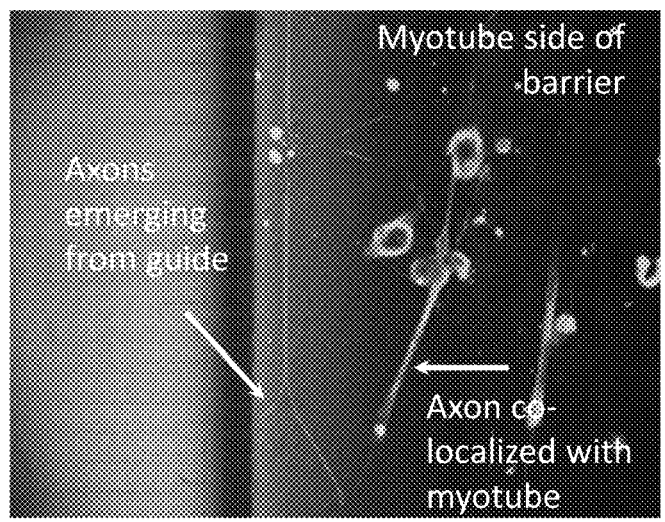
FIGS. 10A-C show immunocytochemical images of motoneuron axons extending into the second chamber with the myotubes.
Figure 10B:
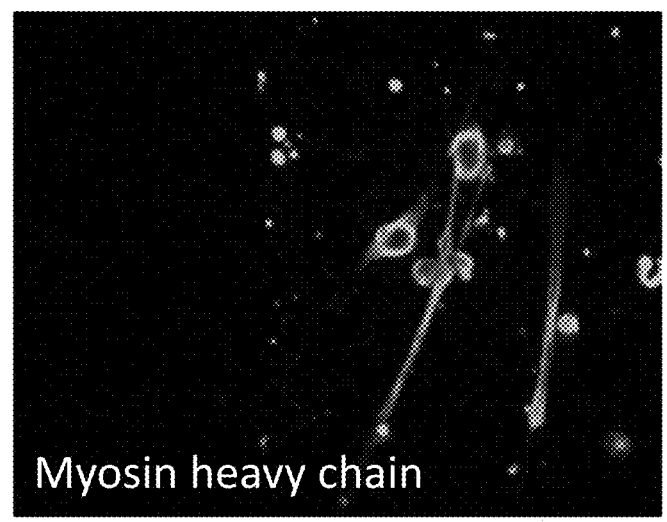
Figure 10C:
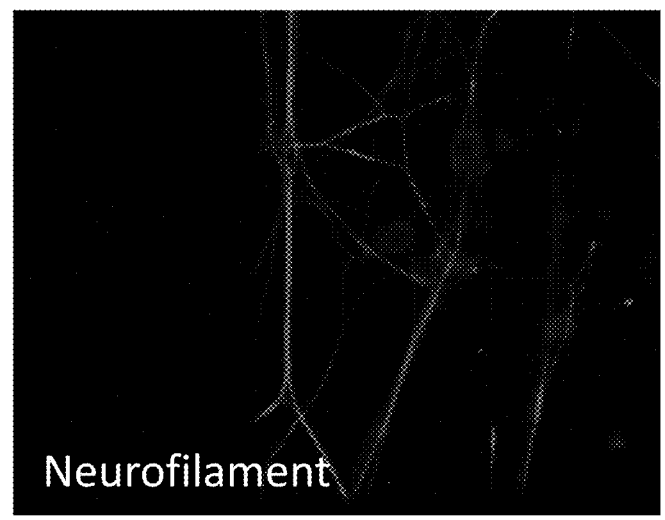
Figure 11A:
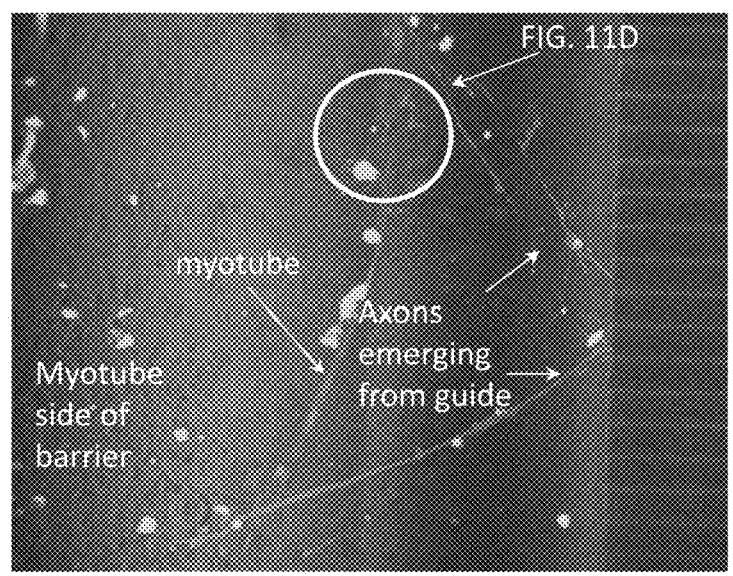
FIGS. 11A-C show immunocytochemical images of motoneuron axons extending into the second chamber with the myotubes.
Figure 11B:
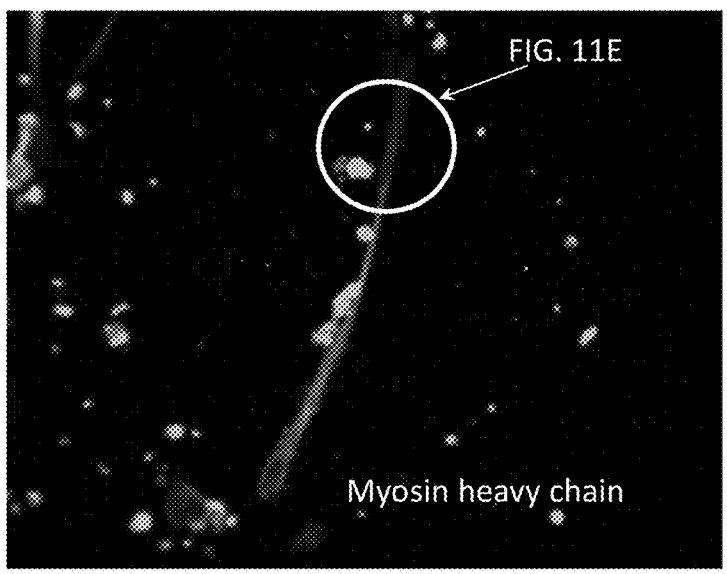
Figure 11C:
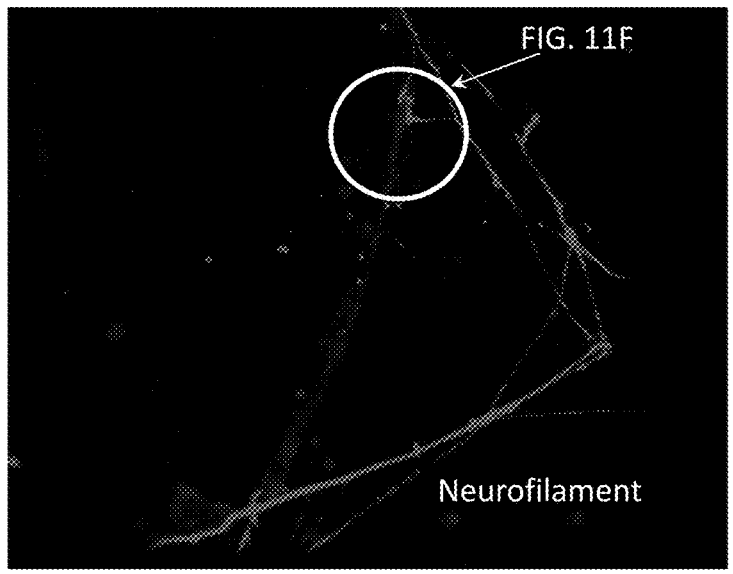
Figure 11D:
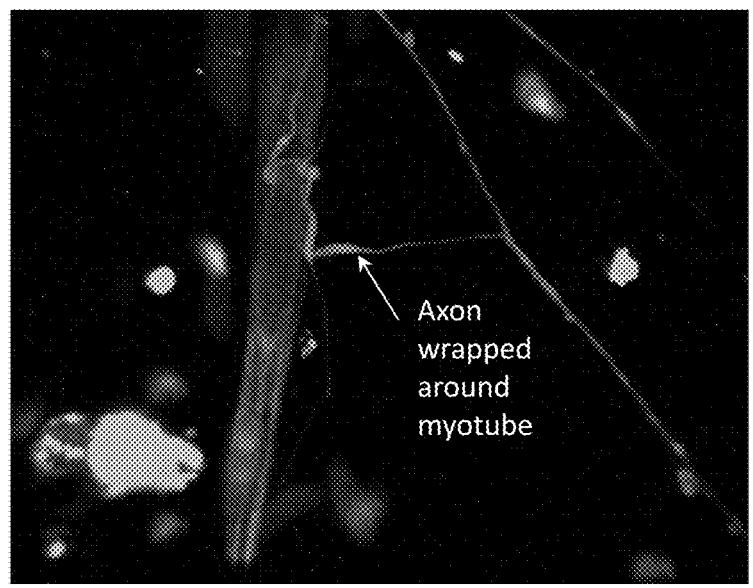
FIG. 11D shows an overlay of both myosin heavy chain and neurofilament staining
Figure 11E:
FIG. 11E shows the myosin heavy chain staining individually.
Figure 11F:
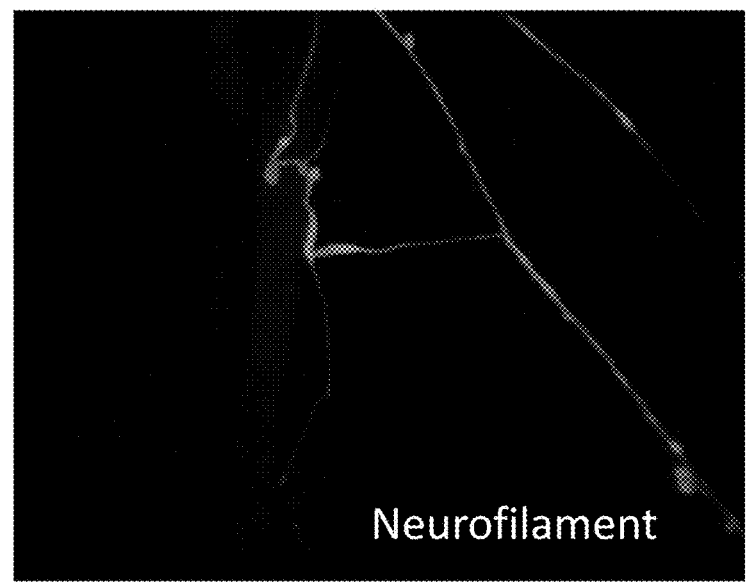
FIG. 11F shows the neurofilament staining individually.

FIGS. 10A and 11A are phase contrast images overlaid with immunocytochemical staining. In FIGS. 10A and 11A, axons from the motoneurons cultured in the adjacent second chamber extend out from the guide channels. FIGS. 10B and 11B are the same field of view as FIGS. 10A and 11A, but showing only the immunocytochemical staining for myosin heavy chain (a myotube marker). FIGS. 10C and 11C are the same field of view as FIGS. 10A and 10B, but showing only the immunocytochemical staining for neurofilament (a neural marker). FIGS. 11 D-F are magnified views of the circles from FIGS. 11A-C. FIG. 11D shows an overlay of both myosin heavy chain and neurofilament staining, while FIGS. 11E-F show the stains individually. In FIG. 11D, an axon (stained with neurofilament) is seen wrapped around a myotube (stained with myosin heavy chain).

Figure 12A:
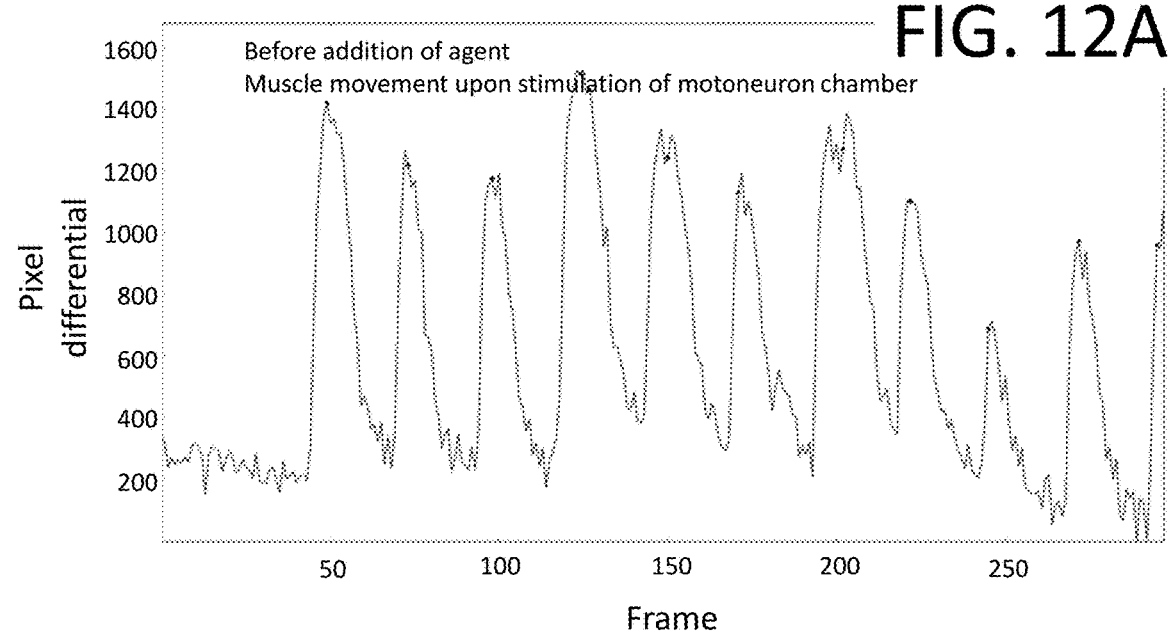
FIGS. 12A-E show time plots of myotube contractions detected by a video camera with different concentrations of α-bungarotoxin (with a 10 minute wait between doses). The co-culture was stimulated at 1 Hz from the second chamber (the motoneuron side) in each of FIGS. 12A-D.
Figure 12B:
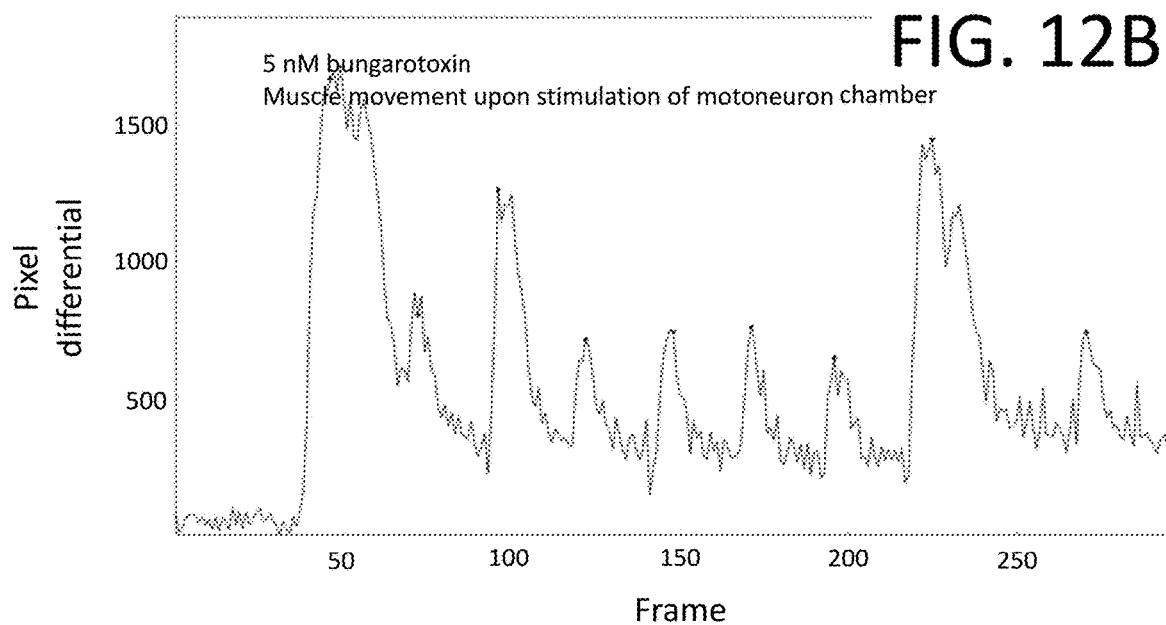
Figure 12C:
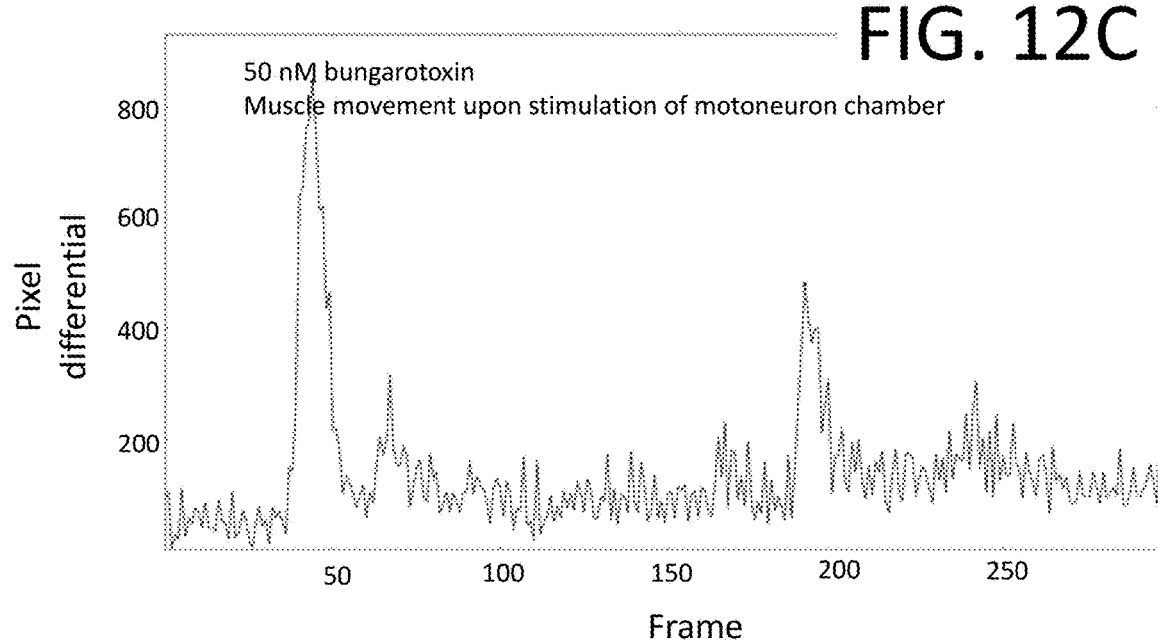
Figure 12D:
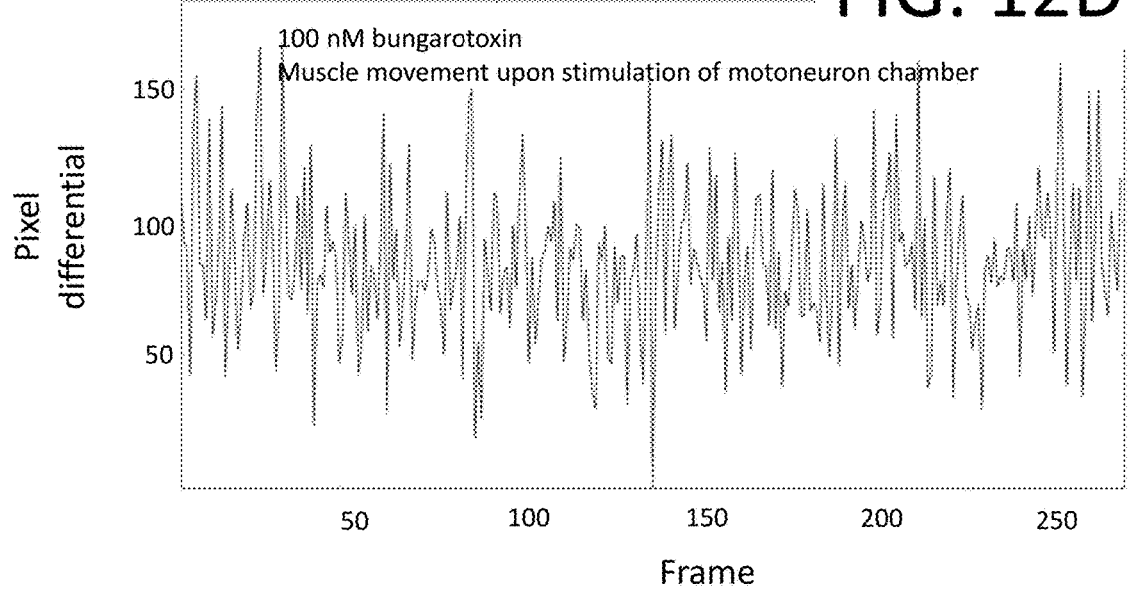
Figure 12E:
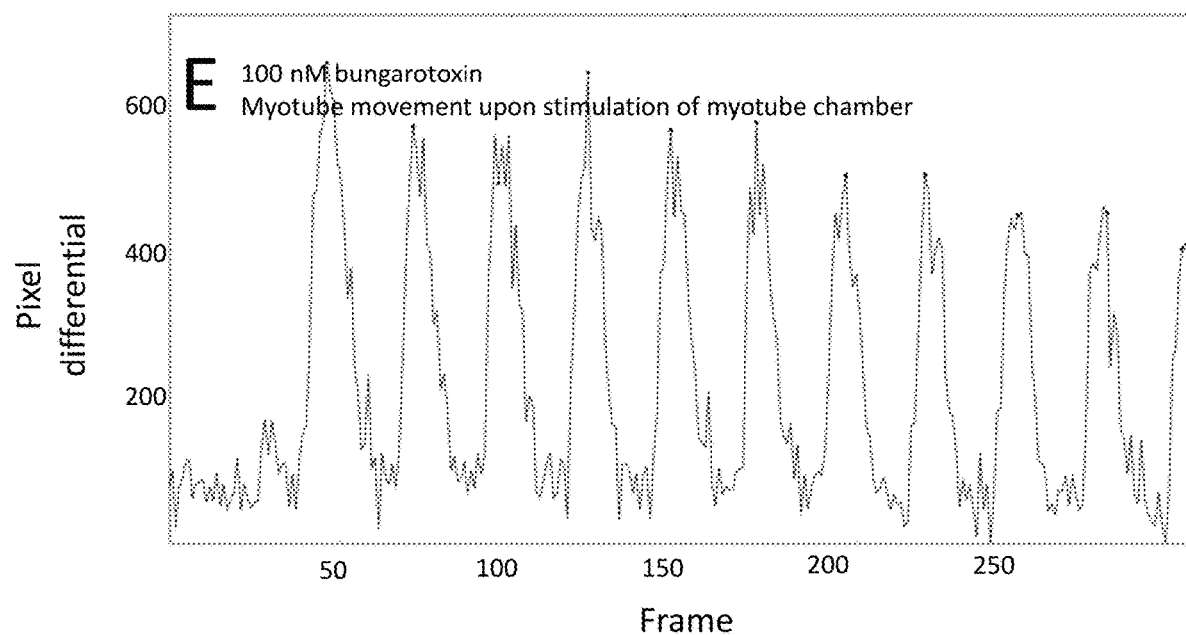

C. Inhibition of Neuromuscular Junctions by Alpha-Bungarotoxin

α-Bungarotoxin a neurotoxic protein that is known to bind competitively and in a relatively irreversible manner to the nicotinic acetylcholine receptor found at the neuromuscular junction. FIGS. 12A-D show time plots of myotube contractions detected by a video camera with increasing concentrations of α-bungarotoxin (with a 10 minute wait between doses). The co-culture was stimulated at 1 Hz from the second chamber (the motoneuron side), and contraction of the myotubes was mediated via the neuromuscular junction. Increasing concentrations of bungarotoxin caused the myotubes to be less and less responsive to the drug. However, as shown in FIG. 12E, the bungarotoxin did not inhibit contraction when the electrical stimulation was applied directly from the first chamber (the myotube side), indicating that the drug indeed affects the neuromuscular junction itself.

iv) Experimental Advantages

This examples provided here characterize the development of a co-culture model for primary myotubes and motoneurons and demonstrate the ability of the disclosed devices to record functional myotube contraction data in response to neuronal stimulation. The disclosed devices facilitated the simultaneous analysis of an array cantilevers, thereby (i) enabling the multiplex analysis of all potential myotube-neuron pairings and (ii) providing greater power to the analysis of successful transmission events. For example, a disclosed device comprising a plurality of cantilevers and an automated detection system allowed for 32 independent data points from a single chip or chip in a well to be simultaneously examined, which provided far greater statistical power for analysis. Such a disclosed device allowed for the paired analysis of sequential experimental conditions.

The devices disclosed herein can record physiological data (e.g., peak force, time to half relaxation, and recovery following myotube exhaustion) in response to stimulation via neuromuscular junctions. Thus, the disclosed devices can be very advantageous (i) to the study of muscle diseases and conditions, (ii) the study of NMJ pathology, and (iii) to high-content phenotypic screen for novel therapeutics.

Furthermore, using a disclosed device, a co-culture was maintained an extensive time period. Such a prolonged culture increases the applicability of a disclosed device for drug efficacy and toxicity studies and for modeling of disease states in vitro (i.e., facilitates the examination of more chronic and acute behavior and responses).

F. References

Bloch-Gallego E, et al. 1991. Survival in vitro of motoneurons identified or purified by novel antibody-based methods is selectively enhanced by muscle-derived factors. Development. 111:221-32.
Bowman W C. 2006. Neuromuscular block. Br J Pharmacol. 147:S277-S86.
Brewer G J, et al., 2008. NBActiv4 medium improvement to neurobasal/B27 increases neuron synapse densities and network spike rates on multielectrode arrays. J Neurosci Methods. 170(2):181-187.
Daniels M P, et al. 2000. Rodent nerve-muscle cell culture system for studies of neuromuscular junction development: refinements and applications. Microsc Res Tech. 49:26-37.
Das M, et al. 2006. A defined system to allow skeletal muscle differentiation and subsequent integration with silicon microstructures. Biomaterials. 27:4374-4380.
Das M, et al. 2010. A defined long-term in vitro tissue engineered model of neuromuscular junctions. Biomaterials. 31:4880-4888.
Das M, et al. 2007. Embryonic motoneuron-skeletal muscle co-culture in a defined system. Neuroscience. 146:481-488.
Eisenberg T, et al. 2009. Induction of autophagy by spermidine promotes longevity. Nat Cell Biol. 11:1305-1314.
Esch M B, et al. 2011. The role of body-on-a-chip devices in drug and toxicity studies. Annu Rev Biomed Eng. 13:55-72.
Esch M B, et al. 2012. On chip porous polymer membranes for integration of gastrointestinal tract epithelium with microfluidic 'body-on-a-chip' devices. Biomed Microdevices. 14:895-906.
Faraut B, et al. 2004. Thrombin reduces MuSK and acetylcholine receptor expression along with neuromuscular contact size in vitro. Eur J Neurosci. 19:2099-2108.
Fuentes-Medel Y, et al. 2012. Integration of a Retrograde Signal during Synapse Formation by Glia-Secreted TGF-β Ligand. Curr Biol. 22(19):1831-1838.
Guo X, et al. 2010. Neuromuscular junction formation between human stem-cell-derived motoneurons and rat skeletal muscle in a defined system. Tissue Eng Part C Methods. 16:1347-1355.
Guo X, et al. 2011. Neuromuscular junction formation between human stem cell-derived motoneurons and human skeletal muscle in a defined system. Biomaterials. 32:9602-9611.
Huh D, et al. 2012. Microengineered physiological biomimicry: organs-on-chips. Lab Chip. 12:2156-2164.
Jevsek M, et al. 2004. Origin of acetylcholinesterase in the neuromuscular junction formed in the in vitro innervated human muscle. Eur J Neurosci. 20:2865-2871.
Jiang Z G, et al. 1990. Excitatory and inhibitory transmission from dorsal root afferents to neonate rat motoneurons in vitro. Brain Res. 535:110-118.
Kaeberlein M. 2009. Spermidine surprise for a long life. Nat Cell Biol. 11:1277-1278.
Larkin L M, et al. 2006. Functional evaluation of nerve-skeletal muscle constructs engineered in vitro. In Vitro Cell Dev Biol Anim. 42:75-82.
Long C, et al. 2012. Design optimization of liquid-phase flow patterns for microfabricated lung on a chip. Ann Biomed Eng. 40:1255-1267.
Machida S, et al. 2004. Primary rat muscle progenitor cells have decreased proliferation and myotube formation during passages. Cell Prolif. 37:267-277.
Mars T, et al. 2001. Differentiation of glial cells and motor neurons during the formation of neuromuscular junctions in cocultures of rat spinal cord explant and human muscle. J Comp Neurol. 438:239-251.
Miles G B, et al. 2004. Functional properties of motoneurons derived from mouse embryonic stem cells. J Neurosci. 24:7848-7858.
Nishimaru H, et al. 2005. Mammalian motor neurons corelease glutamate and acetylcholine at central synapses. Proc Natl Acad Sci USA. 102:5245-5249.
Rumsey J W, et al. 2010. Tissue engineering the mechanosensory circuit of the stretch reflex arc: Sensory neuron innervation of intrafusal muscle fibers. Biomaterials. 31:8218-8227.
Rumsey J W, et al. 2009. Node of Ranvier formation on motoneurons in vitro. Biomaterials. 30:3567-72.
Shuler M L. 2012. Modeling life. Ann Biomed Eng. 40:1399-1407.
Umbach J A, et al. 2012. Functional neuromuscular junctions formed by embryonic stem cell-derived motor neurons. PLoS ONE. 2012:7.
Urazaev A K, et al. 1995. Muscle NMDA receptors regulate the resting membrane potential through N O-synthase. Physiol Res. 44:205-208.
Wilson K, et al. 2010. Measurement of contractile stress generated by cultured rat muscle on silicon cantilevers for toxin detection and muscle performance enhancement. PLoS ONE. 2010:5.
Wu H, et al. 2010. To build a synapse: signaling pathways in neuromuscular junction assembly. Development. 137:1017-1033.

What is claimed is:
1. A device, comprising:
a first chamber comprising a myotube culture attached to a plurality of cantilevers;
a second chamber spaced from the first chamber by a barrier, the second chamber comprising a motoneuron culture attached to and in electrical communication with a microelectrode array, and an automated detection system configured to detect a deflection of the at least one cantilevers, and at least one motoneuron selected from the motoneuron culture, the at least one motoneuron comprising a cell body, an axon, and a terminal, wherein the cell body is in electrical communication with the microelectrode array in the second chamber, the axon extends through an opening of the barrier, and the terminal is in electrophysiological communication with a myotube in the first chamber to form a neuromuscular junction, and wherein electrical stimulation of the motoneuron culture via the microelectrode array causes electrophysiological signal transmission through the axon and the neuromuscular junction to a myotube of the myotube culture, causing the myotube to contract and deflect at least one cantilever of the plurality of cantilevers.

2. The device of claim 1, wherein the automated detection system comprises a laser and a photo-detector.

3. The device of claim 1, wherein muscle cells or myoblasts fuse together to form one or more of the myotubes.

4. The device of claim 1, wherein the at least one cantilever comprises one or more piezoelectric materials.

5. The device of claim 4, wherein the automated detection system comprises a transducer for detecting a change in electrical conductivity of the at least one cantilever.

6. The device of claim 4, wherein piezoelectric materials comprise at least one of quartz, bone, sodium tungstate, zinc oxide, lead zirconate titanate, or a combination thereof.

7. The device of claim 1, wherein the at least one cantilever comprises at least two cantilevers.

8. The device of claim 2, wherein the automated detection system further comprises a plurality of linear actuators attached to XY translational stages that control the position of the laser and the photo-detector.

9. The device of claim 2, further comprising a digitizer and a computer, wherein the photo-detector is in communication with the digitizer and wherein the digitizer is in communication with the computer.

10. The device of claim 1, further comprising a temperature-controlled stage, wherein the at least one cantilever is maintained on the temperature-controlled stage, and wherein the temperature-controlled stage comprises one or more electrodes and one or more pulse generators.

11. The device of claim 10, further comprising a digitizer and a computer, wherein the one or more pulse generators is in communication with the digitizer, and wherein the digitizer is in communication with the computer.

12. The device of claim 1, wherein the at least one cantilever is surface-modified or surface-coated.

13. The device of claim 12, wherein the at least one cantilever comprises a (3-Trimethoxysilyl propyl) diethylenetriamine (DETA) surface modification.

14. The device of claim 1, wherein the myotubes are human or rat myotubes, and the motoneurons are human or rat motoneurons.

15. The device of claim 1, wherein at least one of the myotubes or motoneurons is obtained from a subject diagnosed with or suspected of having a muscle wasting condition, a peripheral neuropathy, or both.

16. The device of claim 1, further comprising a serum-free medium, wherein the co-culture is maintained in the serum-free medium.

17. The device of claim 16, wherein the serum-free medium comprises neurobasal medium, B27, Glutamax, glial-derived neurotrophic factor, brain-derived neurotrophic factor, ciliary neurotrophic factor, insulin-like growth factor-1, neurotrophin-3, neurotrophin-4, mouse laminin, and cAMP.

18. The device of claim 1, further comprising extracellular matrix molecules, chemotactic factors, or a combination thereof patterned on a surface of the device positioned between the first chamber and the second chamber.

19. The device of claim 1, wherein the device is an in vitro device.

20. The device of claim 1, further comprising a barrier arranged between the first chamber and the second chamber, the barrier comprising a plurality of openings.

21. The device of claim 20, wherein the barrier further comprises a plurality of channels, and the axon extends through a channel of the plurality of channels.

* * * * *